(12) United States Patent
Shrader et al.

(10) Patent No.: US 7,495,070 B2
(45) Date of Patent: *Feb. 24, 2009

(54) PROTEIN BINDING MINIATURE PROTEINS

(75) Inventors: Alanna Schepartz Shrader, Wilton, CT (US); Jason W. K. Chin, Cambridge (GB); Reena Zutshi, Tucson, AZ (US); Stacey E. Rutledge, Cambridge (GB); Tanya L. Schneider, Harpswell, ME (US); Heather M. Volkman, New Haven, CT (US)

(73) Assignee: Yale University, Hartsford, CT (US)

( * ) Notice: Subject to any disclaimer, the term of this patent is extended or adjusted under 35 U.S.C. 154(b) by 86 days.

This patent is subject to a terminal disclaimer.

(21) Appl. No.: 10/982,727

(22) Filed: Nov. 4, 2004

(65) Prior Publication Data

US 2005/0287542 A1 Dec. 29, 2005

Related U.S. Application Data

(63) Continuation-in-part of application No. 09/840,085, filed on Apr. 24, 2001, now Pat. No. 7,297,762.

(60) Provisional application No. 60/517,496, filed on Nov. 4, 2003, provisional application No. 60/271,368, filed on Feb. 23, 2001, provisional application No. 60/265,099, filed on Jan. 30, 2001, provisional application No. 60/240,566, filed on Oct. 16, 2000, provisional application No. 60/199,408, filed on Apr. 24, 2000.

(51) Int. Cl.
C07K 14/465 (2006.01)
C07K 14/46 (2006.01)

(52) U.S. Cl. ..................................... 530/324

(58) Field of Classification Search .............. None
See application file for complete search history.

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,571,698 A | 11/1996 | Ladner et al. | |
| 5,580,717 A | 12/1996 | Dower et al. | |
| 5,612,454 A * | 3/1997 | Kaminuma et al. | 530/344 |
| 5,656,725 A | 8/1997 | Chittenden et al. | |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler et al. | |
| 5,821,047 A | 10/1998 | Garrard et al. | |
| 5,837,500 A | 11/1998 | Ladner et al. | |
| 5,969,108 A | 10/1999 | McCafferty et al. | |

2003/0166240 A1 9/2003 Shrader et al.

FOREIGN PATENT DOCUMENTS

WO WO 01/81375 11/2001
WO WO 03/053996 7/2003

OTHER PUBLICATIONS

Genbank Sequence Accession No. P38803, May 30, 2000.*
Genbank Sequence Accession No. P43316, Dec. 15, 1998.*
Chin, J.W., et al. "Methodology for optimizing functional miniature proteins based on avian pancreatic polypeptide using phage display," Bioorganic & Medicinal Chemistry Letters, 11(12):1501-1505 (2001).
Schepartz, A., "Design and Discovery of Functional Miniature Proteins," American Chemical Society. Abstracts of Paper. At the National Meeting, American Chemical Society, Washington, DC, US, vol. 223(1/2) (2002).
Chin, J.W. and Schepartz, A., "Design and Evolution of a Miniature BCL-2 binding protein," Angewandte Chemie. International Edition, Wiley Vch Verlag, Weinheim, DE, vol. 40(20):3806-3809 (2001).
Rutledge, S.E., et al., "Design and Selection of Protein-Binding Miniature Proteins," American Chemical Society. Abstract of Paper. At the National Meeting, American Chemical Society, Washington, DC, US, vol. 224(1/2) (2002).
Cunningham, B.C., et al., "Minimized Proteins," Current Opinion in Structural Biology, Current Biology Ltd., London, GB, vol. 7(4):457-462 (1997).
Rutledge S.E., et al., "Molecular recognition of protein surfaces: high affinity ligands for the CBP KIX domain," Journal of the American Chemical Society, 125(47):14336-14347 (2003).
Agre, et al., Science, 246:922-826 (1989).
Arnes, et al. J. Immunol. Methods, 184:177-186 (1995).
Andrews, et al., Tetrahedron, 55:11711-11743 (1999).
Armstrong, et al., J. Mol. Biol., 230:284-291 (1993).
Blackwell, et al., Angew. Chem. Int. Ed., 37:3281-3284 (1998).
Blundell, et al., Proc. Natl. Acad. Sci. USA, 78:4175-4179 (1981).
Braisted, et al., Proc. Natl. Acad. Sci., USA, 93:5688-5692 (1996).
Brinkmann et al., J. Immunol. Methods, 182:41-50 (1995).
Burton, et al., Adv. Immunol., 57:191-280 (1994).
Cohen, et al., Proc. Natl. Acad. Sci. USA, 69:2110-2114 (1972).
Cunningham, et al., Curr. Opin. Struct. Biol., 7:457-462 (1997).
Ferré-D'Arnaré, et al., Nature, 363:38-45 (1993).
Flanagan, et al., Annu. Rev. Neurosci., 21:309-345 (1998).
Fried, et al., Nucl. Acids Res., 9:6505-6525 (1981).
Graham, et al., Virology, 52:456-467 (1973).

(Continued)

Primary Examiner—Marianne P Allen
(74) Attorney, Agent, or Firm—Wolf, Greenfield & Sacks, P.C.

(57) ABSTRACT

The present invention provides a protein scaffold, such as an avian pancreatic polypeptide, that can be modified by substitution of two or more amino acid residues that are exposed on the alpha helix domain of the polypeptide when the polypeptide is in a tertiary form.

7 Claims, 16 Drawing Sheets

OTHER PUBLICATIONS

Hoogenboom, et al., Nucleic Acids Res., 19:4133-4137 (1991).
Jackson, et al., J. Am. Chem. Soc., 113:9391-9392 (1991).
Johnson, Mol. Cell. Biol., 13:6919-6930 (1993).
Keller, et al., J. Mol. Biol., 254:657-667 (1995).
Kemp, et al., J. Org. Chem., 56:6683-6697 (1991).
Kettleborough, et al., Eur. J. Immunol., 24:952-958 (1994).
Kouzarides, et al., Nature, 336:646-651 (1998).
Kussie, et al., Science, 274:948-953 (1996).
Li, et al., Biochemistry, 31:1245-1253 (1992).
Li, et al., Science, 270:1657-1660 (1995).
Ma, et al., Cell, 77:451-459 (1994).
Marks, et al., J. Mol. Biol., 222:581-597 (1991).
McCafferty, et al., Nature, 348:552-554 (1990).
Morii, et al., J. Am. Chem. Soc., 118:10011-10017 (1996).
Nygren, et al., Curr. Opin. Struct. Biol., 7:463-469 (1997).
O'Neil, et al., Science, 249:774-778 (1990).
Park, et al., J. Am. Chem. Soc., 118:4235-4239 (1996).
Persic, et al., Gene, 187:9-18 (1997).
Radhakrishnan, et al., Cell, 91:741-752 (1997).
Sattler, et al., Science, 275:983-986 (1997).
Sauder, et al., J. Gen. Virol., 77:991-996 (1996).
Schafmeister, et al., J. Am. Chem. Soc., 122:5891-5892 (2000).
Scott, et al., Proc. Natl. Acad. Sci., 81:4115-4119 (1984).
Segal, et al., Curr. Op. Chem. Biol., 4:34-39 (2000).
Shimizu, et al., EMBO J., 16:4689-4697 (1997).
Southern, et al., J. Mol. Appl. Genet., 1:327-341 (1982).
Southern, J. Mol. Biol., 98:503-517 (1975).
Suckow, et al., EMBO J., 12:1193-1200 (1993).
Takahashi, et al., Cell, 99:59-69 (1999).
Takayama, et al., Methods Mol. Biol., 69:171-184 (1997).
Tonan, et al., Biochemistry, 29:4424-4429 (1990).
Vita, et al., Biopolymers, 47:93-100 (1998).
Vita, et al., Proc. Natl. Acad. Sci. USA, 92:6404-6408 (1995).
Weiss, et al., Nature, 347:575-578 (1990).
Wigler, et al., Proc. Natl. Acad. Sci. USA, 76:1373-1376 (1979).
Zondlo, et al., J. Am. Chem. Soc., 121:6938-6939 (1999).

* cited by examiner

| SEQ ID NO. | | Sequence | # | Kd (nM) |
|---|---|---|---|---|
| SEQ ID NO.: 30 | BakLJB (20-36) | FVXRLLXYIXDXINR | | |
| SEQ ID NO.: 23 | 4100 | FVGRLLRYFGDEINR | 6 | 401 |
| SEQ ID NO.: 24 | 4101 | FVGRLLAYFGDCINR | 2 | 811 |
| SEQ ID NO.: 25 | 4099 | FVGRLLAYFGDTINR | 3 | 352 |
| SEQ ID NO.: 26 | 4102 | FVSRL-RYIADLINR | 2 | 3700 |
| SEQ ID NO.: 27 | | FVRRLLGYIDDIINR | 1 | |
| SEQ ID NO.: 28 | | FVLRLLWYIPDGINR | 1 | |
| SEQ ID NO.: 29 | | FVRRLLVYIWDQINR | 1 | |

Figure 1

Figure 4. Structures of (A) the PKA catalytic subunit bound to $PKI_{5-24}$[25] and (B) the natural product K252a and K252a-Δ.[26]

Figure 5. Design of PKA inhibitors. Residues that contribute significantly to PKA inhibition are in red; residues that contribute to aPP folding are in blue (α-helix) or yellow (PPII helix).

Figure 7
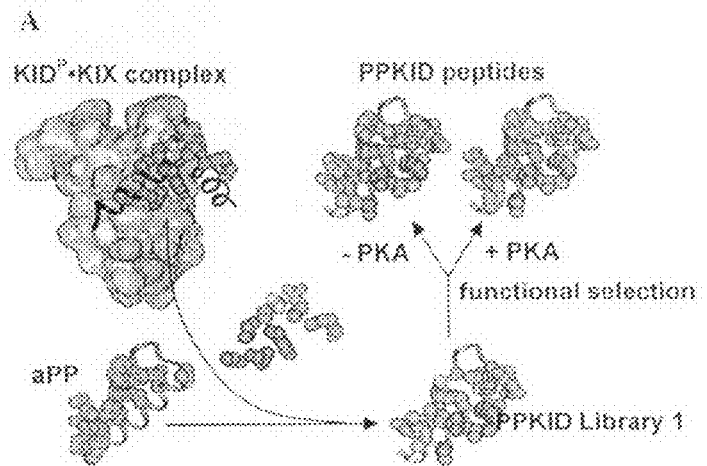
A
KID$^P$·KIX complex    PPKID peptides
                         − PKA      + PKA
                              functional selection
aPP                    PPKID Library 1
B
aPP       GPSQPTYPGDDAPVEDLIRFYNDLQQYLNVV    Helix B    SEQ ID NO.: 6
                           RRPSIKKILNDLSSDAP              SEQ ID NO.: 90
Library   GZSXXTXXGDDAPVPRLGFFYILLDLYLDAP              SEQ ID NO.: 79
C    Bcl-X$_L$·Bak      KIX$^P$·KID                       &
     complex            complex                    SEQ ID NO.: 67
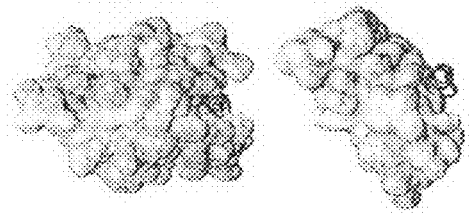

```
                          SEQUENCE LISTING

<160> NUMBER OF SEQ ID NOS: 95

<210> SEQ ID NO 1
    <211> LENGTH: 24
    <212> TYPE: DNA
    <213> ORGANISM: Artificial Sequence
    <220> FEATURE:
    <223> OTHER INFORMATION: Recognition site of hsCRE24 protein

<400> SEQUENCE: 1
agtggagatg acagctactc gtgc                                          24

<210> SEQ ID NO 2
    <211> LENGTH: 24
    <212> TYPE: DNA
    <213> ORGANISM: Artificial Sequence
    <220> FEATURE:
    <223> OTHER INFORMATION: Recognition site of hsCEBP24 protein

<400> SEQUENCE: 2
agtggagatt gcagctactc gtgc                                          24

<210> SEQ ID NO 3
    <211> LENGTH: 24
    <212> TYPE: DNA
    <213> ORGANISM: Artificial Sequence
    <220> FEATURE:
    <223> OTHER INFORMATION: Recognition site of CRE24 protein

<400> SEQUENCE: 3
agtggagatg acgtcatctc gtgc                                          24

<210> SEQ ID NO 4
    <211> LENGTH: 24
    <212> TYPE: DNA
    <213> ORGANISM: Artificial Sequence
    <220> FEATURE:
    <223> OTHER INFORMATION: Recognition site of CEBP24 protein

<400> SEQUENCE: 4
agtggagatt gcgcaatctc gtgc                                          24

<210> SEQ ID NO 5
    <211> LENGTH: 24
    <212> TYPE: DNA
    <213> ORGANISM: Artificial Sequence
    <220> FEATURE:
    <223> OTHER INFORMATION: Competitor site in recognition studies
```

```
<400> SEQUENCE: 5
agtggagtaa ggcctatctc gtgc                                            24

<210> SEQ ID NO 6
<211> LENGTH: 36
<212> TYPE: PRT
<213> ORGANISM: Artificial Sequence
<220> FEATURE:
<223> OTHER INFORMATION: Segment of avian pancreatic polypeptide

<400> SEQUENCE: 6
```

Gly Pro Ser Gln Pro Thr Tyr Pro Gly Asp Asp Ala Pro Val Glu Asp
 1               5                  10                  15

Leu Ile Arg Phe Tyr Asn Asp Leu Gln Gln Tyr Leu Asn Val Val Thr
            20                  25                  30

Arg His Arg Tyr
        35

```
<210> SEQ ID NO 7
<211> LENGTH: 27
<212> TYPE: PRT
<213> ORGANISM: Artificial Sequence
<220> FEATURE:
<223> OTHER INFORMATION: Segment of GCN4 protein

<400> SEQUENCE: 7
```

Asp Pro Ala Ala Leu Lys Arg Ala Arg Asn Thr Glu Ala Ala Arg Arg
 1               5                  10                  15

Ser Arg Ala Arg Lys Leu Gln Arg Met Lys Gln
            20                  25

```
<210> SEQ ID NO 8
<211> LENGTH: 39
<212> TYPE: PRT
<213> ORGANISM: Artificial Sequence
<220> FEATURE:
<223> OTHER INFORMATION: Pancreatic polypeptide basic region PPBR0

<400> SEQUENCE: 8
```

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Tyr Leu Ser Val Val Arg
            20                  25                  30

Lys Leu Gln Arg Met Lys Gln
        35

```
<210> SEQ ID NO 9
<211> LENGTH: 39
<212> TYPE: PRT
<213> ORGANISM: Artificial Sequence
<220> FEATURE:
<223> OTHER INFORMATION: Pancreatic polypeptide basic region PPBR10

<400> SEQUENCE: 9
```

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Tyr Leu Ser Arg Leu Arg
            20                  25                  30

Lys Ala Ala Arg Ala Ala Ala
        35

```
<210> SEQ ID NO 10
<211> LENGTH: 39
<212> TYPE: PRT
<213> ORGANISM: Artificial Sequence
<220> FEATURE:
<223> OTHER INFORMATION: Pancreatic polypeptide basic region PPBR11

<400> SEQUENCE: 10

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Arg Leu Ser Arg Leu Arg
            20                  25                  30

Lys Ala Ala Arg Ala Ala Ala
        35

<210> SEQ ID NO 11
<211> LENGTH: 39
<212> TYPE: PRT
<213> ORGANISM: Artificial Sequence
<220> FEATURE:
<223> OTHER INFORMATION: Pancreatic polypeptide basic region PPBR2

<400> SEQUENCE: 11

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Leu Gln Arg Met Lys Gln
        35

<210> SEQ ID NO 12
<211> LENGTH: 39
<212> TYPE: PRT
<213> ORGANISM: Artificial Sequence
<220> FEATURE:
<223> OTHER INFORMATION: Pancreatic polypeptide basic region PPBR4

<400> SEQUENCE: 12

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala Arg Ala Ala Ala
        35

<210> SEQ ID NO 13
<211> LENGTH: 27
<212> TYPE: PRT
<213> ORGANISM: Artificial Sequence
<220> FEATURE:
<223> OTHER INFORMATION: G27

<400> SEQUENCE: 13

Asp Pro Ala Ala Leu Lys Arg Ala Arg Asn Thr Glu Ala Ala Arg Arg
 1               5                  10                  15

Ser Arg Ala Arg Lys Leu Gln Arg Met Gln Cys
            20                  25

<210> SEQ ID NO 14
<211> LENGTH: 39
<212> TYPE: PRT
<213> ORGANISM: Artificial Sequence
<220> FEATURE:
<223> OTHER INFORMATION: Pancreatic polypeptide basic region PPBR4-delta
```

```
<400> SEQUENCE: 14

Gly Pro Ser Gln Pro Thr Tyr Pro Gly Asp Asp Ala Pro Val Glu Asp
 1               5                  10                  15

Leu Lys Arg Phe Arg Asn Thr Leu Ala Ala Arg Arg Ser Arg Leu Arg
            20                  25                  30

Lys Ala Ala Arg Ala Ala Ala
        35

<210> SEQ ID NO 15
<211> LENGTH: 35
<212> TYPE: PRT
<213> ORGANISM: Artificial Sequence
<220> FEATURE:
<223> OTHER INFORMATION: Variant pancreatic polypeptide basic region,
      Library A
<220> FEATURE:
<221> NAME/KEY: VARIANT
<222> LOCATION: 1, 4, 7
<223> OTHER INFORMATION: Xaa = Any Amino Acid

<400> SEQUENCE: 15

Xaa Pro Ser Xaa Pro Thr Xaa Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35

<210> SEQ ID NO 16
<211> LENGTH: 35
<212> TYPE: PRT
<213> ORGANISM: Artificial Sequence
<220> FEATURE:
<223> OTHER INFORMATION: Variant pancreatic polypeptide basic region,
      Library B
<220> FEATURE:
<221> NAME/KEY: VARIANT
<222> LOCATION: 2, 4, 5, 7
<223> OTHER INFORMATION: Xaa = Any Amino Acid

<400> SEQUENCE: 16

Gly Xaa Ser Xaa Xaa Thr Xaa Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35

<210> SEQ ID NO 17
<211> LENGTH: 35
<212> TYPE: PRT
<213> ORGANISM: Artificial Sequence
<220> FEATURE:
<223> OTHER INFORMATION: Variant pancreatic polypeptide basic region,
      Lib.B, clone 007

<400> SEQUENCE: 17

Gly Gly Ser Arg Ala Thr Met Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35
```

<210> SEQ ID NO 18
<211> LENGTH: 35
<212> TYPE: PRT
<213> ORGANISM: Artificial Sequence
<220> FEATURE:
<223> OTHER INFORMATION: Variant pancreatic polypeptide basic region,
      Lib. B, clone 012

<400> SEQUENCE: 18

Gly Val Ser Val Gly Thr Arg Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35

<210> SEQ ID NO 19
<211> LENGTH: 35
<212> TYPE: PRT
<213> ORGANISM: Artificial Sequence
<220> FEATURE:
<223> OTHER INFORMATION: Variant pancreatic polypeptide basic region,
      Lib. B, clone 11

<400> SEQUENCE: 19

Gly Thr Ser Thr Gly Thr Arg Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala
        35

<210> SEQ ID NO 20
<211> LENGTH: 35
<212> TYPE: PRT
<213> ORGANISM: Artificial Sequence
<220> FEATURE:
<223> OTHER INFORMATION: Variant pancreatic polypeptide basic region,
      Lib. B, clone 013

<400> SEQUENCE: 20

Gly Val Ser Ser Val Thr Trp Pro Gly Asp Asp Ala Pro Val Glu Asp
 1               5                  10                  15

Leu Arg Lys Phe Arg Asn Thr Leu Ala Ala Arg Arg Ser Arg Ala Arg
            20                  25                  30

Lys Ala Ala
        35

<210> SEQ ID NO 21
<211> LENGTH: 35
<212> TYPE: PRT
<213> ORGANISM: Artificial Sequence
<220> FEATURE:
<223> OTHER INFORMATION: Variant pancreatic polypeptide basic region,
      Lib. B, clone 009

<400> SEQUENCE: 21

Gly Pro Ser Glu Gly Thr Glu Pro Gly Asp Asp Ala Pro Val Glu Asp
 1               5                  10                  15

Leu Lys Arg Phe Arg Asn Thr Leu Ala Ala Arg Arg Ser Arg Ala Arg
            20                  25                  30

Lys Ala Ala

```
<210> SEQ ID NO 22
<211> LENGTH: 35
<212> TYPE: PRT
<213> ORGANISM: Artificial Sequence
<220> FEATURE:
<223> OTHER INFORMATION: Variant pancreatic polypeptide basic region,
      Lib. B, clone 016

<400> SEQUENCE: 22

Gly Arg Ser His Gln Thr Trp Pro Gly Asp Asp Ala Pro Val Glu Asp
1               5                   10                  15

Leu Lys Arg Phe Arg Asn Thr Leu Ala Ala Arg Arg Ser Arg Ala Arg
            20                  25                  30

Lys Ala Ala
        35

<210> SEQ ID NO 23
<211> LENGTH: 15
<212> TYPE: PRT
<213> ORGANISM: Artificial Sequence
<220> FEATURE:
<223> OTHER INFORMATION: Peptide 4100 isolated from BakLib

<400> SEQUENCE: 23

Phe Val Gly Arg Leu Leu Arg Tyr Phe Gly Asp Glu Ile Asn Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Peptide 4101 isolated from BakLib

<400> SEQUENCE: 24

Phe Val Gly Arg Leu Leu Ala Tyr Phe Gly Asp Asp Ile Asn Arg
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Peptide 4099 isolated from BakLib

<400> SEQUENCE: 25

Phe Val Gly Arg Leu Leu Ala Tyr Phe Gly Asp Thr Ile Asn Arg
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Peptide 4102 isolated from BakLib

<400> SEQUENCE: 26

Phe Val Ser Arg Leu Arg Tyr Ile Ala Asp Leu Ile Asn Arg
1               5                   10

<210> SEQ ID NO 27
<211> LENGTH: 15
<212> TYPE: PRT
<213> ORGANISM: Artificial Sequence
```

```
<220> FEATURE:
<223> OTHER INFORMATION: Peptide isolated from BakLib

<400> SEQUENCE: 27

Phe Val Arg Arg Leu Leu Gly Tyr Ile Asp Asp Ile Ile Asn Arg
  1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Peptide isolated from BakLib

<400> SEQUENCE: 28

Phe Val Leu Arg Leu Leu Trp Tyr Ile Pro Asp Gly Ile Asn Arg
  1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Peptide isolated from BakLib

<400> SEQUENCE: 29

Phe Val Arg Arg Leu Leu Val Tyr Ile Trp Asp Asp Ile Asn Arg
  1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Consensus sequence for peptides isolated from
      BakLib
<220> FEATURE:
<221> NAME/KEY: VARIANT
<222> LOCATION: 3, 7, 10, 12
<223> OTHER INFORMATION: Xaa = Any Amino Acid

<400> SEQUENCE: 30

Phe Val Xaa Arg Leu Leu Xaa Tyr Ile Xaa Asp Xaa Ile Asn Arg
  1               5                  10                  15

<210> SEQ ID NO 31
<211> LENGTH: 11
<212> TYPE: PRT
<213> ORGANISM: Artificial Sequence
<220> FEATURE:
<223> OTHER INFORMATION: p53 miniature protein p53AD

<400> SEQUENCE: 31

Glu Thr Phe Ser Asp Leu Trp Lys Leu Leu Pro
  1               5                  10

<210> SEQ ID NO 32
<211> LENGTH: 31
<212> TYPE: PRT
<213> ORGANISM: Artificial Sequence
<220> FEATURE:
<223> OTHER INFORMATION: p53 miniature protein, Library 1 consensus
      sequence
<220> FEATURE:
<221> NAME/KEY: VARIANT
<222> LOCATION: 21, 23, 25, 30, 31
<223> OTHER INFORMATION: Xaa = Any Amino Acid

<400> SEQUENCE: 32
```

Gly Pro Ser Gln Pro Thr Tyr Pro Gly Asp Asp Ala Pro Val Glu Asp
1               5                   10                  15

Leu Ile Arg Phe Xaa Phe Xaa Leu Xaa Trp Tyr Leu Leu Xaa Xaa
            20                  25                  30

<210> SEQ ID NO 33
<211> LENGTH: 15
<212> TYPE: PRT
<213> ORGANISM: Artificial Sequence
<220> FEATURE:
<223> OTHER INFORMATION: p53 miniature protein, Lib. 1, clone p3254

<400> SEQUENCE: 33

Leu Ile Arg Phe Gln Phe Ala Leu Arg Trp Tyr Leu Leu Pro Met
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: p53 miniature protein, Lib. 1, clone p3255

<400> SEQUENCE: 34

Leu Ile Arg Phe Gln Phe Gly Leu Gly Trp Tyr Leu Leu Ala Met
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: p53 miniature protein, Lib. 1, clone p3548

<400> SEQUENCE: 35

Leu Ile Arg Phe Gln Phe Pro Leu Arg Trp Tyr Leu Leu Trp Ala
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: p53 miniature protein, Lib. 1, clone p3559

<400> SEQUENCE: 36

Leu Ile Arg Phe Lys Phe Leu Leu Gln Trp Tyr Leu Leu Ala Leu
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: p53 miniature protein, Lib. 1, clone p3257

<400> SEQUENCE: 37

Leu Ile Arg Phe Ser Phe Ala Leu Gln Trp Tyr Leu Leu Gly Glu
1               5                   10                  15

<210> SEQ ID NO 38
<211> LENGTH: 31
<212> TYPE: PRT
<213> ORGANISM: Artificial Sequence
<220> FEATURE:
<223> OTHER INFORMATION: Universal library 1 consensus sequence for pancreatic peptide basic region
<220> FEATURE:
<221> NAME/KEY: VARIANT
<222> LOCATION: 21, 22, 23, 25, 26, 29
<223> OTHER INFORMATION: Xaa = Any Amino Acid

<400> SEQUENCE: 38

Gly Pro Ser Gln Pro Thr Tyr Pro Gly Asp Asp Ala Pro Val Glu Asp
 1               5                  10                  15

Leu Ile Arg Phe Xaa Xaa Xaa Leu Xaa Xaa Tyr Leu Xaa Val Val
            20                  25                  30

<210> SEQ ID NO 39
<211> LENGTH: 142
<212> TYPE: DNA
<213> ORGANISM: Artificial Sequence
<220> FEATURE:
<223> OTHER INFORMATION: Cloning primer APP.TS

<400> SEQUENCE: 39
ctatgcggcc cagccggccg gtccgtccca gccgacctac ccgggtgacg acgcaccggt      60
tgaagatctg atccgtttct acaacgacct gcagcagtac ctgaacgttg ttacccgtca    120
ccgttacgcg gccgcaggtg cg                                              142

<210> SEQ ID NO 40
<211> LENGTH: 87
<212> TYPE: DNA
<213> ORGANISM: Artificial Sequence
<220> FEATURE:
<223> OTHER INFORMATION: Cloning primer APP.BS

<400> SEQUENCE: 40
ctatgcggcc cagccggccg gtccgtccca gccgacctac ccgggtgac gacgcaccgg      60 ttgaagatct gatccgtttc tacaacg                                         87

<210> SEQ ID NO 41
<211> LENGTH: 21
<212> TYPE: DNA
<213> ORGANISM: Artificial Sequence
<220> FEATURE:
<223> OTHER INFORMATION: PCR primer

<400> SEQUENCE: 41
ctatgcggcc cagccggccg g                                               21

<210> SEQ ID NO 42
<211> LENGTH: 21
<212> TYPE: DNA
<213> ORGANISM: Artificial Sequence
<220> FEATURE:
<223> OTHER INFORMATION: PCR primer

<400> SEQUENCE: 42
cgcacctgcg gccgcgtaac g                                               21

<210> SEQ ID NO 43
<211> LENGTH: 83
<212> TYPE: DNA
<213> ORGANISM: Artificial Sequence
<220> FEATURE:
<223> OTHER INFORMATION: Cloning primer PPBR4TS

<400> SEQUENCE: 43
gatctgaagc gctttcgtaa caccctggct gcgcgccgtt cccgtgcacg taaagctgca     60

```
cgtgctgcag ctggtggttg cgc                                              83
```

<210> SEQ ID NO 44
<211> LENGTH: 103
<212> TYPE: DNA
<213> ORGANISM: Artificial Sequence
<220> FEATURE:
<223> OTHER INFORMATION: Cloning primer PPBR4BS

<400> SEQUENCE: 44

```
cgcacctgcg gccgcgcaac caccagctgc agcacgtgca gctttacgtg cacgggaacg     60
gcgcgcagcc aggtgttac gaaagcgctt cagatcttca acc                      103
```

<210> SEQ ID NO 45
<211> LENGTH: 96
<212> TYPE: DNA
<213> ORGANISM: Artificial Sequence
<220> FEATURE:
<223> OTHER INFORMATION: Oligonucleotide for constructing library
<220> FEATURE:
<221> NAME/KEY: misc_feature
<222> LOCATION: 40, 41, 52, 53, 61, 62, 67, 68
<223> OTHER INFORMATION: n = A,T,C or G

<400> SEQUENCE: 45

```
ggtgacgacg caccggttga agatctgatc cgctttgttn nscgtctgct gnnstacatc     60
nnsgacnnsa tcaaccgtcg tgcggccgca ggtgcg                              96
```

<210> SEQ ID NO 46
<211> LENGTH: 21
<212> TYPE: DNA
<213> ORGANISM: Artificial Sequence
<220> FEATURE:
<223> OTHER INFORMATION: Oligonucleotide for constructing library

<400> SEQUENCE: 46

```
cgcacctgcg gcggcacgac g                                                21
```

<210> SEQ ID NO 47
<211> LENGTH: 41
<212> TYPE: PRT
<213> ORGANISM: Artificial Sequence
<220> FEATURE:
<223> OTHER INFORMATION: PPEBP1, polyproline-enhancer binding protein

<400> SEQUENCE: 47

```
Gly Pro Ser Gln Pro Thr Tyr Pro Gly Asp Asp Ala Pro Val Tyr Asp
1               5                   10                  15

Leu Ile Arg Phe Arg Asn Asn Leu Ala Val Arg Lys Ser Arg Val Lys
            20                  25                  30

Ala Lys Arg Arg Asn Gln Gly Gly Cys
        35                  40
```

<210> SEQ ID NO 48
<211> LENGTH: 41
<212> TYPE: PRT
<213> ORGANISM: Artificial Sequence
<220> FEATURE:
<223> OTHER INFORMATION: PPEBP2, polyproline-enhancer binding protein

<400> SEQUENCE: 48

```
Gly Pro Ser Gln Pro Thr Tyr Pro Gly Asp Asp Ala Pro Glu Tyr Arg
1               5                   10                  15
```

```
Leu Arg Arg Phe Arg Asn Asn Leu Ala Val Arg Lys Ser Arg Val Lys
            20                  25                  30

Ala Lys Arg Arg Asn Gln Gly Gly Cys
            35                  40

<210> SEQ ID NO 49
<211> LENGTH: 41
<212> TYPE: PRT
<213> ORGANISM: Artificial Sequence
<220> FEATURE:
<223> OTHER INFORMATION: PPEBP3, polyproline-enhancer binding protein

<400> SEQUENCE: 49

Gly Pro Ser Gln Pro Thr Tyr Pro Gly Asp Asp Ala Pro Val Tyr Asp
  1               5                  10                  15

Leu Ile Arg Phe Arg Asn Asn Leu Ala Val Tyr Leu Ser Val Val Lys
            20                  25                  30

Ala Lys Arg Arg Asn Gln Gly Gly Cys
            35                  40

<210> SEQ ID NO 50
<211> LENGTH: 41
<212> TYPE: PRT
<213> ORGANISM: Artificial Sequence
<220> FEATURE:
<223> OTHER INFORMATION: PPEBP4, polyproline-enhancer binding protein

<400> SEQUENCE: 50

Gly Pro Ser Gln Pro Thr Tyr Pro Gly Asp Asp Ala Pro Val Ala Arg
  1               5                  10                  15

Leu Arg Arg Phe Ala Ala Thr Leu Ala Ala Ala Ser Ala Ala Lys
            20                  25                  30

Ala Lys Arg Arg Asn Gln Gly Gly Cys
            35                  40

<210> SEQ ID NO 51
<211> LENGTH: 28
<212> TYPE: PRT
<213> ORGANISM: Artificial Sequence
<220> FEATURE:
<223> OTHER INFORMATION: EBP1, polyproline-enhancer binding protein

<400> SEQUENCE: 51

Val Tyr Asp Leu Ile Arg Phe Arg Asn Asn Leu Ala Val Arg Lys Ser
  1               5                  10                  15

Val Val Lys Ala Lys Arg Arg Asn Gln Gly Gly Cys
            20                  25

<210> SEQ ID NO 52
<211> LENGTH: 41
<212> TYPE: PRT
<213> ORGANISM: Artificial Sequence
<220> FEATURE:
<223> OTHER INFORMATION: Delta-PPEBP1, polyproline-enhancer binding
      protein

<400> SEQUENCE: 52

Gly Pro Ser Trp Pro Thr Tyr Pro Gly Asp Asp Ala Pro Val Tyr Asp
  1               5                  10                  15

Leu Ile Arg Phe Arg Asn Asn Leu Ala Val Arg Lys Ser Val Val Lys
            20                  25                  30

Ala Lys Arg Arg Asn Gln Gly Gly Cys
            35                  40
```

<210> SEQ ID NO 53
<211> LENGTH: 34
<212> TYPE: PRT
<213> ORGANISM: Artificial Sequence
<220> FEATURE:
<223> OTHER INFORMATION: PPMyo1, MyoD peptide

<400> SEQUENCE: 53

Gly Pro Ser Gln Pro Thr Tyr Pro Gly Asp Asp Ala Pro Val Glu Asp
1               5                   10                  15

Leu Arg Arg Phe Tyr Asp Thr Leu Arg Glu Arg Arg Arg Val Val Gly
            20                  25                  30

Gly Cys

<210> SEQ ID NO 54
<211> LENGTH: 34
<212> TYPE: PRT
<213> ORGANISM: Artificial Sequence
<220> FEATURE:
<223> OTHER INFORMATION: PPMyo2, MyoD peptide

<400> SEQUENCE: 54

Gly Pro Ser Gln Pro Thr Tyr Pro Gly Asp Asp Ala Pro Val Glu Asp
1               5                   10                  15

Leu Arg Arg Phe Tyr Asp Thr Leu Arg Glu Tyr Leu Arg Val Val Gly
            20                  25                  30

Gly Cys

<210> SEQ ID NO 55
<211> LENGTH: 34
<212> TYPE: PRT
<213> ORGANISM: Artificial Sequence
<220> FEATURE:
<223> OTHER INFORMATION: PPMyo3, MyoD peptide

<400> SEQUENCE: 55

Gly Pro Ser Gln Pro Thr Tyr Pro Gly Asp Asp Ala Pro Val Glu Asp
1               5                   10                  15

Leu Arg Arg Phe Tyr Asp Thr Leu Arg Glu Tyr Arg Arg Val Val Gly
            20                  25                  30

Gly Cys

<210> SEQ ID NO 56
<211> LENGTH: 34
<212> TYPE: PRT
<213> ORGANISM: Artificial Sequence
<220> FEATURE:
<223> OTHER INFORMATION: PPMyo4, MyoD peptide

<400> SEQUENCE: 56

Gly Pro Ser Gln Pro Thr Tyr Pro Gly Asp Asp Ala Pro Val Glu Asp
1               5                   10                  15

Leu Arg Arg Phe Tyr Asp Thr Leu Arg Glu Arg Leu Arg Val Val Gly
            20                  25                  30

Gly Cys

<210> SEQ ID NO 57
<211> LENGTH: 31
<212> TYPE: PRT
<213> ORGANISM: Artificial Sequence
<220> FEATURE:

-continued

```
<223> OTHER INFORMATION: PPeng1, Q50K engrailed variant peptide

<400> SEQUENCE: 57

Gly Pro Ser Gln Pro Thr Tyr Pro Gly Asp Asp Ala Pro Lys Ile Trp
 1               5                  10                  15

Leu Lys Asn Phe Arg Asp Lys Leu Lys Lys Tyr Leu Asn Val Val
            20                  25                  30

<210> SEQ ID NO 58
<211> LENGTH: 31
<212> TYPE: PRT
<213> ORGANISM: Artificial Sequence
<220> FEATURE:
<223> OTHER INFORMATION: PPeng2, Q50K engrailed variant peptide

<400> SEQUENCE: 58

Gly Pro Ser Gln Pro Thr Tyr Pro Gly Asp Asp Ala Pro Lys Ile Trp
 1               5                  10                  15

Leu Lys Asn Phe Arg Ala Lys Leu Lys Lys Tyr Leu Asn Val Val
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: PPeng3, Q50K engrailed variant peptide

<400> SEQUENCE: 59

Gly Pro Ser Gln Pro Thr Tyr Pro Gly Asp Asp Ala Pro Val Glu Asp
 1               5                  10                  15

Leu Lys Ile Phe Tyr Lys Asn Leu Arg Gln Tyr Leu Lys Val Val
            20                  25                  30

<210> SEQ ID NO 60
<211> LENGTH: 31
<212> TYPE: PRT
<213> ORGANISM: Artificial Sequence
<220> FEATURE:
<223> OTHER INFORMATION: PPeng4, Q50K engrailed variant peptide

<400> SEQUENCE: 60

Gly Pro Ser Gln Pro Thr Tyr Pro Gly Asp Asp Ala Pro Val Glu Asp
 1               5                  10                  15

Leu Lys Ile Phe Phe Lys Asn Leu Arg Ala Lys Leu Lys Lys Val
            20                  25                  30

<210> SEQ ID NO 61
<211> LENGTH: 43
<212> TYPE: PRT
<213> ORGANISM: Artificial Sequence
<220> FEATURE:
<223> OTHER INFORMATION: PPFos1, Fos peptide

<400> SEQUENCE: 61

Gly Pro Ser Gln Pro Thr Tyr Pro Gly Asp Asp Ala Pro Val Leu Glu
 1               5                  10                  15

Leu Glu Asn Phe Tyr Leu Asn Leu Glu Ile Tyr Leu Leu Val Val Glu
            20                  25                  30

Lys Glu Lys Leu Glu Phe Ile Leu Ala Ala Tyr
            35                  40

<210> SEQ ID NO 62
```

<210> SEQ ID NO 62
<211> LENGTH: 43
<212> TYPE: PRT
<213> ORGANISM: Artificial Sequence
<220> FEATURE:
<223> OTHER INFORMATION: PPFos2, Fos peptide

<400> SEQUENCE: 62

Gly Pro Ser Gln Pro Thr Tyr Pro Gly Asp Asp Ala Pro Val Leu Glu
1               5                   10                  15

Leu Glu Lys Phe Tyr Leu Asn Leu Glu Ile Tyr Leu Val Val Glu
            20                  25                  30

Lys Glu Lys Leu Glu Phe Ile Leu Ala Ala Tyr
        35                  40

<210> SEQ ID NO 63
<211> LENGTH: 50
<212> TYPE: PRT
<213> ORGANISM: Artificial Sequence
<220> FEATURE:
<223> OTHER INFORMATION: PPFos3, Fos peptide

<400> SEQUENCE: 63

Gly Pro Ser Gln Pro Thr Tyr Pro Gly Asp Asp Ala Pro Val Leu Asp
1               5                   10                  15

Leu Glu Thr Phe Tyr Leu Glu Leu Glu Asn Tyr Leu Leu Val Val Glu
            20                  25                  30

Ile Ala Asn Leu Leu Lys Glu Lys Glu Lys Leu Glu Phe Ile Leu Ala
        35                  40                  45

Ala Tyr
    50

<210> SEQ ID NO 64
<211> LENGTH: 50
<212> TYPE: PRT
<213> ORGANISM: Artificial Sequence
<220> FEATURE:
<223> OTHER INFORMATION: PPFos4, Fos peptide

<400> SEQUENCE: 64

Gly Pro Ser Gln Pro Thr Tyr Pro Gly Asp Asp Ala Pro Val Leu Asp
1               5                   10                  15

Leu Glu Thr Phe Tyr Leu Glu Leu Glu Lys Tyr Leu Leu Val Val Glu
            20                  25                  30

Ile Ala Asn Leu Leu Lys Glu Lys Glu Lys Leu Glu Phe Ile Leu Ala
        35                  40                  45

Ala Tyr
    50

<210> SEQ ID NO 65
<211> LENGTH: 5
<212> TYPE: DNA
<213> ORGANISM: Artificial Sequence
<220> FEATURE:
<223> OTHER INFORMATION: CRE half-site promoter

<400> SEQUENCE: 65 atgac                                                              5

<210> SEQ ID NO 66
<211> LENGTH: 5
<212> TYPE: DNA
<213> ORGANISM: Artificial Sequence
<220> FEATURE:

<223> OTHER INFORMATION: C/EBP half-site promoter

<400> SEQUENCE: 66 attgc                                                                    5

<210> SEQ ID NO 67
<211> LENGTH: 10
<212> TYPE: DNA
<213> ORGANISM: Artificial Sequence
<220> FEATURE:
<223> OTHER INFORMATION: C/EBP protein binding site

<400> SEQUENCE: 67
attgcgcaat                                                              10

<210> SEQ ID NO 68
<211> LENGTH: 10
<212> TYPE: DNA
<213> ORGANISM: Artificial Sequence
<220> FEATURE:
<223> OTHER INFORMATION: CRE protein binding site

<400> SEQUENCE: 68
atgacgtcat                                                              10

<210> SEQ ID NO 69
<211> LENGTH: 31
<212> TYPE: PRT
<213> ORGANISM: Artificial Sequence
<220> FEATURE:
<223> OTHER INFORMATION: Transcription-activating miniature protein,
      consensus sequence
<220> FEATURE:
<221> NAME/KEY: VARIANT
<222> LOCATION: 2, 4, 5, 7, 8
<223> OTHER INFORMATION: Xaa = Any Amino Acid

<400> SEQUENCE: 69

Gly Xaa Ser Xaa Xaa Thr Xaa Xaa Gly Asp Asp Ala Pro Val Arg Arg
 1               5                  10                  15

Leu Ser Phe Phe Tyr Ile Leu Leu Asp Leu Tyr Leu Asp Ala Pro
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: PPKID1, transcription-activating miniature
      protein

<400> SEQUENCE: 70

Gly Ala Ser Asp Met Thr Tyr Trp Gly Asp Asp Ala Pro Val Arg Arg
 1               5                  10                  15

Leu Ser Phe Phe Tyr Ile Leu Leu Asp Leu Tyr Leu Asp Ala Pro
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: PPKID2, transcription-activating miniature
      protein

<400> SEQUENCE: 71

```
Gly Met Ser Arg Val Thr Pro Gly Gly Asp Asp Ala Pro Val Arg Arg
1               5                   10                  15

Leu Ser Phe Phe Tyr Ile Leu Arg Asp Leu Tyr Leu Asp Ala Pro
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: PPKID3, transcription-activating miniature
      protein

<400> SEQUENCE: 72

Gly Ala Ser Pro His Thr Ser Ser Gly Asp Asp Ala Pro Val Arg Arg
1               5                   10                  15

Leu Ser Phe Phe Asp Ile Leu Leu Asp Leu Tyr Leu Asp Ala Pro
            20                  25                  30

<210> SEQ ID NO 73
<211> LENGTH: 16
<212> TYPE: PRT
<213> ORGANISM: Artificial Sequence
<220> FEATURE:
<223> OTHER INFORMATION: BH3 domain of Bak peptide

<400> SEQUENCE: 73

Gly Gln Val Gly Arg Gln Leu Ala Ile Ile Gly Asp Asp Ile Asn Arg
1               5                   10                  15

<210> SEQ ID NO 74
<211> LENGTH: 21
<212> TYPE: PRT
<213> ORGANISM: Artificial Sequence
<220> FEATURE:
<223> OTHER INFORMATION: PKA binding peptide sequence

<400> SEQUENCE: 74

Thr Thr Tyr Ala Asp Phe Ile Ala Ser Gly Arg Thr Gly Arg Arg Asn
1               5                   10                  15

Ala Ile His Asp Cys
            20

<210> SEQ ID NO 75
<211> LENGTH: 44
<212> TYPE: PRT
<213> ORGANISM: Artificial Sequence
<220> FEATURE:
<223> OTHER INFORMATION: PKA binding peptide sequence

<400> SEQUENCE: 75

Gly Pro Ser Gln Pro Thr Tyr Pro Gly Asp Asp Ala Pro Val Glu Asp
1               5                   10                  15

Leu Ile Arg Phe Tyr Asn Asp Leu Thr Tyr Tyr Leu Phe Val Val Ser
            20                  25                  30

Gly Arg Thr Gly Arg Arg Asn Ala Ile His Asp Cys
        35                  40

<210> SEQ ID NO 76
<211> LENGTH: 43
<212> TYPE: PRT
<213> ORGANISM: Artificial Sequence
<220> FEATURE:
<223> OTHER INFORMATION: PKA binding peptide sequence
```

```
<400> SEQUENCE: 76

Gly Pro Ser Gln Pro Thr Tyr Pro Gly Asp Asp Ala Pro Val Glu Asp
1               5                   10                  15

Leu Ile Arg Phe Tyr Asn Asp Leu Thr Tyr Tyr Leu Phe Val Val Ser
            20                  25                  30

Gly Arg Thr Gly Arg Arg Asn Cys Ile His Asp
        35                  40

<210> SEQ ID NO 77
<211> LENGTH: 20
<212> TYPE: PRT
<213> ORGANISM: Artificial Sequence
<220> FEATURE:
<223> OTHER INFORMATION: PKA binding peptide sequence

<400> SEQUENCE: 77

Thr Thr Tyr Ala Asp Phe Ile Ala Ser Gly Arg Thr Gly Arg Arg Asn
1               5                   10                  15

Cys Ile His Asp
            20

<210> SEQ ID NO 78
<211> LENGTH: 40
<212> TYPE: PRT
<213> ORGANISM: Artificial Sequence
<220> FEATURE:
<223> OTHER INFORMATION: PKA binding peptide sequence

<400> SEQUENCE: 78

Gly Pro Ser Gln Pro Thr Tyr Pro Gly Asp Asp Ala Pro Val Glu Asp
1               5                   10                  15

Leu Ile Arg Phe Thr Tyr Ala Leu Phe Ile Tyr Leu Gly Val Val Gly
            20                  25                  30

Arg Arg Asn Ala Ile His Asp Cys
        35                  40

<210> SEQ ID NO 79
<211> LENGTH: 31
<212> TYPE: PRT
<213> ORGANISM: Artificial Sequence
<220> FEATURE:
<223> OTHER INFORMATION: PPKID library consensus peptide sequence
<220> FEATURE:
<221> NAME/KEY: VARIANT
<222> LOCATION: 2, 4, 5, 7, 8
<223> OTHER INFORMATION: Xaa = Any Amino Acid

<400> SEQUENCE: 79

Gly Xaa Ser Xaa Xaa Thr Xaa Xaa Gly Asp Asp Ala Pro Val Arg Arg
1               5                   10                  15

Leu Ser Phe Phe Tyr Ile Leu Leu Asp Leu Tyr Leu Asp Ala Pro
            20                  25                  30

<210> SEQ ID NO 80
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 80

Gly Ala Ser Asp Met Thr Tyr Trp Gly Asp Asp Ala Pro Val Arg Arg
1               5                   10                  15
```

Leu Ser Phe Phe Tyr Ile Leu Leu Asp Leu Tyr Leu Asp Ala Pro Gly
            20                  25                  30

Val Cys

<210> SEQ ID NO 81
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 81

Gly Met Ser Arg Val Thr Pro Gly Gly Asp Asp Ala Pro Val Arg Arg
1               5                   10                  15

Leu Ser Phe Phe Tyr Ile Leu Arg Asp Leu Tyr Leu Asp Ala Pro Gly
            20                  25                  30

Val Cys

<210> SEQ ID NO 82
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 82

Gly Ala Ser Pro His Thr Ser Ser Gly Asp Asp Ala Pro Val Arg Arg
1               5                   10                  15

Leu Ser Phe Phe Asp Ile Leu Leu Asp Leu Tyr Leu Asp Ala Pro Gly
            20                  25                  30

Val Cys

<210> SEQ ID NO 83
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 83

Gly Pro Ser Gln Pro Thr Tyr Pro Gly Asp Asp Ala Pro Val Arg Arg
1               5                   10                  15

Leu Ser Phe Phe Tyr Ile Leu Leu Asp Leu Tyr Leu Asp Ala Pro Gly
            20                  25                  30

Val Cys

<210> SEQ ID NO 84
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 84

Gly Leu Ser Trp Pro Thr Tyr His Gly Asp Asp Ala Pro Val Arg Arg
1               5                   10                  15

Leu Ser Phe Phe Tyr Ile Leu Leu Asp Leu Tyr Leu Asp Ala Pro Gly
            20                  25                  30

Val Cys

<210> SEQ ID NO 85

```
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 85

Gly Ile Ser Trp Pro Thr Phe Glu Gly Asp Asp Ala Pro Val Arg Arg
 1               5                  10                  15

Leu Ser Phe Phe Tyr Ile Leu Leu Asp Leu Tyr Leu Asp Ala Pro Gly
            20                  25                  30

Val Cys

<210> SEQ ID NO 86
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 86

Gly Ile Ser Trp Pro Thr Phe Glu Gly Asp Asp Ala Pro Val Arg Arg
 1               5                  10                  15

Leu Glu Phe Phe Tyr Ile Leu Leu Asp Leu Tyr Leu Asp Ala Pro Gly
            20                  25                  30

Val Cys

<210> SEQ ID NO 87
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 87

Gly Leu Ser Pro Tyr Thr Glu Trp Gly Asp Asp Ala Pro Val Arg Arg
 1               5                  10                  15

Leu Ser Phe Phe Tyr Ile Leu Leu Asp Leu Tyr Leu Asp Ala Pro Gly
            20                  25                  30

Val Cys

<210> SEQ ID NO 88
<211> LENGTH: 34
<212> TYPE: PRT
<213> ORGANISM: Artificial Sequence
<220> FEATURE:
<223> OTHER INFORMATION: CBP KIX binding peptide sequence

<400> SEQUENCE: 88

Gly Leu Ser Trp Lys Thr Asp Pro Gly Asp Asp Ala Pro Val Arg Arg
 1               5                  10                  15

Leu Ser Phe Phe Tyr Ile Leu Leu Asp Leu Tyr Leu Asp Ala Pro Gly
            20                  25                  30

Val Cys

<210> SEQ ID NO 89
<211> LENGTH: 31
<212> TYPE: PRT
<213> ORGANISM: Artificial Sequence
<220> FEATURE:
<223> OTHER INFORMATION: CBP KIX binding peptide sequence

<400> SEQUENCE: 89
```

-continued

```
Thr Asp Ser Gln Lys Arg Arg Glu Ile Leu Ser Arg Arg Pro Ser Tyr
1               5                   10                  15

Arg Lys Ile Leu Asn Asp Leu Ser Ser Asp Ala Pro Gly Val Cys
            20                  25                  30

<210> SEQ ID NO 90
<211> LENGTH: 20
<212> TYPE: PRT
<213> ORGANISM: Artificial Sequence
<220> FEATURE:
<223> OTHER INFORMATION: CBP KIX binding peptide sequence

<400> SEQUENCE: 90

Arg Arg Pro Ser Tyr Arg Lys Ile Leu Asn Asp Leu Ser Ser Asp Ala
1               5                   10                  15

Pro Gly Val Cys
            20

<210> SEQ ID NO 91
<211> LENGTH: 20
<212> TYPE: PRT
<213> ORGANISM: Artificial Sequence
<220> FEATURE:
<223> OTHER INFORMATION: CBP KIX binding peptide sequence

<400> SEQUENCE: 91

Arg Arg Leu Ser Phe Phe Tyr Ile Leu Leu Asp Leu Tyr Leu Asp Ala
1               5                   10                  15

Pro Gly Val Cys
            20

<210> SEQ ID NO 92
<211> LENGTH: 38
<212> TYPE: DNA
<213> ORGANISM: Unknown
<220> FEATURE:
<223> OTHER INFORMATION: oligonucleotide primer sequence

<400> SEQUENCE: 92
gccgcgcggc agccatatgg gtgttcgaaa agcctggc                           38

<210> SEQ ID NO 93
<211> LENGTH: 40
<212> TYPE: DNA
<213> ORGANISM: Unknown
<220> FEATURE:
<223> OTHER INFORMATION: oligonucleotide primer sequence

<400> SEQUENCE: 93
ccaggccgct gcggatcctc atcataaacg tgacctccgc                         40

<210> SEQ ID NO 94
<211> LENGTH: 94
<212> TYPE: DNA
<213> ORGANISM: Unknown
<220> FEATURE:
<223> OTHER INFORMATION: oligonucleotide primer sequence

<400> SEQUENCE: 94
tgttcctttc tatgcaccgg ttcgtctctg tccttcttct acatcctgct ggacctgtac   60
ctggacgcac cggcggccgc aggtgcgccg ggcc                               94

<210> SEQ ID NO 95
```

```
<211> LENGTH: 83
<212> TYPE: DNA
<213> ORGANISM: Unknown
<220> FEATURE:
<223> OTHER INFORMATION: oligonucleotide primer sequence
<220> FEATURE:
<221> NAME/KEY: misc_feature
<222> LOCATION: 31, 32, 37, 38, 40, 41, 46, 47, 49, 50
<223> OTHER INFORMATION: n = A,T,C or G

<400> SEQUENCE: 95
tgttcctttc tatgcggccc agccggccgt nnstccnnsn nsaccnnsnn sggtgacgac      60
gcaccggtag gtgcgccggt gcc                                             83
```

PROTEIN BINDING MINIATURE PROTEINS

CROSS REFERENCE TO RELATED APPLICATIONS

This application is a continuation-in-part of U.S. patent application Ser. No. 09/840,085 filed Apr. 24, 2001, which claims the benefit of U.S. Provisional Application No. 60/199,408 filed Apr. 24, 2000; No. 60/240,566 filed Oct. 16, 2000; and U.S. Provisional Application No. 60/265,099 filed Jan. 30, 2001; and No. 60/271,368 filed Feb. 23, 2001. This application also claims priority to U.S. Provisional Patent Application No. 60/517,496 filed on Nov. 4, 2003. The teachings of these referenced applications are incorporated herein by reference in their entirety.

FUNDING

Work described herein was funded, in whole or in part, by National Institutes of Health, Grant Numbers 5-R01-GM59483 and 1-R01-GM65453-01. The United States government has certain rights in the invention.

FIELD OF THE INVENTION

The present invention relates to a polypeptide scaffold, such as an avian pancreatic polypeptide, that is modified by substitution of at least one amino acid residue that is exposed on the alpha helix domain of the polypeptide when the polypeptide is in a tertiary form. The invention also relates to phage display libraries for such scaffolds.

BACKGROUND OF THE INVENTION

Many proteins recognize nucleic acids, other proteins or macromolecular assemblies using a partially exposed alpha helix. Within the context of a native protein fold, such alpha helices are usually stabilized by extensive tertiary interactions with residues that may be distant in primary sequence from both the alpha helix and from each other. With notable exceptions (Armstrong et al., (1993) J. Mol. Biol. 230, 284-291), removal of these tertiary interactions destabilizes the alpha helix and results in molecules that neither fold nor function in macromolecular recognition (Zondlo & Schepartz, (1999) J. Am. Chem. Soc. 121, 6938-6939). The ability to recapitulate or perhaps even improve on the recognition properties of an alpha helix within the context of a small molecule should find utility in the design of synthetic mimetics or inhibitors of protein function (Cunningham et al., (1997) Curr. Opin. Struct. Biol. 7, 457-462) or new tools for proteomics research.

Two fundamentally different approaches have been taken to bestow alpha helical structure on otherwise unstructured peptide sequences. One approach makes use of modified amino acids or surrogates that favor helix initiation (Kemp et al., (1991) J. Org. Chem. 56, 6683-6697) or helix propagation (Andrews & Tabor, (1999) Tetrahedron 55, 11711-11743; Blackwell & Grubbs, (1998) Angew. Chem. Int. Ed. Eng. 37, 3281-3284; Schafmeister et al., (2000) J. Am. Chem. Soc. 122, 5891-5892). Perhaps the greatest success has been realized by joining the i and i+7 positions of a peptide with a long-range disulfide bond to generate molecules whose helical structure was retained at higher temperatures (Jackson et al., (1991) J. Am. Chem. Soc. 113, 9391-9392). A second approach (Cunningham et al., (1997) Curr. Opin. Struct. Biol. 7, 457-462; Nygren, (1997) Curr. Opin. Struct. Biol. 7, 463-469), is to pare the extensive tertiary structure surrounding a given recognition sequence to generate the smallest possible molecule possessing function. This strategy has generated minimized versions of the Z domain of protein A (fifty-nine amino acids) and atrial natriuretic peptide (twenty-eight amino acids). The two minimized proteins, at thirty-three and fifteen amino acids, respectively, displayed high biological activity (Braisted & Wells, (1996) Proc. Natl. Acad. Sci., USA 93, 5688-5692; Li et al., (1995) Science 270, 1657-1660). Despite this success, it is difficult to envision a simple and general application of this truncation strategy in the large number of cases where the alpha helical epitope is stabilized by residues scattered throughout the primary sequence.

In light of this limitation, a more flexible approach to protein minimization called protein grafting has been employed. Schematically, protein grafting involves removing residues required for molecular recognition from their native alpha helical context and grafting them on the scaffold provided by small yet stable proteins. Numerous researchers have engineered protein scaffolds to present binding residues on a relatively small peptide carrier. These scaffolds are small polypeptides onto which residues critical for binding to a selected target can be grafted. The grafted residues are arranged in particular positions such that the spatial arrangement of these residues mimics that which is found in the native protein. These scaffolding systems are commonly referred to as miniproteins. A common feature is that the binding residues are known before the miniprotein is constructed.

Examples of these miniproteins include the thirty-seven amino acid protein charybdotoxin (Vita et al., (1995) Proc. Natl. Acad. Sci. USA 92, 6404-6408; Vita et al., (1998) Biopolymers 47, 93-100) and the thirty-six amino acid protein, avian pancreatic peptide (Zondlo & Schepartz, (1999) Am. Chem. Soc. 121, 6938-6939). Avian pancreatic polypeptide (aPP) is a polypeptide in which residues fourteen through thirty-two form an alpha helix stabilized by hydrophobic contacts with an N-terminal type II polyproline (PPII) helix formed by residues one through eight. Because of its small size and stability, aPP is an excellent scaffold for protein grafting of alpha helical recognition epitopes (Zondlo & Schepartz, (1999) J. Am. Chem. Soc. 121, 6938-6939).

SUMMARY OF THE INVENTION

The invention encompasses an avian pancreatic polypeptide modified by substitution of at least one amino acid residue; this residue is exposed on the alpha helix domain of the polypeptide when the polypeptide is in a tertiary form. In some embodiments, the modified polypeptide contains at least six substituted residues, while in other embodiments it contains eight substituted residues, while in another embodiment it contains ten substituted residues, while in yet another embodiment it contains at least twelve substituted residues.

The substituted residues are selected from a site on a known protein through which interaction with another molecule occurs. For example, one or more amino acid residues present in (of) a site on a known protein through which the known protein interacts (e.g., binds) with a binding partner replace one or more amino acid residues of the avian pancreatic polypeptide. Known proteins include, but are not limited to, GCN4, CEBP, Max, Myc, MyoD, double minute two, Bcl-2, protein kinase A, Jun and Fos. In a preferred embodiment, the site on the known protein is a binding site. In some embodiments the modified avian pancreatic polypeptide is capable of inhibiting the interaction between the known protein and another molecule while in other embodiments it is capable of enhancing the interaction. In some embodiments, the binding site is a DNA binding site while in others it is a protein binding site. Preferred DNA binding sites include, but are not limited to the CRE half site, the CEBP site, the MyoD half site and the Q50 engrailed variant site.

The invention also encompasses a phage-display library comprising a plurality of recombinant phage that express any of the aforementioned modified avian pancreatic polypeptides of the invention. In a related embodiment, the invention encompasses a phage-display library comprising a plurality of recombinant phage that express a protein scaffold modified by substitution of at least one amino acid residue, this residue being exposed on the polypeptide when the polypeptide is in a tertiary form. In some embodiments, the protein scaffold of the phage-display library comprises the avian pancreatic polypeptide. The invention also encompasses an isolated phage selected from the phage library of the invention.

In specific embodiments, the invention is a modified avian pancreatic polypeptide (aPP) comprising substitution of at least one amino acid residue, said at least one residue being exposed on the alpha helix domain of the polypeptide when the polypeptide is in a tertiary form, wherein the modified polypeptide binds to a target protein. In specific embodiments, at least six amino acid residues, at least eight amino acid residues, at lease ten amino acid residues or at least twelve amino acid residues are substituted. In certain embodiments, the site is a protein-binding site. The at least one substituted residues can be from any site of a known protein through which the known protein interacts with its binding partner. The target protein can be, for example, a binding partner of the known protein, which can be, for example, a Bcl2 protein, p53, a protein kinase inhibitor (PKI), or CREB. The binding partner can be, for example, selected from the group consisting of a Bcl2 protein, MDM2, protein kinase A or CBP. A variety of modified polypeptides can be produced, such as a modified polypeptide that inhibits interaction between the known protein and the binding partner; a modified polypeptide that binds to a deep groove of the target protein; a modified polypeptide that binds to the groove of the target protein, wherein the groove is more than 6 Å at deepest point; a modified polypeptide that binds to a shallow groove of the target protein; a modified polypeptide that binds to the shallow groove of the target protein, wherein the groove is less than 6 Å at deepest point. The modified polypeptide can bind to the target protein with a Kd of less than 1 micromolar or to the target protein with high specificity.

In certain embodiments, the modified polypeptide comprises an amino acid sequence selected from the sequence represented in FIGS. 1, 5, 7 or Table 1.

Further embodiments of the invention are as follows, with reference to the appended claims:

19. A stabilized miniature protein comprising a miniature protein and a second portion comprising a stabilizing domain, wherein the miniature protein is a modified avian pancreatic polypeptide (aPP) comprising substitution of at least one amino acid residue, said at least one residue being exposed on the alpha helix domain of the polypeptide when the polypeptide is in a tertiary form, wherein the modified polypeptide binds to a target protein.

20. The stabilized miniature protein of claim 19, wherein the second portion is a polypeptide covalently fused to the miniature protein.

21. The stabilized miniature protein of claim 20, wherein the second portion is selected from the group consisting of serum albumin and an IgG Fc domain.

22. The stabilized miniature protein of claim 19, wherein the second portion is a non-amino acid moiety.

23. The stabilized miniature protein of claim 19, wherein said miniature protein includes one or more modified amino acid residues selected from the group consisting of a phosphorylated amino acid, a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

24. A pharmaceutical preparation comprising: a) a modified polypeptide of claim 1; and b) a pharmaceutically acceptable carrier.

25. The pharmaceutical preparation of claim 24, wherein said preparation is substantially pyrogen free.

26. A pharmaceutical preparation comprising: a) a stabilized miniature protein of claim 19 ; and b) a pharmaceutically acceptable carrier.

27. The pharmaceutical preparation of claim 26, wherein said preparation is substantially pyrogen free.

28. A phage-display library comprising a plurality of recombinant phage that express the modified avian pancreatic polypeptide of claim 1.

29. A phage-display library comprising a plurality of recombinant phage that express a protein scaffold modified by substitution of at least one amino acid residue, said at least one residue being exposed on the polypeptide when the polypeptide is in a tertiary form, wherein the modified polypeptide binds to a target protein.

30. The phage-display library of claim 29, wherein said protein scaffold comprises an avian pancreatic polypeptide (aPP).

31. A phage selected from the library of claim 29.

32. An isolated avian pancreatic polypeptide modified by substitution of at least one amino acid residue, wherein the modified polypeptide comprises a sequence selected from the group consisting of:
(a) an amino acid sequence selected from FIGS. 1, 5, 7 and Table 1;
(b) a fragment of at least twelve (12) amino acids of any amino acid sequence selected from FIGS. 1, 5, 7 and Table 1;
(c) an amino acid sequence selected from FIGS. 1, 5, 7, and Table 1; comprising one or more conservative amino acid substitutions;
(d) an amino acid sequence selected from FIGS. 1, 5, 7, and Table 1; comprising one or more naturally occurring amino acid sequence substitutions; and
(e) an amino acid sequence at least 95% identical to any amino acid sequence selected from FIGS. 1, 5, 7, and Table 1.

33. An isolated nucleic acid encoding any one of the polypeptides in claim 32.

34. A recombinant polynucleotide comprising a promoter sequence operably linked to a nucleic acid of claim 33.

35. A cell transformed with a recombinant polynucleotide of claim 34.

36. The cell of claim 35, wherein the cell is a mammalian cell.

37. The cell of claim 35, wherein the cell is a human cell.

38. A method of making a miniature protein, comprising:
a) culturing a cell under conditions suitable for expression of the miniature protein, wherein said cell is transformed with a recombinant polynucleotide of claim 34 ; and
b) recovering the miniature protein so expressed.

39. A method of preparing a miniature protein that modulates the interaction between a known protein and another molecule, comprising the steps of:

(a) identifying at least one amino acid residue that contributes to the binding between a known protein and another molecule; and (b) modifying an avian pancreatic polypeptide by substitution of said at least one amino acid residue, such that it is exposed on the alpha helix domain of the polypeptide when the polypeptide is in a tertiary form.

40. A method of identifying a miniature protein that modulates the interaction between a known protein and another molecule, comprising isolating at least one recombinant phage clone from the phage display library of claim 29 that displays a protein scaffold that modulates the association between a known protein and another molecule.

41. A method for treating a subject having a disorder associated with abnormal cell growth and differentiation, comprising administering to the subject an effective amount of a miniature protein.

42. The method of claim 41, wherein the disorder is selected from the group consisting of inflammation, allergy, autoimmune diseases, infectious diseases, and tumors.

43. The method of claim 41, wherein the miniature protein is selected from the group consisting of:
a) a modified polypeptide of claim 1;
b) a stabilized miniature protein of claim 19; and
c) an modified avian pancreatic polypeptide of claim 32.

44. A method of activating p53 function in a cell, comprising contacting the cell with a miniature protein or a stabilized miniature protein.

46. The method of claim 44, wherein the miniature protein or stabilized miniature protein inhibits binding of p53 to MDM2.

47. The method of claim 44, wherein the cell is a mammalian cell.

48. The method of claim 44, wherein the cell is a cancer cell.

49. A method of inhibiting a protein kinase activity in a cell, comprising contacting the cell with a miniature protein or a stabilized miniature protein.

50. The method of claim 49, wherein the miniature protein or stabilized miniature protein comprises an amino acid sequence selected from FIG. 5.

51. The method of claim 49, wherein the miniature protein or stabilized miniature protein binds to the protein kinase.

52. The method of claim 49, wherein the protein kinase is PKA.

53. The method of claim 49, wherein the miniature protein or stabilized miniature protein is conjugated with a protein kinase inhibitor (PKI).

54. The method of claim 49, wherein the cell is a mammalian cell.

55. The method of claim 49, wherein the cell is a cancer cell.

56. A method of activating CBP function in a cell, comprising contacting the cell with a miniature protein or a stabilized miniature protein.

57. The method of claim 56, wherein the miniature protein or stabilized miniature protein comprises an amino acid sequence selected from FIG. 7 and Table 1.

58. The method of claim 56, wherein the miniature protein or stabilized miniature protein binds to CBP.

59. The method of claim 56, wherein the miniature protein or stabilized miniature protein activates transcription via a CBP-dependent pathway.

60. The method of claim 56, wherein the cell is a mammalian cell.

61. The method of claim 56, wherein the cell is a cancer cell.

62. Use of a miniature protein or stabilized miniature protein for making a medicament for the treatment of a disorder associated with abnormal cell growth and differentiation.

63. The method of claim 62, wherein the disorder is selected from the group consisting of inflammation, allergy, autoimmune diseases, infectious diseases, and tumors.

BRIEF DESCRIPTION OF THE DRAWINGS

FIG. 1—Seven distinct sequences isolated from BAKLIB phage library. Dissociation constants for miniature protein binding to Bcl-2 are shown on the right.

FIG. 6—Affinity and inhibitory potency of PKA ligands. Fluorescence polarization analysis of the equilibrium affinity of $PKI^{Flu}$ (black), $1^{Flu}$ (blue) and $2^{Flu}$ (orange) for PKA in the presence (A) and absence (B) of 100 μM ATP. Inhibition of the phosphotransferase activity of PKA (red), PKB (black), PKCα (blue), PKG (green), and CamKII (pink) by (C) K252a; (D) PKI-K252a; and (E) 1-K252a.

FIG. 7—Protein grafting applied to the $KID^P$•KIX interaction. (A) Schematic representation of the protein grafting process. In the $KID^P$•KIX complex, the backbone of CREB KID helix B is in blue, the hydrophobic residues of helix B important for CBP KIX binding are in red, the PKA recognition site is in green, and the Ser phosphate moiety is in blue (phosphorous) and white (oxygen). In aPP, residues from the α-helix that form part of the hydrophobic core are in blue and residues from the polyproline helix are in orange. In PPKID Library 1, the Cα atoms at randomized positions are in orange. (B) Library design. The amino acid sequence of helix B of CREB KID is aligned with the sequence of the α-helix of aPP. The amino acid sequence of PPKID Library 1 is below. Residues important for aPP folding are in blue, the PKA recognition site is in green, and hydrophobic residues of helix B important for binding CBP KIX are in red. Randomized residues are represented by X in orange. (C) Comparison of the α-helix-binding surfaces of Bcl-$X_L$ (left) and CBP KIX (right). Bcl-$X_L$ contains a deep (~7 Å) hydrophobic cleft that recognizes the Bak BH3 α-helix. CBP KIX binds the CREB KID helix B in a shallow depression (<5 Å at the deepest point) on its surface.

Figure 2:
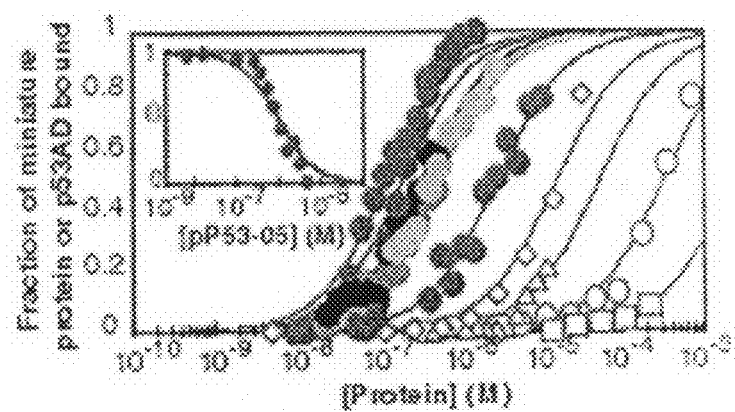
FIG. 2—Fluorescence polarization analysis of the affinity of GST-MDM2 for selected peptides and the affinity of pP53-05 for selected proteins. Plots illustrate the fraction of fluorescein-labeled p53AD, pP53-05, pP53-03, pP53-04, pP53-01, pP53-02 bound as a function of GST-MDM2 concentration; and the fraction of fluorescein-labeled pP53-05 bound (Θ) as a function of (◇) protein kinase A, (Δ) Fos, (○) carbonic anhydrase, (□) calmodulin. Each point represents the average of at least three trials. Error bars represent the standard error. $K_d$ values were calculated as described in Heyduk, et al., *Proc Natl Acad Sci USA* 1990, 87, 1744. Inset: Competition between pP53-05 and p53AD for GST-MDM2, as monitored by fluorescence polarization analysis. Plot illustrates the fraction of p53AD-Flu (10 nM) bound to GST-MDM2 (400 nM) at equilibrium as a function of added pP53-05 (4.5 μM-0.18 μM). $K_i$ was calculated using the Cheng-Prusoff equation.

Bars and standard error represent the results from at least 3 independent trials. Firefly luciferase values were normalized to an internal control (luciferase values from promoterless *Renilla* luciferase vector) to correct for transfection efficiency. Fold activation represents normalized luciferase relative to values for Gal4 DBD alone under the same. Where phosphorylation is indicated, 5 μM forskolin was added to media 6 hours before harvesting cells.

DETAILED DESCRIPTION

Definitions

As used herein, the term "binding" refers to the specific association or other specific interaction between two molecular species, such as, but not limited to, protein-DNA interactions and protein-protein interactions. The specific association can be, for example, between proteins and their DNA targets, receptors and their ligands, enzymes and their substrates. It is contemplated that such association is mediated through specific sites on each of the two interacting molecular species. Binding is mediated by structural and/or energetic components, the latter comprising the interaction of molecules with opposite charges.

As used herein, the term "binding site" refers to the reactive region or domain of a macromolecule that directly participate in its specific binding with another molecule. For example, when referring to the binding site on a protein or nucleic acid, binding occurs as a result of the presence of specific amino acids or nucleotide sequence, respectively, that interact with the other molecule and, collectively, are referred to as a "binding site."

As used herein, the term "exposed on the alpha helix domain" means that an amino acid substituted, for example, into the avian pancreatic polypeptide is available for association or interaction with another molecule and are not otherwise bound to or associated with another amino acid residue on the avian pancreatic polypeptide. This term is used interchangeably with the term "solvent-exposed alpha helical face" throughout the specification.

As used herein, the terms "miniature protein" or "miniprotein" refers to a relatively small protein containing at least a protein scaffold and one or more additional domains or regions that help to stabilize its tertiary structure. The term "miniature protein" includes any variants of the miniature protein (e.g., mutants, fragments, fusions, and peptidomimetic forms) that retain a useful activity. An exemplary protein scaffold is an avian pancreatic polypeptide (aPP). In certain specific embodiments, a miniature protein is referred to as "modified aPP" or "modified polypeptide."

As used herein, the term "modulate" refers to an alteration in the association between two molecular species, for example, the effectiveness of a biological agent to interact with its target by altering the characteristics of the interaction in a competitive or non-competitive manner.

As used herein, the term "protein" refers to any of a group of complex organic compounds which contain carbon, hydrogen, oxygen, nitrogen and usually sulphur, the characteristic element being nitrogen and which are widely distributed in plants and animals. Twenty different amino acids are commonly found in proteins and each protein has a unique, genetically defined amino acid sequence which determines its specific shape and function. The term "protein" is generally used herein interchangeably with the terms peptide and polypeptide.

As used herein, the term "protein scaffold" refers to a region or domain of a relatively small protein, such as a miniature protein, that has a conserved tertiary structural motif which can be modified to display one or more specific amino acid residues in a fixed conformation.

Miniature Proteins

The present invention provides engineered miniature proteins that associate with (i.e., or bind to) specific sequences of DNA or other proteins and also provides methods for designing and making these miniature proteins. These miniature proteins bind, for example, to DNA or other proteins with high affinity and selectivity. Schematically, the invention involves a technique that the inventors have designated as protein grafting (see, e.g., FIGS. 5 and 7). In one aspect, this technique identifies critical binding site residues from a globular protein that participate in binding-type association between that protein and its specific binding partners, then these residues are grafted onto a small but stable protein scaffold. The preferred protein scaffolds of the invention comprise members of the pancreatic fold (PP fold) protein family, particularly the avian pancreatic polypeptide (aPP). Thus, in certain specific embodiments, the miniature protein is referred to a modified polypeptide such as a modified aPP.

The PP fold protein scaffolds of the invention generally contain thirty-six amino acids and are the smallest known globular protein. For example, an avian pancreatic polypeptide (aPP) sequence is designed as SEQ ID NO: 36. Despite their small size, PP fold proteins are stable and remain folded under physiological conditions. The preferred PP fold protein scaffolds of the invention consist of two anti-parallel helices, an N-terminal type II polyproline helix (PPII) between amino acid residues two and eight and an alpha-helix between residues 14 and 31 and/or 32. The stability of the PP fold protein scaffolds of the invention derives predominantly from interactions between hydrophobic residues on the interior face of the alpha-helix at positions 17, 20, 24, 27, 28, 30 & 31 and the residues on the two edges of the polyproline helix at positions 2, 4, 5, 7 & 8. In general, the residues responsible for stabilizing it tertiary structure are not substituted in order to maintain the tertiary structure of the miniature protein or are compensated for using phage display.

In certain embodiments, two or more of the critical binding site residues of, for example, a selected globular protein are grafted onto the protein scaffold in positions which are not essential in maintaining tertiary structure, preferably on the solvent-exposed alpha helical face. In one preferred embodiment, six or more of such binding site residues are grafted onto the protein scaffold. In a more preferred embodiment, eight or more of such binding site residues are grafted onto the protein scaffold. In an even more preferred embodiment, ten or more of such binding site residues are grafted onto the protein scaffold. In a most preferred embodiment, twelve or more of such binding site residues are grafted onto the protein scaffold. Preferred positions for grafting these binding site residues on the protein scaffold include, but are not limited to, positions on the solvent-exposed alpha-helical face of aPP. Substitutions of binding site residues may be made, although they are less preferred, for residues involved in stabilizing the tertiary structure of the miniature protein.

The skilled artisan will readily recognize that it is not necessary that actual substitution of the grafted residues occur on the protein scaffold. Rather it is necessary that a peptide be identified, through, for example, phage display, that comprises a polypeptide constituting a miniature protein having the association characteristics of the present invention. Such peptides may be produced using any conventional means, including, but not limited to synthetic and recombinant techniques.

Members of the PP fold family of protein scaffolds which are contemplated by the present invention include, but are not limited to, avian pancreatic polypeptide (aPP), Neuropeptide Y, lower intestinal hormone polypeptide and pancreatic peptide. In the most preferred embodiment, the protein scaffold comprises the PP fold protein, avian pancreatic polypeptide (SEQ ID NO: 06) (see, e.g., Blundell et al., (1981) Proc. Natl. Acad. Sci. USA 78, 4175-4179; Tonan et al., (1990) Biochemistry 29, 4424-4429). aPP is a PP fold polypeptide characterized by a short (eight residue) amino-terminal type II polyproline helix linked through a type I beta turn to an eighteen residue alpha-helix. Because of its small size and stability, aPP is an excellent protein scaffold for, e.g., protein grafting of alpha-helical recognition epitopes.

DNA-Binding Miniature Proteins

In another aspect, the present invention encompasses miniature proteins that bind to specific DNA sequences and further encompasses methods for making and using such miniature proteins. In some embodiments, these DNA sequences comprise sites for known proteins that bind to that specific DNA sequence (contemplated known proteins would be, e.g., a promotor or regulator). For example, in the design of a DNA-binding miniature protein, the amino acid residues of a known protein that participate in binding or other association of the protein to that particular DNA sequence are identified.

In some embodiments of the present invention, the relevant binding residues are identified using three-dimensional models of a protein or protein complex based on crystallographic studies while in other embodiments they are identified by studies of deletion or substitution mutants of the protein. The residues that participate in binding of the protein to the specific DNA sequence are then grafted onto those positions of the miniature protein that are not necessary to maintain the tertiary structure of the protein scaffold to form the DNA-binding miniature protein. The identification of such positions can readily be determined empirically by persons skilled in the art. Other embodiments of the present invention involve the screening of a library of modified miniproteins that contain peptide species capable of specific association or binding to that specific DNA (or, in other cases, protein) sequence or motif.

Generally, it is contemplated that any potential binding site on a DNA sequence can be targeted using the DNA binding miniature proteins of the invention. Preferred embodiments include helical structures which bind to the DNA binding site. In some embodiments, the binding involves a basic region leucine zipper (bZIP) structure (Konig & Richmond, (1995) J. Mol. Biol. 254, 657-667) while in other embodiments the structure involves a basic-helix-loop-helix (bHLH) structure (Shimizu et al., (1997) EMBO J. 16, 4689-4697). In another embodiment, the binding involves a structure like those found in homeodomain proteins (Scott & Weimer, (1984) Proc. Natl. Acad. Sci. 81, 4115-4119). Preferred bZIP structures include, but are not limited to, those found in GCN4 and C/EBP-delta (Suckow et al., (1993) EMBO J. 12, 1193-1200) while preferred bHLH structures include, but are not limited to, those found in Max (Ferre-D'Amare et al., (1993) Nature 363, 38-45), Myc and MyoD (Ma et al., (1994) Cell 77, 451-459). Preferred homeodomain structures include, but are not limited to, those found in the Q50 engrailed variant protein (Kissinger et al., (1990) Cell 63, 579-590).

In one embodiment, the invention encompasses a DNA-binding miniature protein that binds to the cAMP Response Element (CRE) half-site promotor DNA sequence (ATGAC) (SEQ ID NO: 65). Essential residues for binding are identified from the protein GCN4 which is a bZIP protein which binds to this sequence. These residues are identified by utilizing the three-dimensional structure of the GCN4 protein which bind to the hsCRE and grafting these residues onto the protein scaffold. By grafting various combinations of residues on the solvent-exposed alpha-helical face or domain of aPP which are essential to binding of GCN4 (SEQ ID NO: 7) to the CRE half site (hsCRE), a series of polyproline helix-basic region (PPBR$^{SR}$) molecules containing most or all of the DNA-contact residues of GCN4 and most or all of the folding residues of aPP is generated. This procedure generated three positions (Tyr27, Leu28 and Val30) where essential DNA-contact and aPP-folding residues occupied a single position on the helix.

Examples of the DNA-binding miniature proteins which bind to hsCRE include, but are not limited to, the amino acid sequences depicted in SEQ ID NO: 11 (PPBR2$^{SR}$), 12 (PPBR4$^{SR}$), 13 (G$_{27}$) & 14 (PPBR4Δ$^{SR}$).

In another embodiment, protein grafting was used for the design of a miniature protein whose DNA binding properties mimic those of the CCAAT/enhancer protein C/EBP-delta. C/EBP-delta is a member of the C/EBP sub-family of bZIP transcription factors that includes C/EBP-alpha, C/EBP-beta, C/EBP-gamma, C/EBP-delta and C/EBP-epsilon. Although C/EBP proteins are members of the bZIP superfamily, they differ from CGN4 at several residues within the DNA recognition helix. In particular, D/EBP-delta and GCN4 differ at two of six residues that contact bases or sugars and three of six residues that contact phosphates in all published structures of GCN4 DNA complexes. These changes, as well as the substitution of tyrosine or alanine at position fifteen, contribute to the preferred interaction of C/EBP proteins with the C/EBP site (ATTGCGCAAT) (SEQ ID NO: 67) over the CRE site (ATGACGTCAT) (SEQ ID NO: 68) recognized by GCN4.

For the design of PPEBP (polyproline-enhancer binding protein) according to the present invention, the first step in the grafting protocol is alignment of the alpha-helix of aPP (residues 14-36) with the alpha-helical region of the protein of interest. Alignment of the aPP alpha-helix with residues 187-221 (the DNA-binding basic segment) of human C/EBP-delta identified three conflict positions (27, 28 & 30 according to the aPP numbering system) where DNA-contact residues within C/EBP-delta and folding residues within aPP occupied the same position on the helix. The PPEBP1$^{SR}$ (SEQ ID NO: 47) miniature protein of the invention contains arginine residues derived from C/EBP-delta at positions 27, 28 & 30 to preserve binding affinity because high-affinity DNA recognition by PPEBP miniature proteins is enhanced by retention of DNA-contact residues at these positions despite the concomitant loss in folding energy. In addition, tyrosine, asparagine and valine residues are substituted at positions 15, 23 & 26, respectively to foster specific recognition of the C/EBP half site ATTGC (hsCEBP)(SEQ ID NO: 66). Finally an alanine residue is inserted at position 31 in place of the potentially core-disrupting and complex-destabilizing aspartate found in C/EBP-delta and in place of the helix destabilizing valine present at this position of aPP.

Examples of the DNA-binding miniature proteins which bind to the C/EBP site include, but are not limited to, the amino acid sequences depicted in SEQ ID NO: 47 (PPEBP1$^{SR}$), 48 (PPEBP2$^{SR}$) and 49 (EBP1$^{SR}$).

Methods of Producing Miniature Proteins Using Phage Display

In some embodiments, a miniature protein is produced and selected using a phage display method (McCafferty et al., (1990) Nature 348, 552-554). In such a method, display of recombinant miniature proteins on the surface of viruses which infect bacteria (bacteriophage or phage) make it possible to produce soluble, recombinant miniature proteins having a wide range of affinities and kinetic characteristics. To display the miniature proteins on the surface of phage, a synthetic gene encoding the miniature protein is inserted into the gene encoding a phage surface protein (pIII) and the recombinant fusion protein is expressed on the phage surface (McCafferty et al., (1990) Nature 348, 552-554; Hoogenboom et al., (1991) Nucleic Acids Res. 19, 4133-4137). Variability is introduced into the phage display library to select for miniature proteins which not only maintain their tertiary, helical structure but which also display increased affinity for a preselected target because the critical (or contributing but not critical) binding residues are optimally positioned on the helical structure.

Since the recombinant proteins on the surface of the phage are functional, phage bearing miniature proteins that bind with high-affinity to a particular target DNA or protein can be separated from non-binding or lower affinity phage by antigen affinity chromatography. Mixtures of phage are allowed to bind to the affinity matrix, non-binding or lower affinity phage are removed by washing, and bound phage are eluted by treatment with acid or alkali. Depending on the affinity of the miniature protein for its target, enrichment factors of twenty-fold to a million-fold are obtained by a single round of affinity selection. By infecting bacteria with the eluted phage, however, more phage can be grown and subjected to another round of selection. In this way, an enrichment of a thousand-fold in one round becomes a million-fold in two rounds of selection. Thus, even when enrichments in each round are low (Marks et al., (1991) J. Mol. Biol, 222, 581-597), multiple rounds of affinity selection leads to the isolation of rare phage and the genetic material contained within which encodes the sequence of the domain or motif of the recombinant miniature protein that binds or otherwise specifically associates with it binding target.

In various embodiments of the invention, the methods disclosed herein are used to produce a phage expression library encoding miniature proteins capable of binding to a DNA or to a protein that has already been selected using the protein grafting procedure described above. In such embodiments, phage display can be used to identify miniature proteins that display an even higher affinity for a particular target DNA or protein than that of the miniature proteins produced without the aid of phage display. In yet another embodiment, the invention encompasses a universal phage display library that can be designed to display a combinatorial set of epitopes or binding sequences to permit the recognition of nucleic acids, proteins or small molecules by a miniature protein without prior knowledge of the natural epitope or specific binding residues or motifs natively used for recognition and association.

Various structural modifications also are contemplated for the present invention that, for example, include the addition of restriction enzyme recognition sites into the polynucleotide sequence encoding the miniature protein that enable genetic manipulation of these gene sequences. Accordingly, the re-engineered miniature proteins can be ligated, for example, into an M13-derived bacteriophage cloning vector that permits expression of a fusion protein on the phage surface. These methods allow for selecting phage clones encoding fusion proteins that bind a target ligand and can be completed in a rapid manner allowing for high-throughput screening of miniature proteins to identify the miniature protein with the highest affinity and selectivity for a particular target.

According to the methods of the invention, a library of phage displaying modified miniature proteins is incubated with the immobilized target DNA or proteins to select phage clones encoding miniature proteins that specifically bind to or otherwise specifically associate with the immobilized DNA or protein. This procedure involves immobilizing a oligonucleotide or polypeptide sample on a solid substrate. The bound phage are then dissociated from the immobilized oligonucleotide or polypeptide and amplified by growth in bacterial host cells. Individual viral plaques, each expressing a different recombinant miniature protein, are expanded to produce amounts of protein sufficient to perform a binding assay. The DNA encoding this recombinant binding protein can be subsequently modified for ligation into a eukaryotic protein expression vector. The modified miniature protein, adapted for expression in eukaryotic cells, is ligated into a eukaryotic protein expression vector.

Phage display methods that can be used to make the miniature proteins of the present invention include those disclosed in Brinkman et al., (1995) J. Immunol. Methods 182, 41-50; Ames et al., (1995) J. Immunol. Methods 184:177-186; Kettleborough et al., (1994) Eur. J. Immunol. 24, 952-958; Persic et al., (1997) Gene 187, 9-18; Burton et al., (1994) Adv. Immunol. 57, 191-280; U.S. Pat. Nos. 5,698,426; 5,223, 409; 5,403,484; 5,580,717; 5,427,908; 5,750,753; 5,821,047; 5,571,698; 5,427,908; 5,516,637; 5,780,225; 5,658,727; 5,733,743, 5,837,500 & 5,969,108.

Protein-Binding Miniature Proteins and Variants Thereof

The invention encompasses miniature proteins that bind to other proteins and methods for making these miniature proteins. The binding of the miniature proteins modulates protein-protein and/or protein-ligand interactions. Thus, in some embodiments, the binding blocks the association (or specific binding) of ligands and receptors. The ligand can be either another protein but also can be any other type of molecule such as a chemical substrate. In one embodiment of the present invention, making the protein-binding miniature protein of the invention involves identifying the amino acid residues which are essential to binding of the ligand protein to its target receptor protein. In some embodiments, these essential residues are identified using three-dimensional models of a protein or protein complex which binds to or interacts with another protein based on crystallographic studies while in other embodiments they are identified by studies of deletion or substitution mutants of the protein. The residues that participate in binding of the protein to are then grafted onto those positions which are not necessary to maintain the tertiary structure of the protein scaffold to form the protein-binding miniature protein.

The structure of any protein which binds to another protein can be used to derive the protein-binding miniature proteins of the invention. Preferred embodiments include helical structures such as those involved in protein-protein interactions between Fos and Jun (Kouzarides & Ziff, (1988) Nature 336, 646-651); Bcl-2 and Bak (Sattler et al., (1997) Science 275, 983-986); CBP-KIX and CREB-KID (Radhakrishnan et al., (1997) Cell 91, 741-752); p53 and MDM2 (Kussie et al., (1996) Science 274, 948-953); and a protein kinase and a protein kinase inhibitor (PKI) (Glass et al., (1989) J Biol Chem 264, 14579-84). In some embodiments, the binding involves coiled coil protein structures and/or leucine zippers.

In one embodiment of the invention, the methods disclosed herein are used to produce a miniature protein that binds to the Bcl-2 or Bcl-$X_L$ proteins (Sattler et al., (1997) Science 275, 983-986). In this method, the protein grafting procedure described herein was applied to the Bak-BH3 binding domain to design a miniature protein capable of binding to Bcl-$X_L$. In this procedure, the primary sequence of a protein of interest is aligned with residues in the alpha helix of aPP. All possible alignments of the primary sequence of positions 74-92 of Bak with aPP are assessed in two ways. First, the number of conflicts in a primary sequence alignment between residues important for hydrophobic core formation or maintenance of aPP helix dipole, and residues in Bak important for binding Bcl-$X_L$ was considered. Alignments with a large number of conflicts are eliminated as they would force selection between sequences that were well folded or have high affinity, but make it difficult to isolate a molecule with both these properties.

Structural models of the aPP based peptides that are associated or complexed with the BH3 domain of Bcl-$X_L$ in each of the alignments are evaluated for unfavorable interactions or steric clashes between the VanderWaals surface of Bcl-$X_L$ and the backbone of the aPP scaffold. Structural models with multiple unfavorable interactions or steric clashes are eliminated from further consideration.

An alignment is identified with only a single conflict where structural modeling suggested no steric clashes. A phage display expression library of chimeric peptides ultimately was based on this alignment. The resulting library of peptides was displayed on the surface of M13 phage and used in selection and isolation of miniature proteins that bind Bcl with high-affinity. Examples of bcl2-binding miniature proteins include, but are not limited to, those sequences having a carboxyl portion sequence as depicted in SEQ ID NO: 23 (4100), 24 (4101), 25 (4099) or 26 (4102). The amino terminal portion of the miniature proteins is understood to derive from the amino terminal portion (e.g., residues 1-19) of the aPP (SEQ ID NO: 6).

In another embodiment of the invention, the methods of the invention are used to produce a miniature protein that binds to the human double minute two (MDM2). The alpha-helical segments of p53 and aPP were aligned to identify three critical MDM2 contact residues (e.g., positions 22, 26, and 29) on the exposed alpha-helical face of aPP without substituting any aPP residues important for folding. Because many p53 residues within the p53 activation domain that interacts with MDM2 display phi and psi angles outside the ideal alpha-helical range, this application of protein grafting introduced diversity at five positions along the alpha-helix and the highest affinity ligands were selected using phage display. Examples of miniature proteins which bind to MDM2 include, but are not limited to, pP53-01, pP53-02, pP53-03, pP53-04 and pP53-05.

In another embodiment of the invention, the methods of the invention are used to produce a miniature protein that binds to protein kinase K (PKA). The alpha-helical segments of a PKI and aPP were aligned to identify critical contact residues on the exposed alpha-helical face of aPP without substituting any aPP residues important for folding. Examples of miniature proteins which bind to PKA include, but are not limited to, the amino acid sequences depicted in FIG. 5.

In yet another embodiment of the invention, the methods of the invention are used to produce a miniature protein that binds to CBP (e.g, the KIX domain). The alpha-helical segments of a CREB (e.g., the KID domain) and aPP were aligned to identify critical contact residues on the exposed alpha-helical face of aPP without substituting any aPP residues important for folding. Examples of miniature proteins which bind to CBP include, but are not limited to, the amino acid sequences depicted in FIG. 7 and Table 1.

In certain embodiments, miniature proteins include fragments, functional variants, and modified forms that have similar or the same biological activities of their corresponding wild-type miniature proteins. To illustrate, miniature proteins of the invention bind to a target protein and modulate (e.g., activate or inhibit) a function of the target protein. In certain cases, target proteins of the miniature proteins are known to play a role in cell proliferation and differentiation. Therefore, miniature proteins of the invention can be used for treating or preventing disorders associated with abnormal cell proliferation and differentiation (e.g., inflammation, allergy, autoimmune diseases, infectious diseases, and tumors).

In certain embodiments, miniature proteins of the present invention further include conservative variants of the miniature proteins herein described. As used herein, a conservative variant refers to a miniature protein comprising alterations in the amino acid sequence that do not substantially and adversely affect the binding or association capacity of the protein. A substitution, insertion or deletion is said to adversely affect the miniature protein when the altered sequence prevents or disrupts a function or activity associated with the protein. For example, the overall charge, structure or hydrophobic-hydrophilic properties of the miniature protein can be altered without adversely affecting an activity. Accordingly, the amino acid sequence can be altered, for example to render the peptide more hydrophobic or hydrophilic, without adversely affecting the activities of the miniature protein.

In certain embodiments, these variants, though possessing a slightly different amino acid sequence than those recited above, will still have the same or similar properties associated with the miniature proteins such as those depicted in SEQ ID NOs: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71, and 72; and FIGS. 1, 5, 7 and Table 1.

Ordinarily, the conservative substitution variants, will have an amino acid sequence having at least ninety percent amino acid sequence identity with the miniature sequences such as those set forth in SEQ ID NOs: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 and 72; and FIGS. 1, 5, 7 and Table 1, more preferably at least ninety-five percent, even more preferably at least ninety-eight percent, and most preferably at least ninety-nine percent. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the miniature proteins of the present invention include molecules comprising the amino acid sequence of SEQ ID NOs: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71 and 72; and FIGS. 1, 5, 7 and Table 1; fragments thereof having a consecutive sequence of at least about 20, 25, 30, 35 or more amino acid residues of the miniature proteins of the invention; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those derivatives wherein the protein has been covalently modified by substitution, chemical, enzymatic, or other appropriate means with a moiety other than a naturally occurring amino acid (for example, a detectable moiety such as an enzyme or radioisotope).

In certain embodiments, the miniature proteins of the present invention can be chemically synthesized using techniques known in the art such as conventional Merrifield solid phase f-Moc or t-Boc chemistry. Alternatively, the miniature proteins can be produced (recombinantly or by chemical synthesis).

In certain embodiments, the present invention contemplates making functional variants by modifying the structure of a miniature protein for such purposes as enhancing therapeutic efficacy, or stability (e.g., ex vivo shelf life and resistance to proteolytic degradation in vivo). Such modified miniature proteins when designed to retain at least one activity of the wildtype form of the miniature proteins, are considered functional equivalents of the wildtype miniature proteins.

In certain embodiments, the miniature proteins of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the miniature proteins.

To illustrate, by employing scanning mutagenesis to map the amino acid residues of a miniature protein which are involved in binding to another protein, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the miniature proteins of the invention may further comprise post-translational modifications in addition to any that are naturally present in the miniature proteins. Such modifications include, but are not limited to, acetylation, carboxylation, glycosylation, phosphorylation, lipidation, and acylation. As a result, the modified miniature proteins may contain non-amino acid elements, such as polyethylene glycols, lipids, poly- or monosaccharide, and phosphates. Effects of such non-amino acid elements on the functionality of a miniature protein may be tested by methods such as those described in the working examples.

In certain aspects, functional variants or modified forms of the miniature proteins include fusion proteins having at least a portion of the miniature proteins and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. As another example, a fusion domain may be selected so as to facilitate detection of the miniature proteins. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, a miniature protein is fused with a domain that stabilizes the miniature protein in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties.

Nucleic Acid Molecules Encoding Miniature Proteins

Figure 5:
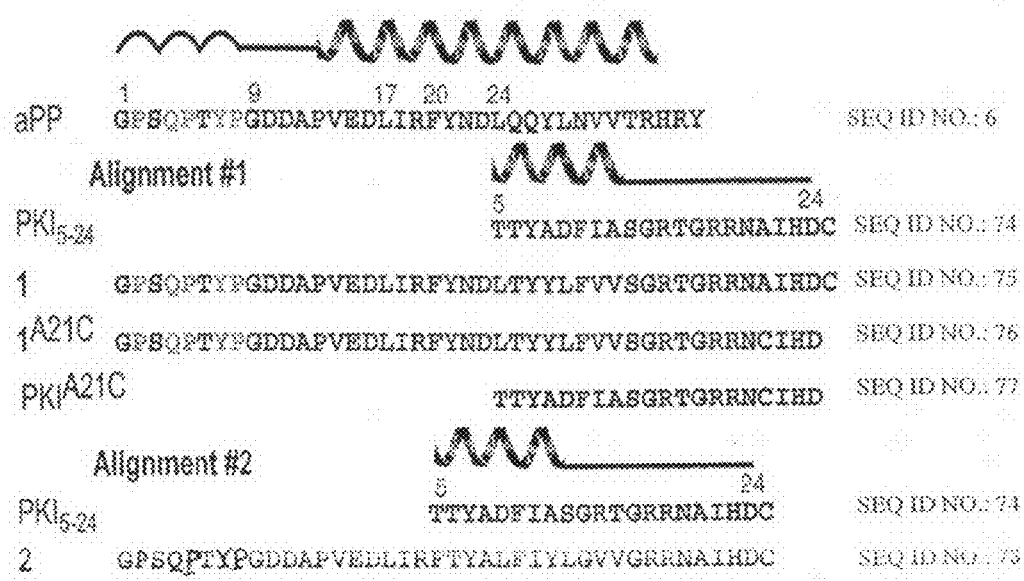
FIG. 5—Design of PKA inhibitors. Residues that contribute significantly to PKA inhibition are in red; residues that contribute to aPP folding are in blue (α-helix) or yellow (PPII helix).

The present invention further provides nucleic acid molecules that encode the miniature proteins comprising any of the amino acid sequences of SEQ ID NOs: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71, and 72; and FIGS. 1, 5, 7 and Table 1, and the related miniature proteins herein described, preferably in isolated form. As used herein, "nucleic acid" includes cDNA and mRNA, as well as nucleic acids based on alternative backbones or including alternative bases whether derived from natural sources or synthesized.

As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecule. As used herein, a "fragment of an encoding nucleic acid molecule" refers to a portion of the entire protein encoding sequence of the miniature protein.

The size of the fragment will be determined by the intended use. For example, if the fragment is chosen so as to encode an active portion of the protein, the fragment will need to be large enough to encode the functional region(s) of the protein. The appropriate size and extent of such fragments can be determined empirically by persons skilled in the art.

Modifications to the primary structure itself by deletion, addition, or alteration of the amino acids incorporated into the protein sequence during translation can be made without destroying the activity of the miniature protein. Such substitutions or other alterations result in miniature proteins having an amino acid sequence encoded by a nucleic acid falling within the contemplated scope of the present invention.

The present invention further provides recombinant DNA molecules that contain a coding sequence. As used herein, a recombinant DNA molecule is a DNA molecule that has been subjected to molecular manipulation. Methods for generating recombinant DNA molecules are well known in the art, for example, see Sambrook et al., (1989) Molecular Cloning—A Laboratory Manual, Cold Spring Harbor Laboratory Press. In the preferred recombinant DNA molecules, a coding DNA sequence is operably linked to expression control sequences and vector sequences.

The choice of vector and expression control sequences to which one of the protein family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the recombinant DNA molecule.

Expression control elements that are used for regulating the expression of an operably linked miniature protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomal in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Any suitable prokaryotic host can be used to express a recombinant DNA molecule encoding a protein of the invention.

Expression vectors compatible with eukaryotic cells, preferably those compatible with vertebrate cells, can also be used to form a recombinant DNA molecule that contains a coding sequence. Eukaryotic cell expression vectors are well known in the art and are available from several commercial sources. Typically, such vectors are provided containing convenient restriction sites for insertion of the desired DNA segment.

Eukaryotic cell expression vectors used to construct the recombinant DNA molecules of the present invention may further include a selectable marker that is effective in a eukaryotic cell, preferably a drug resistance selection marker. A preferred drug resistance marker is the gene whose expression results in neomycin resistance, i.e., the neomycin phosphotransferase (neo) gene. Southern et al., (1982) J. Mol. Anal. Genet. 1, 327-341. Alternatively, the selectable marker can be present on a separate plasmid, the two vectors introduced by co-transfection of the host cell, and transfectants selected by culturing in the appropriate drug for the selectable marker.

Transformed Host Cells

The present invention further provides host cells transformed with a nucleic acid molecule that encodes a miniature protein of the present invention. The host cell can be either prokaryotic or eukaryotic. Eukaryotic cells useful for expression of a miniature protein of the invention are not limited, so long as the cell line is compatible with cell culture methods and compatible with the propagation of the expression vector and expression of the gene product.

Transformation of appropriate cell hosts with a recombinant DNA molecule encoding a miniature protein of the present invention is accomplished by well known methods that typically depend on the type of vector used and host system employed. With regard to transformation of prokaryotic host cells, electroporation and salt treatment methods can be employed (see, for example, Sambrook et al., (1989) Molecular Cloning—A Laboratory Manual, Cold Spring Harbor Laboratory Press; Cohen et al., (1972) Proc. Natl. Acad. Sci. USA 69, 2110-2114). With regard to transformation of vertebrate cells with vectors containing recombinant DNA, electroporation, cationic lipid or salt treatment methods can be employed (see, for example, Graham et al., (1973) Virology 52, 456-467; Wigler et al., (1979) Proc. Natl. Acad. Sci. USA 76, 1373-1376).

Successfully transformed cells (cells that contain a recombinant DNA molecule of the present invention), can be identified by well known techniques including the selection for a selectable marker. For example, cells resulting from the introduction of a recombinant DNA of the present invention can be cloned to produce single colonies. Cells from those colonies can be harvested, lysed and their DNA content examined for the presence of the recombinant DNA using a method such as that described by Southern, (1975) J. Mol. Biol. 98, 503-517 or the proteins produced from the cell assayed via an immunological method.

Production of Recombinant Miniature Proteins

The present invention further provides methods for producing a miniature protein of the invention using nucleic acid molecules herein described. In general terms, the production of a recombinant form of a protein typically involves the following steps: a nucleic acid molecule is obtained that encodes a protein of the invention, such as the nucleic acid molecule encoding any of the miniature proteins depicted in SEQ ID NO: 8, 9, 10, 11, 12, 13, 17, 18, 19, 20, 21, 22, 23, 24, 25, 26, 27, 28, 29, 31, 33, 34, 35, 36, 37, 47, 48, 49, 50, 51, 52, 53, 54, 55, 56, 57, 58, 59, 60, 61, 62, 63, 64, 70, 71, and 72; and FIGS. 1, 5, 7 and Table 1. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant miniature protein. Optionally the recombinant miniature protein is isolated from the medium or from the cells; recovery and purification of the protein may not be necessary in some instances where some impurities may be tolerated.

Each of the foregoing steps can be done in a variety of ways. The construction of expression vectors that are operable in a variety of hosts is accomplished using appropriate replicons and control sequences, as set forth above. The control sequences, expression vectors, and transformation methods are dependent on the type of host cell used to express the gene. Suitable restriction sites, if not normally available, can be added to the ends of the coding sequence so as to provide an excisable gene to insert into these vectors. A skilled artisan can readily adapt any host/expression system known in the art for use with the nucleic acid molecules of the invention to produce a recombinant miniature protein.

Methods to Identify Binding Partners

The present invention provides methods for use in isolating and identifying binding partners of the miniature proteins of the invention. In some embodiments, a miniature protein of the invention is mixed with a potential binding partner or an extract or fraction of a cell under conditions that allow the association of potential binding partners with the protein of the invention. After mixing, peptides, polypeptides, proteins or other molecules that have become associated with a miniature protein of the invention are separated from the mixture. The binding partner bound to the protein of the invention can then be removed and further analyzed. To identify and isolate a binding partner, the entire miniature protein can be used. Alternatively, a fragment of the miniature protein which contains the binding domain can be used.

As used herein, a "cellular extract" refers to a preparation or fraction which is made from a lysed or disrupted cell. A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with a miniature protein of the invention under conditions in which association of the miniature protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the miniature protein of the invention can be immobilized on a solid support. For example, the miniature protein can be attached to a nitrocellulose matrix or acrylic beads. Attachment of the miniature protein to a solid support aids in separating peptide-binding partner pairs from other constituents found in the extract. The identified binding partners can be either a single DNA molecule or protein or a complex made up of two or more proteins. Alternatively, binding partners may be identified using the Alkaline Phosphatase fusion assay according to the procedures of Flanagan & Vanderhaeghen, (1998) Annu. Rev. Neurosci. 21, 309-345 or Takahashi et al., (1999) Cell 99, 59-69; the Far-Western assay according to the procedures of Takayama et al., (1997) Methods Mol. Biol. 69, 171-184 or Sauder et al., J. Gen. Virol. (1996) 77, 991-996 or identified through the use of epitope tagged proteins or GST fusion proteins.

Alternatively, the nucleic acid molecules encoding a miniature protein of the invention can be used in a yeast two-hybrid system. The yeast two-hybrid system has been used to identify other protein partner pairs and can readily be adapted to employ the nucleic acid molecules herein described (see, e.g., Stratagene Hybrizap® two-hybrid system).

Screening, Diagnostic & Therapeutic Uses

The miniature proteins (including variants thereof) of the invention are particularly useful for drug screening to identify agents capable of binding to the same binding site as the miniature proteins. The miniature proteins are also useful for diagnostic purposes to identify the presence and/or detect the levels of DNA or protein that binds to the miniature proteins of the invention. In one diagnostic embodiment, the miniature proteins of the invention are included in a kit used to detect the presence of a particular DNA or protein in a biological sample. The miniature proteins of the invention also have therapeutic uses in the treatment of disease associated with the presence of a particular DNA or protein. In one therapeutic embodiment, the miniature proteins can be used to bind to DNA to promote or inhibit transcription, while in another therapeutic embodiment, the miniature proteins bind to a protein, resulting in inhibition or stimulation of the protein.

As described above, miniature proteins bind to target proteins (MDM2, CBP, PKA, a Bcl2 protein, and variants thereof) which are implicated in cell proliferation and differentiation. Thus, in certain embodiments, the present invention provides methods of treating cancer in an individual suffering from a disorder associated with abnormal cell proliferation and differentiation by administering to the individual a therapeutically effective amount of a miniature protein as described above. Examples of such disorders include, but are not limited to, inflammation, allergy, autoimmune diseases, infectious diseases, and tumors (cancers).

In other embodiments, the invention provides methods of preventing or reducing the onset of a disorder associated with abnormal cell proliferation and differentiation in an individual through administering to the individual an effective amount of a miniature protein. These methods are particularly aimed at therapeutic and prophylactic treatments of animals, and more particularly, humans. The term "preventing" is art-recognized, and when used in relation to a condition, such as cancer, is well understood in the art, and includes administration of a composition which reduces the frequency of, or delays the onset of, symptoms of a medical condition (here, cancer) in a subject relative to a subject who does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

In certain embodiments of such methods, one or more miniature proteins thereof can be administered, together (simultaneously) or at different times (sequentially). In addition, a miniature protein can be administered with another type of compounds for treating cancer (see below). The two types of compounds may be administered simultaneously or sequentially.

A wide array of conventional compounds have been shown to have anti-tumor activities. These compounds have been used as pharmaceutical agents in chemotherapy to shrink solid tumors, prevent metastases and further growth, or decrease the number of malignant cells. Although chemotherapy has been effective in treating various types of malignancies, many anti-tumor compounds induce undesirable side effects. In many cases, when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

Therefore, the subject miniature protein may be conjointly administered with a conventional anti-tumor compound. Conventional anti-tumor compounds include, merely to illustrate: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

In another related embodiment, the invention contemplates the practice of the method in conjunction with other anti-tumor therapies such as radiation. As used herein, the term "radiation" is intended to include any treatment of a neoplastic cell or subject by photons, neutrons, electrons, or other type of ionizing radiation. Such radiations include, but are not limited to, X-ray, gamma-radiation, or heavy ion particles, such as alpha or beta particles. Additionally, the radiation may be radioactive.

Administration and Pharmaceutical Formulations

Miniature proteins (including variants thereof) of the present invention can be administered in various forms, depending on the disorder to be treated and the age, condition, and body weight of the patient, as is well known in the art. For example, where the miniature proteins are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the agent that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient.

Formulations useful in the methods of the present invention include those suitable for oral, nasal, topical (including buccal and sublingual), rectal, vaginal, aerosol, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes, and the like, each containing a predetermined amount of a therapeutic agent as an active ingredient. A compound may also be administered as a bolus, electuary or paste.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Formulations which are suitable for vaginal administration also include pessaries, tampons, creams, gels, pastes, foams, or spray formulations containing such carriers as are known in the art to be appropriate. Dosage forms for the topical or transdermal administration of a therapeutic agent include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The therapeutic agent can be alternatively administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers.

Transdermal patches have the added advantage of providing controlled delivery of an therapeutic agent to the body. Such dosage forms can be made by dissolving or dispersing the agent in the proper medium. Absorption enhancers can also be used to increase the flux of the therapeutic agent across the skin. The rate of such flux can be controlled by either providing a rate controlling membrane or dispersing the peptidomimetic in a polymer matrix or gel.

Pharmaceutical compositions of this invention suitable for parenteral administration comprise one or more miniature proteins in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

These miniature proteins may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

EXAMPLES

Without further description, it is believed that a person of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

Example 1

Synthesis of DNA-Binding Miniature Proteins

Polypeptides constituting miniature proteins were prepared using solid phase methodology and contain a carboxy-terminal amide and a free amino terminus unless otherwise indicated. High performance liquid chromatography (HPLC) was performed on either a Waters 600E Multisolvent Delivery System with a Waters 490E multiwavelength detector or a Rainin Dynamax SD-200 Solvent Delivery System with a Rainin Dynamax PDA-2 Diode Array Detector.

Solid phase peptide synthesis was performed on a Perseptive BioSearch 9600 peptide synthesizer. Standard research grade argon (Connecticut AirGas) was passed through an OxyClear oxygen scrubber before introduction to the synthesizer. HATU (O-(7-benzotrizol-1-yl)-1,1,3,3,-tetramethyl uronium hexafluorophosphate) was used as the activating reagent without addition of supplemental benzotrizole. Dimethylformamide, piperidine and methylene chloride (Baker) were fresh and stored under nitrogen. Anhydrous dimethylformamide was mixed with diisopropylethylamine (DIPEA, redistilled 0.46 M) to prepare the base activator solution. 9-Fluorenylmethoxycarbonyl (F-moc)-protected amino acids utilized the following side chain protecting groups: O-t-butyl (Asp, Glu); t-butyl (Tyr, Thr, Ser); 2,2,4,6,7-pentamethyldihydrobenzofuran-5-sulfonyl (Pbf) (Arg); t-butoxycarbonyl (Lys); and triphenylmethyl (Cys, His, Asn, Gln). Synthesis was performed on a 0.10 mmol scale using PAL (peptide amide linker) resin (Fmoc-NH$_2$—CH$_2$-(di-m-methoxy,p-O—(CH$_2$)$_4$C(O)-polystyrene) which resulted in an amidated carboxy-terminus. Fmoc-amino acid and HATU were used in four-fold excess (0.4 mmol per coupling). After the final coupling was completed, the Fmoc-protecting group was removed and the resin was washed for the last time. The resin was dried and stored in a desicator until cleavage and deprotection were initiated.

Reverse phase HPLC was performed using eluents composed of mixtures of Buffer A (98% HPLC water, 2% acetonitrile, 0.05% trifluoroacetic acid) and Buffer B (20% HPLC water, 80% acetonitrile, 0.06% trifluoroacetic acid). All HPLC solvents were filtered through a 0.2 micron filter prior to use. Solvents and chemicals for peptide synthesis were obtained from Aldrich and Perseptive Biosearch unless stated otherwise. Peptides were lyophilized using a Savant SC100 Speed Vacuum instrument. Denaturing sodium dodecyl sulfate-polyacrylamide gel electrophoresis (SDS-PAGE) analysis was performed with a Pharmacia PhastGel system using High Density gels (20% acrylamide soaked in glycerol). Amino acid analysis was assayed on a Beckman Analyzer.

For deprotection and purification of PPEBP1$^{SH}$, PAL resin (15 mg) containing protected PPEBP1$^{SH}$ was allowed to react for five hours at room temperature in a deprotection cocktail (84% trifluoroacetic acid, 4% phenol, 4% ethanedithiol, 4% thioanisole and 4% water). The solvent was removed by blowing a stream of nitrogen over the solution until the volume reached approximately 0.25 ml. Diethylether (1 ml) and dithiothreitol (20 mg) were added to precipitate the peptide and stabilize the cysteine. The supernatant was removed after centrifugation and the precipitate dried. The crude peptide was dissolved in 1 ml phosphate-buffered saline (pH 7.5) with added dithiothreitol (5 mg) and filtered with a 0.2 micron filter. The peptide was purified by reverse phase HPLC (Vydac semipreparative 300 Å C18, 5 microns, 10.0×250 mm) using a 120 minute linear gradient of 100-30% Buffer A in Buffer B. The peptide eluted at 49.3 minutes using a flow rate of 4 ml/min and was analyzed by electrospray ionization mass spectrometry. The predicted and observed masses were 4729.4 and 4730.0, respectively.

For preparation of PPEBP1$^{SR}$, 0.080 mg of PPEBP1$^{SH}$ was dissolved in 0.50 ml of 2 mg/ml (15 mM) 2-bromoacetamide in 20 mM sodium phosphate buffer (pH 7.5). The reaction was allowed to proceed for thirty minutes at room temperature. The peptide was purified by reverse phase HPLC (Rainin analytical 100 Å C18, 5 microns, 4.6×250 mm) using a forty minute linear gradient of 100-30% Buffer A in Buffer B. The peptide eluted at 23.3 minutes using a flow rate of 1 ml/min and was characterized by electrospray ionization mass spectrometry and amino acid analysis. AAA expected: Ala5 Asx5 CmCys1 Glx2 Phe1 Gly4 His0 Lle0 Lys3 Leu2 Met0 Pro4 Arg8 Ser1 Thr1 Val2 Tyr2, found Ala5.2 Asx4.8 CmCys0.6 Glx2.0 Phe1.0 Gly4.1 His0 Lle0 Lys2.9 Leu2.0 Met0 Pro3.7 Arg6.9 Ser1.8 Thr0.8 Val2.0 Tyr1.8; mass predicted 4786.4, found 4787.1.

For deprotection and purification of PPEBP2$^{SH}$, PAL resin (10 mg) containing protected PPEBP2$^{SH}$ was allowed to react for seven hours at room temperature in the deprotection cocktail and the solvent was removed. Diethylether (1 ml) and dithiothreitol (20 mg) were added, the supernatant was removed after centrifugation and the precipitate dried. The crude peptide was dissolved in 1 ml phosphate-buffered saline (pH 7.5) containing 5 mg fresh dithiothreitol and filtered. The peptide was purified by reversed phase HPLC (Vydac semipreparative 300 Å C18, 5 microns, 10.0×250 mm) using a linear 120 minute gradient of 100-50% Buffer A in Buffer B. The peptide eluted at 67.8 minutes using a flow rate of 4 ml/min and was characterized by electrospray ionization mass spectrometry: mass predicted 4654.2, found 4653.6.

For preparation of PPEBP2$^{SR}$, 0.070 mg of PPEBP2$^{SH}$ was dissolved in 0.50 ml of 2 mg/ml (15 mM) 2-bromoacetamide in 20 mM sodium phosphate buffer (pH 7.5). The reaction was allowed to proceed forty minutes at room temperature. The peptide was purified by reverse phase HPLC using a four minute linear gradient of 100-30% Buffer A in Buffer B (Rainin analytical 100 Å C18, 5 microns, 4.6×250 mm). PPEBP2$^{SH}$ eluted at 24.9 minutes using a flow rate of 1 ml/min, and was characterized by electrospray ionization mass spectrometry and amino acid analysis. AAA expected: Ala5 Asx6 CmCys1 Glx3 Phe1 Gly4 His0 Lle0 Lys3 Leu2 Met0 Pro4 Arg7 Ser2 Thr1 Val2 Tyr1, found Ala5.0 Asx5.8 CmCys0.9 Glx3.0 Phe1.0 Gly4.0 His0 Lle3.0 Lys3.0 Leu2.1 Met0 Pro4 Arg7 Ser2 Thr1 Val2 Tyr1; mass predicted 4711.3, found 4710.8.

For deprotection and purification of EBP1$^{SH}$, PAL resin (12 mg) containing protected EBP1$^{SH}$ was allowed to react for six hours at room temperature in the deprotection cocktail and treated as described for PPEBP1$^{SR}$. The crude peptide was dissolved in 1 ml phosphate-buffered saline (pH 7.5) with added dithiothreitol (5 mg) and filtered. The peptide was purified by reversed phase HPLC (Vydac semipreparative 300 Å C18, 5 microns, 10.0×250 mm) using a 72 minute linear gradient of 100-70% Buffer A in Buffer B. EBP1$^{SH}$ eluted at 49.6 minutes using a flow rate of 1 ml/min and was characterized by electrospray ionization mass spectrometry: mass predicted 3346.9, found 3346.2.

For preparation of EBP1$^{SR}$, 150 micrograms of EBP1$^{SH}$ was dissolved in 0.50 ml of 2 mg/ml (15 mM) 2-cromoacetamide in 20 mM sodium phosphate buffer (pH 7.5). The reaction was allowed to proceed thirty minutes at room temperature. The peptide was purified by reverse phase HPLC (Rainin analytical 100 Å C18, 5 microns, 4.6×250 mm) using a 40 minute linear gradient of 100-30% Buffer A in Buffer B. EBP1$^{SR}$ eluted at 17.0 minutes using a flow rate of 1 ml/min and was characterized by electrospray ionization mass spectrometry and amino acid analysis. AAA expected: Ala4 Asx3 CmCys1 Glx1 Phe1 Gly2 His0 Lle0 Lys3 Leu2 Met0 Pro0 Arg8 Ser1 Thr0 Val1 Tyr1, found Ala3.9 Asx3.0 CmCys0.9 Glx1.0 Phe1.0 Gly2.1 His0 Lle0 Lys2.8 Leu2.0 Met0 Pro0 Arg6.9 Ser0.9 Thr0 Val1.0 Tyr1.0; mass predicted 3404.0; found 3403.7.

For C/EBP$_{152}$, a stock solution of the purified C/EBP peptide was prepared by dissolution in phosphate-buffered saline with 10 mM dithiothreitol. The solution was heated to 95° C. and allowed to slowly cool to room temperature in order to assure reduction of the cysteine near the carboxy terminus of the peptide. The peptide was then used immediately for EMSA analysis. The peptide was characterized by amino acid analysis. AAA expected: Ala8 Asx18 Glx18 Phe5 Gly6 His0 Lle4 Lys14 Leu12 Met3 Pro6 Arg13 Ser15 Thr7 Val9 Tyr2, found Ala9.2 Asx16.9 Glx18.0 Phe4.5 Gly7.0 His0 Lle3.8 Lys14.2 Leu11.3 Met2.7 Pro6.0 Arg10.8 Ser13.0 Thr7.0 Val8.0 Tyr1.7.

Example 2

Binding of Miniature Proteins to DNA

Miniature protein-binding to DNA was measured using an electrophoretic mobility shift assay performed in a Model SE600 Dual-Controller Vertical Slab Unit (Hoefer) using 14×16 cm gel plates. Temperature was controlled using a constant temperature bath. Reactions were performed in a binding buffer composed of 137 mM NaCl, 2.7 mM KCl, 4.3 mM Na$_2$HPO$_4$, 1.4 mM NaH$_2$PO$_4$ (pH 7.4), 1 mM EDTA, 0.1% NP-40, 0.4 mg/ml BSA (non-acetylated) and 5% glycerol. For experiments involving the bZIP peptide C/EBP$_{152}$, the binding buffer was supplemented with 2 mM dithiothreitol. Serial peptide dilutions were performed as 1:1 dilutions with binding buffer. In general, 0.002 ml of gamma $^{32}$P-labeled, double-stranded DNA (CRE$_{24}$, hsCRE$_{24}$, C/EBP$_{24}$ or hsCEBP$_{24}$; final concentration ≦50 pM in binding buffer; final concentration ≦5 pM for peptides with K$_{app}$<500 pM) in binding buffer were added to 0.008 ml of a serial peptide dilution on ice. Peptide-DNA mixtures were incubated for thirty minutes on ice and then applied to a pre-equilibrated, native polyacrylamide gel (8% acrylamide:bisacrylamide) prepared in 10 mM Tris buffer (pH. 8.1). Gels were allowed to run 0.75 to 1.5 hours at 500 V and were dried on a Model SE1160 Drygel Sr. gel dryer (Hoefer). The gels were analyzed using a Storm 840 Phosphorimager (Molecular Dynamics). Amounts of free and bound DNA were quantified and analyzed using the program KaleidaGraph 3.0 (Synergy Software). Dissociation constants were determined by fitting the data to the Langmuir equation=$c[(1+(K_{app}/peptide_T^n))^{-1}]$ where n=1 for PPEBP$^{SR}$ and EBP$^{SR}$ and n=2 for C/EBP$_{152}$. In these equations, theta=cpm in protein-DNA complex/(cpm in protein-DNA complex+cpm free DNA); peptide$_T$=the total peptide concentration and c is an adjustable parameter representing the maximum value of theta ($c \leqq 1$; for many peptides c was defined as 1). Values reported represent the average of at least three independent trials±the standard error. Error bars on the plots represent the standard error for each data point.

For determination of binding stoichiometry, binding reactions were performed in the same buffer used for EMSA experiments. Each reaction contained 200 nM hsCRE$_{24}$ and between 25 nM to 1600 nM PPEBP1$^{SR}$. The hsCEBP$_{24}$ concentration was determined by measuring the absorbance of each single stranded oligonucleotide at 260 nm. One strand of each duplex was labeled with gamma-$^{32}$P. A small amount (0.010 ml) of labeled DNA was added to a 0.002 mM stock of the same strand. The ensure that the labeled strand annealed completely to its complement, an excess of cold complementary strand was added and the mixture was allowed to anneal by heating to 95° C. for two minutes and slowly cooling to room temperature. Labeled hsCEBP$_{24}$ was added to the PPEBP1$^{SR}$ solution and the reaction incubated at 4° C. for thirty minutes before being applied to a native 8% (80:1 acrylamide:bisacrylamide) prepared in 10 mM Tris buffer (pH=8.0 at 4° C.). The gels were suspended in a chamber containing 10 mM Tris buffer that was kept at 4° C. by immersion in a water-circulating temperature bath. The gels were dried and quantified with a Phosphorimager (Molecular Dynamics).

No significant DNA binding was detected with peptides PPBR0$^{SR}$ (SEQ ID NO: 8), PPBR10$^{SR}$ (SEQ ID NO: 9) and PPBR11$^{SR}$ (SEQ ID NO: 10) which lacked one or more of these DNA-contact residues. High-affinity DNA binding was observed with a peptide that contained these three residues: The equilibrium dissociation constant ($K_d$) of the PPBR2$^{SR}$ (SEQ ID NO: 11) binding to hsCRE was 5 nM under conditions of physiological ionic strength. DNA affinity was enhanced further by selective alanine substitutions that increased the overall alpha-helical propensity of the peptide, producing the PPBR4$^{SR}$-hsCRE$_{24}$ complex whose $K_d$ was 1.5 nM under identical conditions. Formation of the PPBR4$^{SR}$-hsCRE$_{24}$ complex was unaffected by high concentrations of poly (dIdC)-(dIdC) (Garner & Revzin, (1981) Nucl. Acids Res. 9, 3047-3048; Fried & Crothers, (1981) Nucl. Acids Res. 9, 6505-6506) or a scrambled CRE site (NON) indicating that the high stability of PPBR4$^{SR}$-hsCRE$_{24}$ was not due primarily to nonspecific ionic interactions. Circular dichroism experiments indicated that like bZIP peptides (Weiss et al., (1990) Nature 347, 575-578; O'Neil, (1990) Science 249, 774-778), no detectable changes in secondary structure occurred. PPBR4$^{SR}$ (SEQ ID NO: 12) attained a fully alpha-helical conformation only in the presence of specific DNA (The CD spectrum of PPBR4$^{SR}$ was unchanged between 0.001 and 0.020 mM, indicating that no detectable changes in secondary structure occurred in this range. Addition of hsCRE DNA significantly increased the alpha-helix content of PPBR4$^{SR}$ while smaller changes were observed upon addition of hsCEBP DNA.

Although others have described monopartite DNA recognition by basic segment peptides, the affinities reported have been only moderate (60 nM-0.003 mM), and the complexes are stable only in very low ionic strength buffers (Park et al., (1996) J. Am. Chem. Soc. 118, 4235-4239; Morii et al., (1996) J. Am. Chem. Soc. 118, 10011-10012). PPBR4$^{SR}$ represents the first example of high affinity, monopartite, major groove recognition at physiological ionic strength.

Example 3

Role of Hydrophobic Core in Miniature Protein-Binding to DNA

The contribution of hydrophobic core formation on PPBR4$^{SR}$-hsCRE$_{24}$ complex stability was examined utilizing UV circular dichroism experiments. Circular dichroism spectra were recorded in PBS on an Aviv-202 CD spectrometer and were background corrected but not smoothed. Wavelength scans were performed at 4° C. between 200 and 260 nm at 1 nm intervals with a recording time of five seconds at each interval. Thermal denaturation curves were measured at 222 nm between 4° C. and 98° C. with 2° C. steps and one minute equilibration at each temperature. Mean residue ellipticity and percent helicity were calculated from the value at 222 nm after background correction.

G$_{27}$ lacked the polyproline helix and turn, whereas PPBR4-delta$^{SR}$ contained D-tryptophan at position four and leucine at position thirty-one. Modeling studies suggested that these substitutions would disrupt core formation by kinking the polyproline or the alpha-helix. The stability of the G$_{27}$-hsCRE$_{24}$ and PPBR4-delta$^{SR}$-hsCRE$_{24}$ complexes were 3.1 and 3.2 kcal·mol$^{-1}$ lower, respectively, than that of PPBR4$^{SR}$-hsCRE$_{24}$ complex. These data indicate that hydrophobic core formation stabilized the PPBR4$^{SR}$-hsCRE$_{24}$ complex by as much as 3 kcal·mol$^{-1}$.

Example 4

DNA Sequence Specificity of Miniature Protein Binding

The sequence specificity of PPBR4$^{SR}$ was examined by comparing its affinity for hsCRE$_{24}$ (SEQ ID NO: 13) to that for hsCEBP$_{24}$ (SEQ ID NO: 4), a sequence containing the half-site recognized by C/EBP bZIP proteins (Agre et al., (1989) Science 246, 922-926) using the electrophoretic mobility shift assay described above. This half-site (ATTGC) (SEQ ID NO: 66) differs from the CRE half-site (ATGAC) (SEQ ID NO: 65) by two base pairs and provides an excellent measure of base pair specificity (Suckow et al., (1993) EMBO J. 12, 1193-1200; Johnson, (1993) Mol. Cell. Biol. 13, 6919-6930). PPBR4$^{SR}$ displayed remarkable specificity for hsCRE$_{24}$. The specificity ratio $K_{rel}$ ($K_d$(hsCRE)/$K_d$(hsCEPB)) describing preferred recognition of hsCRE$_{24}$ by PPBR4$^{SR}$ was 2600 (delta,delta-G=−4.4 kcal·mol$^{-1}$). By contrast, G$_{56}$ which comprised the bZIP element of GCN4, displayed low specificity. Specificity ratios of 118 and 180 were observed for binding of CRE$_{24}$ (SEQ ID NO: 3) by G$_{56}$ in preference to CEBP$_{24}$ (SEQ ID NO: 4) and hsCRE$_{24}$ (SEQ ID NO: 1) in preference to hsCEBP$_{24}$ (SEQ ID NO: 2) (delta, delta-G=−2.6 and −2.9 kcal·mol$^{-1}$, respectively). The relative specificities of G$_{56}$ and PPBR4$^{SR}$ were most recognizable when one considered the concentration of each protein required to bind one-half of the two DNA. For PPBR4$^{SR}$, this difference corresponded to a ratio of 2600, whereas for G$_{56}$, it corresponded to a ratio of eleven. PPBR4$^{SR}$ more readily distinguished the two base pair difference between hsCRE$_{24}$ and hsCEBP$_{24}$ than G$_{56}$ distinguished CRE$_{24}$ from hsCEBP$_{24}$, two sequences that differed by six of ten base pairs. These comparisons emphasize that PPBR4$^{SR}$ was considerably more selective than was GCN4, the protein on which its design was based.

Example 5

Construction of Synthetic Genes Encoding a Miniature Protein

As described into detail below, the phage display vector pJC20 was derived from the monovalent phage display vector pCANTAB5E (Pharmacia). pJC20 was prepared by inserting a synthetic gene encoding aPP between the unique Sfi I and Not I restriction sites found in pCANTAB5E. The synthetic aPP gene contained codons for optimal protein expression in *E. coli* and four restriction sites (Xma I, Age I, Bgl II and Pst I) absent in pCANTAB5E. These restriction sites allow for the efficient construction of genes encoding a variety of discrete miniature proteins as well as for the introduction of genetic diversity. The vector pJC21 was prepared by inserting a synthetic gene encoding residues 18-42 of PPBR4 between the unique Bgl II and Not I sites in pJC20. The identities of pJC20 and pJC21 were confirmed by automated DNA sequencing A synthetic gene for aPP was constructed using codons chosen to optimize expression in *E. coli* and incorporated four unique restriction sites to facilitate cassette mutagenesis. The 142 base pair duplex insert was generated by use of mutually primed synthesis and the oligonucleotides APP.TS (CTA TGC GGC CCA GCC GGC CGG TCC GTC CCA GCC GAC CTA CCC GGG TGA CGA CGC ACC GGT TGA AGA TCT GAT CCG TTT CTA CAA CGA CCT GCA GCA GTA CCT GAA CGT TGT TAC CCG TCA CCG TTA CGC GGC CGC AGG TGC G) (SEQ ID NO: 39) and APP.BS (CTA TGC GGC CCA GCC GGC CGG TCC GTC CCA GCC GAC CTA CCC CGG GTG ACG ACG CAC CGG TTG AAG ATC TGA TCC GTT TCT ACA ACG) (SEQ ID NO: 40) which overlap at nineteen base pairs. The reaction mixture (20 ml) contained 8 pmol APP.TS, 8 pmol APP.BS, 1× ThermoPol buffer (New England Biolabs), 2 mg BSA, 1 mM dNTPs, 25 mCi [gamma-$^{32}$P] ATP, 5 mM MgSO$_4$ and 2 ml Vent(exo-) DNA polymerase and was incubated at 94° C. for thirty seconds, 60° C. for thirty seconds and 72° C. for one minute. The major reaction product was purified from a denaturing (8 M urea) 10% acrylamide (29:1 acrylamide:bis-acrylamide) gel and amplified by PCR in a 0.100 ml volume containing 1,500 pmol of the primers CTA TGC GGC CCA GCC GGC CGG (SEQ ID NO: 41) and CGC ACC TGC GGC CGC GTA ACG (SEQ ID NO: 42), 0.010 ml template, 0.25 mM dNTPs, 5 mM MgSO$_4$, 1× ThermoPol buffer (New England Biolabs) and 2 ml Vent(exo-) (New England Biolabs). The PCR reaction was subjected to thirty cycles of denaturation (94° C. for thirty seconds), annealing (60° C. for thirty seconds) and extension (72° C. for one minute). The insert was digested with Sfi I at 50° C. in NEB buffer two for four hours. This buffer was then supplemented with NaCl to a final concentration of 100 mM and with Tris-HCl to a final concentration of 50 mM before digestion with Not I for four hours at 37° C. The resulting insert was ligated into the vector pCANTAB-5E (Pharmacia) in a reaction containing 800 units T4 DNA ligase (New England Biolabs), 50 mM Tris-HCl (pH 7.8), 10 mM MgCl$_2$, 10 mM DTT, 25 mg/ml BSA, 1 mM ATP, 250 ng pCANTAB5E at 16° C. for one and a half hours. The ligation products were transformed by electroporation into TG1 *E. coli* and the resulting plasmid designated pJC20. A synthetic gene for PPBR4 was generated by replacing fifty-seven base pair at the 3' end of the aPP synthetic gene (in pJC20) with the sequence encoding the C-terminal twenty-five amino acids of PPBR4.

The oligonucleotides PPBR4$^{TS}$ (GAT CTG AAG CGC TTT CGT AAC ACC CTG GCT GCG CGC CGT TCC CGT GCA CGT AAA GCT GCA CGT GCT GCA GCT GGT GGT TGC GC) (SEQ ID NO: 43) and PPBR4$^{BS}$ (CGC ACC TGC GGC CGC GCA ACC ACC AGC TGC AGC ACG TGC AGC TTT ACG TGC ACG GGA ACG GCG CGC AGC CAG GGT GTT ACG AAA GCG CTT CAG ATC TTC AAC C) (SEQ ID NO: 44) were annealed and phosphorylated on the 5' end to form the PPBR4 insert. The PPBR4 insert was ligated into pJC20 that had been previously digested with Bgl II and Not I and dephosphorylated with enzyme. The ligation reaction mixture contained 800 units T4 DNA ligase in 50 mM Tris-HCl (pH 7.8), 10 mM MgCl$_2$, 10 mM DTT, 25 mg/ml BSA, 1 mM ATP, 90 ng digested pCANTAB-5E and 8 ng annealed insert. After reaction, the ligation mixture was transformed into electro-competent TG1 *E. coli*. The plasmid was designated pJC21. The sequences of all final constructs were confirmed by automated sequencing.

Example 6

DNA-Binding Miniature Protein Phage Library Construction

A 10 ml volume of 2×YT containing 100 mg/ml ampicillin and 2% glucose was innoculated with a 500 ml overnight culture of TG-1 *E. coli* containing the plasmids pJC20 or pJC21 and shaken at 37° C. to an OD$_{600}$=0.8. 4×10$^{10}$ pfu of M13 KO7 helper phage were added and shaking continued for an additional one hour. Cells were pelleted for fifteen minutes at 5000×g and resuspended in an equal volume of 2×YT containing 100 mg/ml ampicillin and 50 mg/ml kanamycin and grown for ten hours with shaking. Cells were pelleted by centrifugation at 5000×g for twenty minutes and the phage supernatant filtered through a 0.45 micron filter before precipitation with PEG/NaCl (20% w/v PEG-8000, 2.5 M NaCl in ddH$_2$O) on ice for forty-five minutes. Phage were pelleted at 13000×g for thirty minutes at 4° C. and resuspended in binding buffer.

Example 7

Expression of Miniature Proteins by M13 Phage

As a first step towards displaying miniature proteins on the surface of phage, the inventors sought to verify that aPP was expressed from the synthetic gene, which is under the control of a lac promoter. To this end, TG-1 *E. coli* harboring pJC20 were induced with isopropylthiogalactoside (IPTG), lysed and the cell lysates probed with a rabbit anti-aPP antibody (Peninsula Laboratories #RGG-7194) as described below.

TG1 cells containing pJC20 were grown for one hour at 30° C. in 2×YT containing ampicillin at 100 mg/ml and 2% glucose. Cells were pelleted by centrifugation at 5000×g and resuspended in an equal volume of 2×YT containing 100 mg/ml ampicillin and 1 mM IPTG, grown for three hours at 30° C. and then lysed by boiling in SDS sample buffer. Aliquots were loaded onto a Pharmacia Phast HOMO 20 gel and electrphoresed at 95 V until the solvent front ran off the gel. Proteins in the gel were transferred to an Immobilon-P membrane at 65° C. for one hour. The membrane was blocked for thirty minutes with TBST (20 mM Tris-HCl (pH 8.0), 150 mM NaCl, 0.05% Tween-20) containing 0.5% BSA and then incubated with a 1:10000 dilution of rabbit anti-aPP (Peninsula Laboratories RGG-7194) provided at 4 mg/ml. The membrane was then washed three times (five minutes per wash) with TBST and then incubated with TBST containing a goat anti-rabbit alkaline phosphatase conjugate (Santa Cruz sc-2007) at a 1:1000 dilution. After three five minute washes with TBST and a single wash with TBS (TBST lacking Tween-20), the membrane was stained with VISTRA ECF (Pharmacia) and visualized at 405 nm on a STORM 850 Phosphoimager (Molecular Dynamics).

For Western blots on phage particles, 10 ml of phage were produced and precipitated with PEG/NaCl as described above. The phage were then resuspended in 1 ml ddH$_2$O, precipitated with 200 ml of PEG/NaCl, resuspended in 100 ml ddH$_2$O and heated to 95° C. in SDS sample buffer for ten minutes. The phage proteins were then applied to a 10% SDS gel (29:1 acrylamide:bisacrylamide) and subjected to electrophoresis at 20 mA in Tris-glycine electrophoresis buffer until the solvent front ran off the gel. The separated proteins were transferred to an Immobilon-P membrane (Millipore) at 20 V for four hours using a TE62 unit (Pharmacia) containing Towbin buffer (20% MeOH, 25 mM Tris-HCl (pH 8), 192 mM glycine, 0.1% SDS (w/v)) at 4° C. After blocking with 5% nonfat milk in TBST for sixteen hours and washing twice (five minutes per wash) with TBST, the membrane was probed for thirty minutes with anti-aPP in TBST supplemented with 2.5% nonfat milk. The membrane was washed three times (five minutes per wash) with TBST, then exposed to a goat anti-rabbit antibody-alkaline phosphatase conjugate (Santa Cruz sc-2007) at a 1:5000 dilution in TBST supplemented with 2.5% nonfat milk for fifteen minutes. After washing three times (five minutes per wash) with TBST and two times (five minutes per wash) with TBS the membrane was stained with VISTRA ECF (Pharmacia) and visualized at 405 nm on a STORM 850 phosphorimager (Molecular Dynamics).

These experiments demonstrate clear evidence for IPTG-inducible expression of aPP fused to the minor capsid protein III of M13 bacteriophage. To investigate whether this fusion protein was assembled into viable phage particles, purified phage were, phage proteins resolved using SDS-PAGE and probed with the rabbit anti-aPP antibody. The Western blot clearly shows that the fusion protein containing aPP and protein III is incorporated into fully assembled M13 phage particles. No signal was observed when phage produced from pJC21 bearing cells were probed with the rabbit anti-aPP antibody Example 8

Functional Selection of DNA-Binding Miniature Proteins on Phage

As a first step towards the optimization of PPBR4, the inventors confirmed that phage displaying PPBR4 could be selected over phage bearing aPP when sorted on the basis of specific DNA-binding. Phage displaying either PPBR4 or its progenitor aPP were panned against magnetic beads coated with a twenty-four base pair duplex oligonucleotide containing the five base pair sequence recognized by PPBR4, half site CRE (hsCRE, ATGAC). The DNA was attached to streptavidin coated beads through a 3' biotin TEG (triethyleneglycol) linker (Glen Research). Panning was performed essentially as previously described and as set forth below (Choo & Klug, (1994) Proc. Natl. Acad. Sci. USA 91, 11163-11167).

For panning experiments, 0.5 mg of streptavidin-coated M-280 magnetic beads (Dynal) were washed six times with 50 ml of 2×B+W buffer (10 mM Tris-HCl (pH 7.5), 1 mM EDTA, 2.0 M NaCl). Each wash step was performed for two minutes. The beads were blocked by incubation in 50 ml of 1×B+W containing 6% nonfat milk for fourteen hours. The beads were then washed five times with 50 ml of 1×B+W and resuspended in 50 ml of 1×B+W containing approximately 1 mM duplex hsCRE242 carrying a 3' biotin label on one strand for twelve minutes. This procedure loaded approximately 75 pmol DNA per mg bead. The beads were then washed five times with 50 ml of phage binding buffer (phosphate buffered saline supplemented with 0.4 mg/ml BSA, 0.1% NP-40 and 2.5 mg of poly-dIdC). 1010 phage in a volume of 0.4 ml were added to the beads at 4° C. and incubated with rotation on a Labquake shaker rotisserie for two hours. Beads were washed five times for five minutes at 4° C. with wash buffer (phage binding buffer lacking poly-dIdC). Bound phage were eluted by the addition of wash buffer containing 4 M NaCl and an increase in temperature to 25° C. for two hours. 200 ml of the elution and 200 ml of phage not subject to panning were used to infect 7 ml of log phase TG-1 *E. coli*. After one hour, serial dilutions of infected cells were plated on SOBAG (SOB media supplemented with ampicillin to 100 mg/ml and 2% glucose) and grown for twelve hours at 30° C. Values of percent retention were calculated where percent retention= (output titer/input titer)×100.

In the present experiments, wash conditions were optimized to maximize differential retention of phage displaying PPBR4 and phage displaying aPP. In phosphate buffered saline (PBS) supplemented with 0.1% NP-40, 0.4 mg/ml BSA and 2.5 µg/ml poly-dIdC, the percent retention of PPBR4 phage on hsCRE beads was ten times greater than that of aPP phage. This result indicates that miniature proteins generated by protein grafting can be functionally selected on M13 phage.

Example 9

Isolation of Highly Selective DNA-Binding Miniature Proteins

Two phage libraries were created essentially as described in the previous examples to identify appropriately folded PPBR4 analogs that would bind with higher affinity and specificity. The members of libraries A and B differ from PPBR4 at three (library A) (SEQ ID NO: 15) or four (library B) (SEQ ID NO: 16) positions on the PPII helix. The proline residues retained at positions two and five of library A are highly conserved among PP-fold proteins. It was anticipated that retention of these two prolines would effectively constrain the conformational space available to library A members and that most would contain N-terminal PPII helices. Such conformational constraints are absent in library B, acknowledging that there may be many ways to stabilize DNA-bound alpha-helices.

Since the amino acids at positions two and five of library B are not restricted to proline, it was anticipated that this library would sample a larger fraction of available phi-psi space. Phage were sorted for three rounds on the basis of their ability to bind an oligonucleotide duplex containing the sequence ATGAC (hsCRE). To favor identification of sequences that bound hsCRE with high affinity at ambient temperature, two rounds of selection at 4° C. were followed by a single round at room temperature. By the final round, library A phage were retained at a level only comparable to PPBR4 phage and were not considered further. Library B phage were retained at a level comparable to PPBR4 phage after the first round, but at levels fifteen to sixteen times better than PPBR4 phage after the subsequent two rounds. Twelve library B clones were sequenced after round three. Six sequences (p007, p009, p011, p012, p013, and p016) were synthesized and the DNA-binding properties of four analyzed in detail.

Quantitative electrophoretic mobility shift experiments were performed as described in the previous examples to assess the DNA affinities of p007, p011, p012, and p016. All peptides tested bound hsCRE as well or better than did PPBR4 or $G_{27}$ (the isolated basic region of GCN4). At 4° C., p011 and p012 bound hsCRE with affinities of 1.5±0.2 nM and 2.5±0.5 nM, whereas p016 bound hsCRE with an affinity of 300±60 pM. Of particular interest is p007, which bound hsCRE to form an exceptionally stable complex with a dissociation constant of 23±1.2 pM. This peptide bound specific DNA approximately 100-times better than did PPBR4 ($K_d$=1.9±0.2 nM) and approximately 20,000 times better than did $G_{27}$ ($K_d$=410±53 nM). Moreover, at 25° C. p007 bound hsCRE with an affinity of 1.6±0.1 nM. Neither PPBR4 nor $G_{27}$ showed evidence of DNA binding at this temperature. P007 binds specific DNA considerably more tightly than two fingers from the Tramtrack zinc finger protein, which binds five base pairs of DNA with an affinity of 400 nM (Segal & Barbas, (2000) Curr. Op. Chem. Biol. 4, 34-35).

Example 10

Specificity of Highly Selective Miniature Protein DNA-Binding

The specificity of DNA binding was investigated by determining the affinity of p007 for several duplex oligonucleotides containing two base pair changes within the five base pair hsCRE sequence using quantitative electrophoretic mobility shift assays as described in the previous examples. p007 was extremely discriminating, exhibiting a specificity ratio R (defined as the ratio of the dissociation constants of specific and mutated complexes) between 200 and 800 (delta, delta-G=−3.3 to 4.0 kcal mol$^{-1}$). This high level of discrimination was observed across the entire five base pair hsCRE sequence, indicating that no single interaction dominated the free energy of the p007-hsCRE complex and that the binding energy is partitioned across the entire protein-DNA interface. By contrast, at 4° C. PPBR4 discriminates poorly (delta, delta-G=−1.7 kcal mol$^{-1}$) against sequences possessing mutations at the 5' terminus of hsCRE.

To investigate the possibility that DNA sequences other than these four might bind p007 tightly, the affinity of p007 for calf thymus DNA (CT DNA) which possesses a potential binding site in every register on either DNA strand was measured. The average specificity ratio for recognition of hsCRE in preference to any site in CT DNA was 4169. This ratio is considerably greater than the number of potential competitor sites ($4^5$=1024). Whereas the triple zinc finger construct Zif268 and variants thereof selected by phage display fail to uniquely specify one to two base pairs of their nine base pair binding sites (Li et al., (1992) Biochemistry 31, 1245-1253), p007 completely specifies all five base pairs of its target sequence. In fact, even if each possible five base pair competitor site were present at equal molarity to the target site, 80% of the p007 molecules would be bound to hsCRE, despite the effects of mass action.

Example 11

NMR Characterization of Miniature Protein Structure

For NMR Spectroscopy, p007 was dissolved in 90% $H_2O$/10% $D_2O$ containing 4 mM KCl, 205 mM NaCl, 6.5 mM $Na_2HPO_4$, 2.1 mM $KH_2PO_4$ (pH 7.4). Peptide concentration was approximately 1.5 mM. Chemical shifts were referenced in ppm from internal 3-(trimethylsilyl)propionic-2,2,3,3-d4 acid, sodium salt. All spectra were recorded on a Varian 800 MHz Inova instrument at 2° C. with a sweep width of 9000 Hz. NOESY experiments were performed using a waterflip-watergate pulse sequence for water suppression with 4096t2×500t1 complex points. Mixing times of 50, 150 and 300 ms were acquired. DQF-COSY spectra (60 ms mixing time) were acquired with 2048t2×300t1 complex points. Data was processing was performed on a Silicon Graphics Workstation using Felix 98 (MSI). Prior to Fourier transform of the free induction decays, a gaussian window function was applied to NOESY spectra, while a Kaiser window function was applied to DQF-COSY spectra. The digital resolution of the NOESY spectra was 2.2 Hz/pt. DQF COSY data was zero filled to yield a 8192×8192 matrix with a digital resolution of 1.1 Hz. Spectra were assigned by standard methods.

Multidimensional NMR experiments allowed for characterization of the structure of p007 in greater detail. The backbone and side-chain connectivities in p007 were assigned on the basis of reasonably disperse NOESY spectra. The presence of amide-amide cross peaks between residues at positions i and i+3 and i and i+4 defined an alpha-helical conformation for residues 14-30. Eleven long range NOEs between residues 8 and 17, 8 and 20, 7 and 20, 5 and 20, 4 and 27, 2 and 29, 2 and 30 specify a folded structure that superimposes on residues 5-8 and 15-28 of aPP with a backbone rmsd of 1.6 Å. Thus, the main chain folds of p007 and aPP are remarkably similar, with residues 5, 7 and 8 proximal to residue 20 and residues 1 and 2 proximal to residue 30. As in previous studies of pancreatic fold polypeptides (Blundell et al., (1981) 78, 4175-4176), the PPII helix proposed for residues 1-8 of p007 is under-defined by the NMR data. However, in light of the similarity between the aPP and p007 folds, p007 must contain a structure similar to a PPII helix.

Example 12

Protein-Binding Miniature Protein Phage Library Construction

For construction of the aPPBAK library, mutagenesis was carried out using the NNS codon scheme, where N=any base and S=G/C. This scheme codes for all twenty amino acids and the amber stop codon TAG which is suppressed by insertion of glutamine in the *E. coli* SupE strains used. The oligonucleotides BAKLIB: GGT GAC GACGCA CCG GTT GAA GAT CTG ATC CGC TTT GTT NNS CGT CTG CTG NNS TAC ATC NNS GAC NNS ATC AAC CGT CGT GCG GCC GCA GGT GCG (SEQ ID NO: 45) and PBAKLIB: CGC ACC TGC GGC GGCACG ACG (SEQ ID NO: 46) were synthesized and purified by denaturing gel electrophoresis. 400 pmol of each oligonucleotide were annealed in 1× Sequenase buffer (USB) in a total volume of 0.20 ml. The annealed oligonucleotides were converted to duplex DNA by primer extension upon addition of 2.5 mM dNTPs, 1 mg/ml BSA and 50 units Sequenase (USB) and incubation at 37° C. for thirty minutes. The duplex DNA was digested in 1× buffer 3 (New England Biolabs) by the addition of 0.015 ml Bgl II, 0.015 ml Not I, 2.5 mM DTT, 0.1 mg/ml BSA in a total volume of 0.430 ml. The reaction mixture was extracted twice with an equal volume of Tris buffered phenol (pH 8.0) and applied to a 15% acrylamide (29:1 acrylamide:bisacrylamide) gel in 1×TBE at 500 V. The doubly digested product was visualized by ethidium staining, excised and extracted in 1×TE. The insert was ethanol precipitated. 0.12 mg of the vector pJC20 was digested with 0.05 ml of Bgl II, Not I and Pst I in a total volume of 0.60 ml. The digested vector was purified by Chromaspin 1000 size exclusion chromatography (Clonetech) and phenol chloroform extraction followed by ethanol precipitation. Ligations were performed using the Ligation express kit (Clontech) with 830 ng of vector (pJC20) and 14 ng of insert. Transformation by electroporation in to TG-1 E. coli yielded $3 \times 10^6$ transformants. The number of transformants is greater than the theoretical diversity of the library ($32^4 = 1.05 \times 10^6$) and the library is statistically greater than 90% complete. Automated DNA sequencing of twenty clones showed the mutant genes were inserted correctly in all cases.

Example 13

Functional Selection of Protein-Binding Miniature Proteins on Phase

For biopanning of the aPPBAK library, a glutathione coated microtiter plate (Reacti-bind glutathione coated plate #15140, Pierce) was washed three times with 0.20 ml of PBS per wash. Human recombinant Bcl-2 (1-205) was obtained as a soluble GST-fusion from Santa Cruz Biotechnology. 9.0 pmol of Bcl-2 in 0.20 ml of PBS was added to each well and incubated at 4° C. for twelve hours with shaking. The wells were then blocked for three hours with 0.20 ml of TBST containing 5% nonfat dry milk. Before use, the well was washed three times with TBST for five minutes per wash.

Phage were produced, harvested and propagated as described in the previous examples, with the exception that, in rounds three through five, XL1-blue cells were used instead of TG-1 cells to propagate phage particles. This change eliminated problems encountered previously with deletions in later rounds of selection, which are attributed to the Rec A+nature of TG-1 E. Coli. Phage particles were resuspended in 2 ml of TBST. 0.20 ml of phage ($1 \times 10^{10}$ particles) were added to each well and incubated for three hours at 4° C. in the first two rounds of selection and at 25° C. in the final three rounds. The wells were then washed ten times with 0.20 ml of TBST, two minute washes in the first round and five minute washes in subsequent rounds. Washes were performed at the same temperature in the binding reaction. After five rounds of selection, sixteen clones were sequenced by automated DNA sequencing.

The phage library BAKLIB was subjected to five rounds of panning against immobilized GST-Bcl-2. The percent retention of the phage library increased 225-fold over the course of the selection from 0.01% in the first round to 2.25% in the fifth round. This increase in retention underestimates the improvement of library retention because the final round was carried out at 25° C. while the first round was performed at 4° C. After five rounds sixteen phagemid library clones were sequenced. The selected sequences (FIG. 1) show a high degree of convergence (SEQ ID NO: 30). Seven distinct sequences were isolated with four sequences represented multiple times. Interestingly, residue 28 in the library, which corresponds to $I_{81}$ of Bak, is mutated to F in eleven of sixteen round five clones, although it was fixed in the initial pool. This result indicates that within the context of the scaffold, $F_{28}$ is better at binding into the hydrophobic pocket of Bcl-2 than $I_{28}$. Eleven of sixteen sequences contain glycine at positions 75 and 82 as in Bak. Indeed, one sequence that was represented two of sixteen times contained residues identical to those of Bak at all four randomized positions, this sequence however, also contained the I-F mutation at position 28. Comparison of the selected sequences to other BH3-containing proteins reveals further similarities. For example, at position 26 of the library, R occurred in seven of the sixteen sequences and R or K is the preferred amino acid at this position (residue 79 in Bak) in most BH3 domains. Similarly, an E at position 31 of the library was selected in six of sixteen sequences, where E/D is the preferred amino acid at the corresponding position of most known BH3 domains.

The similarities of selected amino acids at these positions to those in Bak and other BH3 domains indicates that the sequences of BH3 domains arose from the requirement to bind Bcl-2 family proteins and not for other biological function. Further, it also indicates that the selected peptides bind Bcl-2 in the same hydrophobic pocket as does Bak. Interestingly, one sequence represented twice contained a threonine at position 31 of the library. This residue provides both the methyl group of a valine which could contribute to hydrophobic core formation and a hydroxyl group that could provide a hydrogen bond acceptor like the native D/E residue in BH3 domains. One sequence that appeared twice in the round five clones sequenced contained a single amino acid deletion with respect to the library design that places both the aPP folding residues and the Bcl-2 residues out of register.

Example 14

Synthesis of Protein-Binding Miniature Proteins

Peptides were synthesized on a 0.10 mM scale using Fmoc chemistry. Each peptide contained a free N-terminal amine and a C-terminal amide. Peptides were purified by reverse phase HPLC as described in the previous examples. Two sets of peptides were prepared, peptides 4099-4102 and the Bak peptide (SEQ ID NO: 73). Peptides for fluorescent labeling and subsequence $K_d$ determinations contained an additional carboxy-terminal YC sequence (the Y is derived from the native sequence of Bak), the cysteine of which was labeled with 5-iodoacetamidofluorescein (5IAF). Peptides at a final concentration of 200-400 mM were alkylated on the sulfur atom of C-terminal cysteines by incubation with ten equivalents of 5IAF (Molecular Probes) in 0.20 ml of a 50/50 mixture of DMF and PBS. The labeling reaction was performed in the dark for six hours at room temperature. Alkylation was essentially quantitative as judged by HPLC. Labeled peptides were purified by reverse phase C-18 HPLC. The identifies of the peptides were verified by MALDI-TOF mass spectrometry (Voyager, Perseptive Biosystems). The molecular weights were as expected: p4099 theoretical [MH+]=3907, observed [MH+]=3907; p4100 theoretical [MH+]=4020, observed [MH+]=4020; p4101 theoretical [MH+]=3921, observed [MH+]=3922; p4102 theoretical [MH+]=3901, observed [MH+]=3902; Bak 72-94 theoretical [MH+]=1724, observed [MH+]=1723; p4121-flu theoretical [MH+]=4562, observed [MH+]=4560; p4122 theoretical [MH+]=4675, observed [MH+]=4766; p4123 theoretical [MH+]=4576, observed [MH+]=4577; $p^{4124}$ theoretical [MH+]=4556, observed [MH+]=4556; Bak-flu theoretical [MH+]=2535, observed [MH+]=2535. Peptide concentrations were determined by amino acid analysis.

Example 15

Binding of Miniature Proteins to other Proteins

To measure the equilibrium dissociation constant of Bcl-2 binding to the selected peptides or the Bak BH3 peptide, Bcl-2 was serially diluted from 0.0036 mM in PBS with the fluorescently labeled peptide added at a constant concentration between 0.020-0.040 mM. After equilibration for forty minutes at 4° C., the fluorescein was excited at 492 nm using a PS-220B lamp power supply (Photon Technologies) and the fluorescence emission spectra between 505 and 560 nm recorded on an 814 photomultiplier detection system (Photon Technologies) with a 2 nm stepsize and a one second equilibration time, using 5 nm slit widths. The fluorescence emission maxima at 515 nm for three independent trials were averaged and the dissociation constants calculated as previously described. Similar experiments were used to determine the dissociation constants for the Bak peptide or selected peptides binding carbonic anhydrase II (Sigma) or calmodulin (Sigma). The calmodulin binding was measured in a buffer composed of 20 nM HEPES (pH. 7.2), 130 mM KCl, 1 mM $CaCl_2$ while carbonic anhydrase binding was measured in PBS.

The Bak peptide along with four sequences represented multiple times in the sixteen sequenced clones from round five were chemically synthesized. Bcl-2 binding affinity of the peptides was determined by measuring the change in fluorescence emission of a carboxy-terminal fluorescein label on the peptide as a function of Bcl-2 concentration. To validate this assay the $K_d$ for the Bak peptide binding to Bcl-2 was measured. This $K_d$ was 363 nM±56 nM, consistent with a $K_d$ of 340 nM previously reported for the Bak peptide Bcl-$X_L$ interaction (measured by fluorescence quenching of intrinsic tryptophan in Bcl-$X_L$) and a $K_d$ of about 200 nM reported for the Bak Bcl-2 interaction (measured by fluorescence polarization of a fluorescein labeled Bak peptide). The $K_d$ for the selected peptides were: p4099 $K_d$=352±33 nM, p4100 $K_d$=401±40 nM, p4101 $K_d$=811±20 nM, p4102 3700±1400 nM. The $K_d$ for all the peptides without deletions indicate that they bind significantly better than the mutant p4102 that contains a deletion in the alpha-helix. Within this series of peptides, p4099 (GAGT) binds about two-fold better than p4101 (GAGD), that differs in only a D to T mutation at position 31. p4100 (GRGE) binds with comparable affinity to p4099 indicating that these two peptides represent convergent and equal solutions to forming a protein-protein interface.

In order to compare the specificity of 4099 to the Bak peptide, their interaction with Calmodulin was investigated. Calmodulin is known to bind a range of alpha helices and Carbonic anhydrase II, which has a large hydrophobic cavity. p4099 bound Calmodulin with a $K_d$ of 0.025±0.004 mM, while the Bak peptide bound Calmodulin with a $K_d$ of 0.025±0.004 mM. p4099 bound Carbonic anhydrase II with a $K_d$ of 0.0086±0 mM, the Bak peptide bound Carbonic anhydrase with a $K_d$ of 0.022±0.0046 mM. p4099 discriminates well against these non-specific proteins indicating that the interaction between the peptide and Bcl-2 results from a stereospecific set of VanderWaals contacts.

Example 16

Structure of Protein-Binding Miniature Proteins

Circular dichroism spectra were recorded in PBS on an Aviv 202 CD Spectrometer and were background corrected but not smoothed. Wavelength scans were performed at 4° C. between 200 and 260 nm at 1 nm intervals with a recording time of five seconds at each interval. Bak (72-94), 4099, 4100, 4101, 4102 were used at concentrations of 0.028 mM, 0.0069 mM, 0.0119 mM, 0.014 mM and 0.016 mM respectively. Thermal denaturation curves were measured at 222 nm between 4-98° C. with 2° C. steps and one minute equilibration at each temperature. Peptides were used at the highest concentrations used for the wavelength scans described above. Mean residue elliptcity and percent helicity were calculated from the value at 222 nm after background correction.

The structure of peptides was investigated by far UV circular dichroism as described above. Wavelength scans reveal the previously reported random coil signature for the Bak peptide. In contrast the selected peptides 4099, 4100, 4101, 4102 show minima at 208 and 222 nm, characteristic of alpha-helical content. The mean ellipticity of peptide 4099 was shown to be concentration independent down to the lowest concentration measurable 0.0011 mM. The percentage helicity of p4099 is approximately 60%, consistent with an aPP-like tertiary fold in which residues 14-35 adopt a helical confirmation. This helicity is comparable to that seen for p007, a peptide evolved to bind DNA with high affinity and specificity as described in the previous examples. Thermal denaturation of the peptides was monitored by far UV circular dichroism at 222 nm. p4099 had a cooperative thermal melt with a $T_m$ of approximately 65° C., comparable to the $T_m$ reported for aPP.

Example 17

Miniature Proteins for Inhibiting MDM2-p53 Interactions

MDM2 is the principal cellular antagonist of the tumor suppressor protein p53 (Wu et al., J. Genes Dev. 1993, 7, 1126). MDM2 antagonizes p53 function by sequestering the p53 transcriptional activation domain and targeting it for ubiquitin-dependent degradation by the 26S proteasome. Elevated MDM2 levels are found in a variety of solid tumors containing wild type p53 and there is considerable interest in MDM2 ligands capable of up-regulating p53 activity in vitro or in vivo. The high-resolution structure of the MDM2•p53 activation domain peptide (p53AD) complex reveals an irregular p53AD α-helix nestled into a deep, hydrophobic, MDM2 cleft (Kussie, et al., Science 1996, 274, 948). This structure, along with accompanying mutagenesis data, suggests that complex stability ($K_d$=600 nM) derives predominantly from interactions between three p53AD residues (F19, W23, and L26) and several residues lining the MDM2 cleft.

Residue-by-residue alignment of the α-helical segments of p53 and aPP positions the three critical MDM2 contact residues (F19, W23, and L26) and the five important aPP folding residues (L14, F17, L21, Y24, L25) on the solvent-exposed and solvent-sequestered faces, respectively, of the aPP α-helix. Five remaining α-helical residues were varied across all twenty amino acids to (1) foster additional interactions with MDM2; (2) sustain the aPP fold; and (3) acknowledge the imperfect phi and psi angles found within p53AD bound to MDM2 (Kussie, et al., Science 1996, 274, 948). The M13 phage library (SEQ ID NO: 32) prepared contained $6 \times 10^7$ unique transformants, insuring that it would evaluate DNA sequence space with >83% confidence. Three rounds of selection for binding GST-MDM21 immobilized on glutathione-coated microtiter plates2 led to a 100-fold enrichment in affinity. Several peptides from rounds 2 and 3 (FIG. 2B) were synthesized with a cysteine residue at the C-terminus and labeled with 5-iodoacetamidofluorescein to facilitate fluorescence polarization analysis of MDM2 affinity (all synthetic peptides were purified to homogeneity by HPLC and characterized by MALDI-TOF mass spectrometry and amino acid analysis).

Fluorescence polarization analysis indicated that all selected miniature proteins bound GST-MDM2 in the nanomolar concentration range (FIG. 2). pP53-05, in particular, bound GST-MDM2 to form a complex with an equilibrium dissociation constant ($K_d$) of 99±11 nM, a value that is significantly more favorable than that of the p53AD•MDM2 complex ($K_d$=261±59 nM) (Kussie, et al., *Science* 1996, 274, 948). Thus pP53-05, which contains only 31 residues, binds MDM2 as well or better than 109 residue thioredoxin derivatives that present p53AD (and variants thereof) on an active site loop (Böttger, et al., *J. Med. Chem.* 2000, 43, 3205). The CD spectrum of pP53-05 (2.75 µM) was characterized by negative ellipticity at 208 and 222 nm that was comparable to that of aPP and underwent a cooperative melting transition ($T_m$) at 47° C. (FIG. 3).

Figure 3:
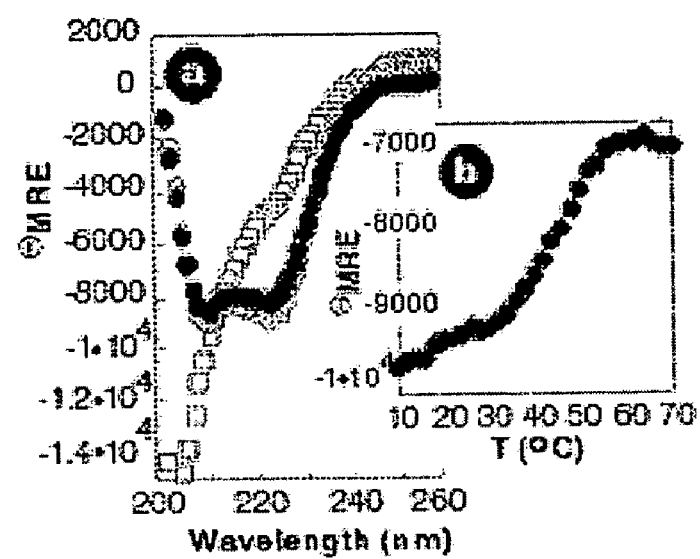
FIG. 3—Circular dichroism analysis of pP53-05 and p53AD secondary structure. Spectra were acquired in 0.5× PBS at 25° C. using a Aviv Model 62DS spectrometer. (a) Plots illustrate the CD spectra of pP53-05 at 2.75 μM (●) and 6.75 μM (○) and p53AD at 3 μM (□). Each data set represents the average of 10 scans. Spectra were background corrected but were not smoothed. (b) Temperature dependence of the CD spectrum of pP53-05. $\Theta_{MRE}$ is in units of deg·cm²·dmol⁻¹.

The specificity of pP53-05 was evaluated by measuring its affinity for several receptors and enzymes that bind helical or hydrophobic peptides or small molecules (FIG. 2). Calmodulin, an EF hand protein known for its ability to bind many α-helical peptides and proteins (Meador, et al., *Science* 1991, 257, 1251), bound pP53-05 in the high micromolar concentration range ($K_d$>275 µM). Similar $K_d$ values characterized the affinity of pP53-05 for the bZIP region of Fos, which forms dimeric complexes with other bZIP proteins (42 µM) (Glover, et al., *Nature* 1995, 373, 257), for carbonic anhydrase, which binds $CO_2$ (298 µM) (Liljas, et al., *Nat. New Biol.* 1972, 235, 131), and for protein kinase A, which binds the α-helical peptide inhibitor pKI (16 µM) (Knighton, et al., *Science* 1991, 253, 414). The large difference ($\Delta\Delta G$=2.8-4.4 kcal·mol$^{-1}$) between the stabilities of these complexes and that of pP53-05•GST-MDM2 suggests that the latter is stabilized by highly stereospecific van der Waals interactions whose energetic benefit exceeds that available through non-specific protein contacts.

To establish whether pP53-05 bound MDM2 in a manner that would inhibit binding of p53AD, we incubated GST-MDM2 and p53AD-Flu with varying concentrations of pP53-05 and monitored the fraction of p53AD-Flu bound at equilibrium (FIG. 2). In the absence of pP53-05, 60% of p53AD-Flu is bound to GST-MDM2 under these conditions. Addition of pP53-05 led to a concentration-dependent decrease ($K_i$=722 nM) in the fraction of p53AD-Flu bound to GST-MDM2. Similar $K_i$ values were determined at shorter and longer incubation times, confirming that equilibrium had been reached. By comparison, competition of p53AD-Flu by unlabeled p53AD was characterized by $K_i$=1.2 µM.

In conclusion, we have shown that protein grafting, in combination with functional selection, provides rapid access to miniature protein ligands for globular protein surfaces. The molecules we describe possess affinities in the nanomolar concentration range and effectively discriminate against other proteins, even those that bind non-selectively to other helical, hydrophobic proteins. The combined features of high affinity, high selectivity and a compact protein fold should enhance the utility of miniature proteins for a wide variety of bioengineering and proteomics applications (Zhang, et al., *Nat. Biotech.* 2000, 18, 71).

Example 18

Miniature Proteins for Inhibiting Protein Kinase A

The design of selective protein kinase inhibitors remains a significant challenge (Bridges, et al., *J. Chem Rev* 2001, 101, 2541-72; Scapin, et al., *Drug Discov Today* 2002, 7, 601-11) because of both sheer numbers (more than 500 different kinases are found in a mammalian cell) and the highly conserved nature of the ATP binding site (Miller, W. T. *Nat Struct Biol* 2001, 8, 16-8). Only a small number of selective kinase inhibitors are known (Bridges, et al., *J. Chem Rev* 2001, 101, 2541-72; Cohen, et al., *Curr Opin Chem Biol* 1999, 3, 459-65; Zimmermann, et al., *Bioorg Med Chem Lett* 1997, 7, 187-92).

The indolocarbazole natural product K252a is a potent, active-site directed inhibitor of many tyrosine and serine/threonine kinases and a common starting point for the discovery of specific kinase inhibitors (Kase, et al., *J Antibiot* 1986, 39, 1059-65; Kase, et al., *Biochem Biophys Res Commun* 1987, 142, 436-40; Hashimoto, et al., *Biochem Biophys Res Comm* 1991, 181, 423-9; Tapley, et al., *Oncogene* 1992, 7, 371-81). We have described a miniature protein design strategy in which the well-folded helix in avian pancreatic polypeptide (aPP) presents short α-helical recognition epitopes. The miniature proteins designed in this manner recognize even shallow clefts on protein surfaces with nanomolar affinities and high specificity (see, e.g., Examples 19-20). Here we demonstrate that designed variants of aPP can also impose specificity on the potent but otherwise non-selective kinase inhibitor K252a by recognizing non-conserved features of the protein surface surrounding the ATP binding pocket. Our results suggest that bifunctional molecules that embody elements of protein surface recognition could represent a viable general strategy for selective kinase inhibition.

Figure 4:
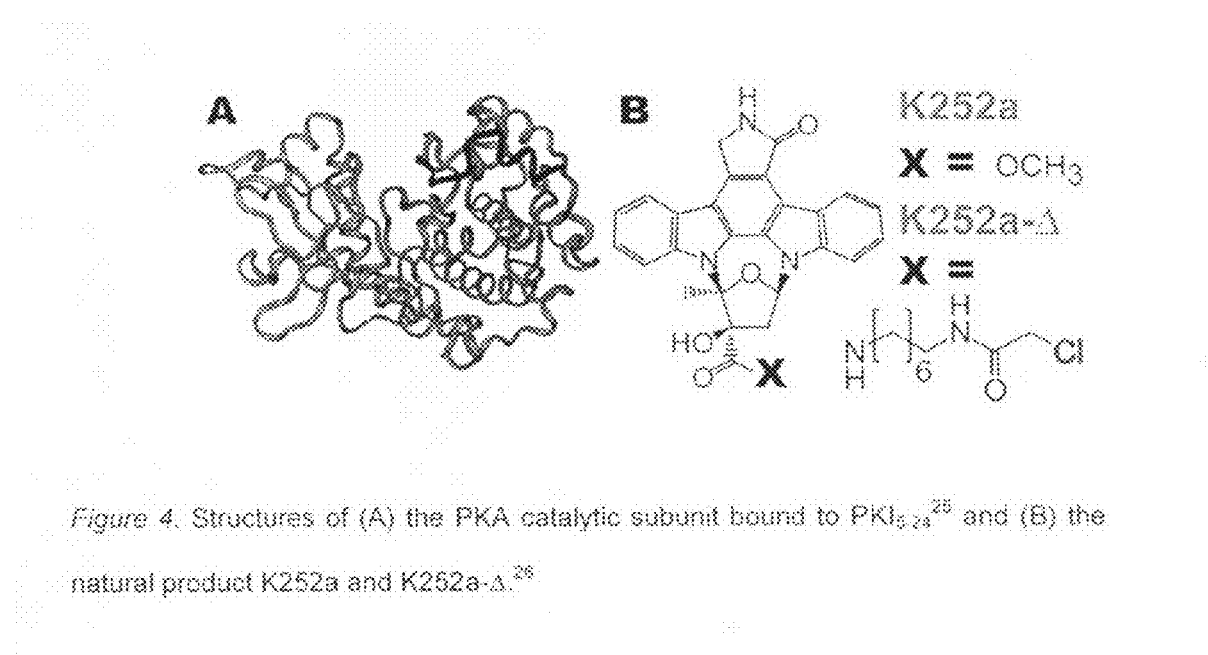
FIG. 4—Structures of (A) the PKA catalytic subunit bound to $PKI_{5-24}$ (Zheng, et al., *Acta Cryst* 1993, D49, 362-5) and (B) the natural product K252a and K252a-Δ.

Our design began with the structure of the catalytic subunit of cAMP-dependent protein kinase (PKA) in complex with $PKI_{5-24}$, a peptide representing the active portion of the heat-stable Protein Kinase Inhibitor protein (Glass et al., *J Biol Chem* 1989, 264, 8802-10; Zheng, et al., *Acta Cryst* 1993, D49, 362-5) (FIG. 4). In this complex, the $PKI_{5-24}$ C-terminal pseudosubstrate (residues 17-24) occupies the peptide substrate-binding site with energetically significant contacts from R18, R19, and I22 and R15 from the adjacent turn (residues 15-16); the N-terminal alpha helix (residues 5-13) nestles in a shallow hydrophobic groove outside the substrate-binding site with an energetically significant contact from F10. Two separate alignments of the sequences of the aPP and $PKI_{5-24}$ α-helices were considered (FIG. 5). Both alignments retain F10 of the $PKI_{5-24}$ α-helix, all three pseudosubstrate contacts, and all residues required to maintain the aPP fold; alignment #1 also retains R15. The resulting molecules, 1 and 2, were synthesized using standard solid phase methodology. A cysteine residue added to the C-terminus was modified with 5-iodo-acetamidofluorescein to facilitate fluorescence polarization analysis of PKA affinity.

Figure 6:
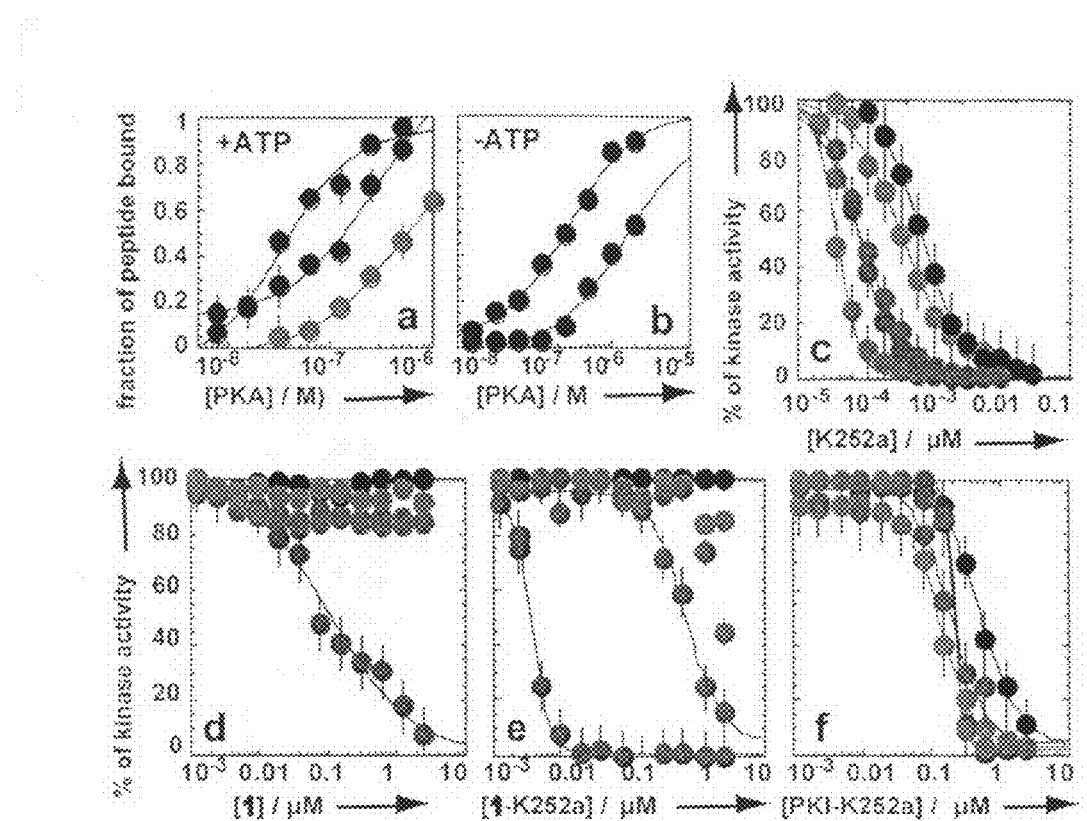

The relative affinities of $1^{Flu}$, $2^{Flu}$, and $PKI_{5-24}^{Flu}$ for the catalytic subunit of PKA were measured by fluorescence polarization analysis in the presence and absence of ATP (FIG. 6). In the presence of 100 µM ATP, the complex between PKA and $1^{Flu}$ was characterized by an equilibrium dissociation constant ($K_d$) of 99±39 nM (FIG. 6a). The stability of PKA•$1^{Flu}$ was only 3-fold lower than that of PKA•$PKI_{5-24}^{Flu}$ under identical conditions ($K_d$=31±8 nM). $2^{Flu}$ bound PKA with much lower affinity ($K_d$=570±123 nM), perhaps because it lacked R15, and was not considered further. Surprisingly, $1^{Flu}$ retained significant affinity for PKA in the absence of ATP ($K_d$=230±34 nM) (FIG. 6b). By contrast, $PKI_{5-24}^{Flu}$ bound PKA far more poorly in the absence of ATP, as expected (Whitehouse, et al., *J Biol Chem* 1983, 258, 3693-701), showing a 50-fold decrease in affinity ($K_d$=1.6±0.4 µM). Previous structural and biochemical studies have documented the dramatic change in PKA conformation induced by the binding of ATP (Johnson, et al., *Chem Rev* 2001, 101, 2243-70). Whereas the PKA apoenzyme exists in an open conformation that binds peptide substrate poorly, coordination of ATP rotates the large and small enzyme lobes, allowing substrate to bind the enzyme in a catalytically active, closed conformation (Akamine, et al., J Mol Biol 2003, 327, 159-71). Our results suggest that 1 recognizes the open and closed conformations of PKA with similar affinities or, alternatively, that the binding of 1 inhibits the conformational changes associated with ATP binding.

The miniature protein conjugate 1-K252a was designed after examination of the ternary complex of PKA with $PKI_{5-24}$ and the related indolocarbazole natural product staurosporine (Prade, et al., Structure 1997, 5, 1627-37). This analysis suggested that an octamethylene chain would appropriately link a C3' amide derivative of K252a to the side chain of residue 40 within 1. K252a analogs with conservative substitutions at C3' retain potency against a range of kinases, suggesting that an octamethylene chain at this position would be tolerated. Moreover, the $PKA-PKI_{5-24}$ structure shows the side chain of the corresponding residue of $PKI_{5-24}$, A21, pointing directly into the ATP/staurosporine binding pocket. Accordingly, we synthesized chloroacetamide K252aΔ (FIG. 4) and a derivative of 1 with a cysteine residue in place of alanine at position 40 (FIG. 5). $1^{440C}$ was alkylated with K252 aΔ in the presence of NaI, yielding 1-K252a. K252 aΔ was also used to alkylate $PKI^{421C}$ to produce PKI-K252a.

The inhibitory potencies of 1, 1-K252a, PKI-K252a, and K252a itself were measured using an assay based on streptavidin-matrix capture of biotinylated, [$^{32}$P]-phosphorylated substrates in which ATP and peptide substrate concentrations were fixed below their respective $K_M$ values. As expected, K252a was a potent PKA inhibitor ($IC_{50}$=0.140±0.003 nM) (FIG. 6c) and the potency of 1 was similar to its PKA affinity ($IC_{50}$=117±14 nM) (FIG. 6d). The miniature protein conjugate 1-K252a was 30-fold more potent ($IC_{50}$=3.65±0.13 nM) than 1 alone (FIG. 6e). Interestingly, the analogous molecule PKI-K252a was 60-fold less potent ($IC_{50}$=221±2 nM) than 1-K252a (FIG. 6f) and far less potent than PKI ($K_i$=2.3 nM) (Cheng, et al., J Biol Chem 1986, 261, 989-92). Both 1-K252a and PKI-K252a were far more potent than variants of $1^{440C}$ or $PKI^{421C}$ alkylated with bromoacetamide in place of K252 aΔ ($IC_{50}$>1 μM, data not shown). The differential potencies of 1-K252a and PKI-K252a may arise from differences in the affinity of 1 and $PKI_{5-24}$ for the unique conformation of PKA observed in ternary complex with $PKI_{5-24}$ and staurosporine.

To evaluate the extent to which 1 alters the kinase specificity of K252a, the phosphotransferase assay described above was reconfigured to assay the activities of four distinct but related protein kinases. Akt kinase (PKB), protein kinase Cα (PKC-α) Ca++/calmodulin kinase II (CamKII), and cGMP-dependent protein kinase (PKG) are all inhibited by K252a (FIG. 6c) but not by $PKI_{5-24}$. Both 1 and 1-K252a showed remarkable specificity for PKA, inhibiting no other kinase tested at concentrations as high as 100 nM (1-K252a) or 5 μM (1) (FIG. 6d-e). The only other kinase inhibited by 1-K252a was PKG ($IC_{50}$=679±202 nM), the kinase most similar to PKA (Glass, et al., J Biol Chem 1986, 261, 12166-71). By contrast, PKI-K252a displayed low specificity, inhibiting all kinases tested with $IC_{50}$ values within a 4-fold range (FIG. 6f). In summary, the $PKI_{5-24}$ conjugate PKI-K252a displayed lower potency than K252a and lower specificity than $PKI_{5-24}$ whereas the miniature protein conjugate 1-K252a displayed higher specificity than K252a and higher potency than 1. Our results suggest that molecules such as 1-K252a that embody elements of protein surface recognition could represent a viable general strategy for selective kinase inhibition.

Example 19

Miniature Proteins for Activating Transcription through Interactions with the Co-Activator Protein CREB-Binding Protein (CBP): High Affinity Ligands for the CBP KIX Domain The complex between the KIX domain of the transcriptional coactivator protein CBP and the kinase-inducible activation domain (KID) of the transcription factor CREB, though also mediated by an α-helix, is strikingly different from the complexes formed by Bcl-2 family members. The KID-binding groove of the CBP KIX domain is quite shallow and more closely resembles the solvent-exposed protein surface than a typical α-helix-binding groove (Radhakrishnan, et al., Cell 1997, 91, 741-752). In fact, only one hydrophobic residue of CREB KID is completely buried from solvent in the KID•KIX complex, and formation of a high affinity KID•KIX complex requires the enthalpic driving force provided by phosphorylation of CREB KID on Ser133 (Mestas, et al., Nat Struct Biol 1999, 6, 613-614; Zor, et al., J Biol Chem 2002, 277, 42241-42248). Thus, CBP KIX represents a difficult target for molecular recognition, and indeed, no small molecule ligands for CBP KIX have been reported. In this study, protein grafting and molecular evolution by phage display are used to identify phosphorylated peptide ligands that recognize the hydrophobic surface of CBP KIX with high nanomolar to low micromolar affinity and high specificity. Furthermore, grafting of the CBP KIX-binding epitope of CREB KID onto the aPP scaffold yields molecules capable of high affinity and specific recognition of CBP KIX even in the absence of phosphorylation.

A. Library Design and Generation.

The design of a CBP KIX-binding miniature protein (PP-KID) library was based on the alignment of the α-helix of aPP and helix B of the CREB KID domain shown in FIG. 7B. The otherwise unstructured phosphorylated CREB KID ($KID^P$) domain forms two α-helices, A and B, when bound to the CBP KIX domain; each helix contacts a different region of the CBP KIX surface (Radhakrishnan, et al., Cell 1997, 91, 741-752). Mutagenesis studies have determined that most (though not all) of the residues that comprise the CBP KIX-binding epitope of CREB $KID^P$ are located in helix B (Radhakrishnan, et al., Cell 1997, 91, 741-752; Parker, et al., Mol Cell 1998, 2, 353-359), and only residues from helix B were included in the miniature protein library. Four hydrophobic residues from CREB KID (Tyr134, Ile137, Leu138, Leu141) contribute significantly to the free energy of $KID^P$•KIX complex formation. The PPKID library contained three of these four residues (Ile137, Leu138, Leu141), and a conservative mutation of the fourth from Tyr to Phe, which in the context of CREB $KID^P$ has no effect on CBP KIX binding (Du, et al., Mol Cell Biol 2000, 20, 4320-4327). This mutation was included, along with the complete recognition site for protein kinase A (PKA; Arg130, Arg131, Ser133), to promote phosphorylation of the miniature protein library in vitro, if so desired. In the context of CREB $KID^P$, the Tyr to Phe mutation lowers five-fold the $K_m$ for phosphorylation by PKA (Du, et al., Mol Cell Biol 2000, 20, 4320-4327). The structural scaffold of the α-helical portion of the library was provided by six of eight residues (Val14, Leu17, Phe20, Leu24, Tyr27, Leu28) from the aPP α-helix that contribute to the hydrophobic core (Glover, et al., Biopolymers 1983, 22, 293-304). Based on our success using a similar approach to improve DNA-binding miniature proteins (Chin, et al., J Am Chem Soc 2001, 123, 2929-2930), the five residues from the polyproline helix of aPP known to participate in hydrophobic core formation (Pro2, Gln4, Pro5, Tyr7, Pro8) were varied to all 20 amino acids. Our expectation was that the CBP KIX-binding epitope on the α-helix would guide all library members to the CBP KIX surface, and the functional selection would identify those library members with increased CBP KIX affinity derived from packing of the polyproline helix against the otherwise exposed face of the bound α-helix. A $5 \times 10^7$-member library of miniature proteins (PPKID Library 1) (SEQ ID NO: 38) based on this design was generated for use in phage display selection experiments.

B. Selection of Phosphorylated Miniature Protein Ligands for CBP KIX.

Initially, eight rounds of selection were performed (selection 1). Each round included a PKA-catalyzed in vitro phosphorylation step designed to increase the CBP KIX-binding affinities of all library members. Phosphorylation of CREB KID is critical for high affinity recognition of CBP KIX; measurements of the contribution of the Ser133 phosphate moiety to the free energy of the $\text{KID}^P \cdot \text{KIX}$ complex range between 1.5 and 3.0 kcal·mol$^{-1}$ (Mestas, et al., Nat Struct Biol 1999, 6, 613-614; Zor, et al., J Biol Chem 2002, 277, 42241-42248). In this selection, GST-KIX was immobilized on glutathione-coated microtiter plates, and stringency was increased over the course of the selection by increasing the binding and washing temperature, from 4° C. in round 1 to 25° C. by round 3, and by increasing the length and number of washes, from 10×1 min washes in round 1 to 20×5 min washes in round 8. Rounds 7 and 8 were performed in binding buffer containing 5 mM dithiothreitol (DTT), after sequencing of individual clones from rounds 4-6 indicated that a significant portion of the library members selected in these rounds contained single Cys residues. The Cys residues were evenly distributed over all five randomized positions, which suggested that library members were being selected based on their ability to form disulfide bonds with GST-KIX or glutathione, rather than based on high affinity, yet noncovalent, CBP KIX binding.

The progress of the selection was monitored by measuring the retention of library phage in comparison to the retention of phage displaying aPP, which should not bind to GST-KIX, and by sequencing of individual clones after each round of selection. By round 8 of selection 1, the library phage were retained 13-fold over aPP phage. Furthermore, by round 7, three sequences (PPKID 1-3) had been identified in multiple independent clones (Table 1); two of these sequences (PPKID2, PPKID3) completely dominated the library by round 8. Surprisingly, the residues selected at each of the five randomized positions in PPKID2 and PPKID3 displayed no significant similarity (PPKID2 and PPKID3 each contain a spurious mutation not encoded in the original library pool, but the mutation is different in each peptide (Tyr to Asp at position 21 for PPKID2, Leu to Arg at position 24 for PPKID3)).

TABLE 1

HisKIX-binding affinity of PPKID and control peptides[a]

| Selection 1 | | $K_d$ PPKID$^P$ (nM) | $K_d$ PPKID$^U$ (μM) |
|---|---|---|---|
| PPKID1 | GASDMTYWGDDAPVRRLSFFYILLDLYLDAPGVC (SEQ ID NO:80) | 591 ± 59 | 24.1 ± 4.0 |
| PPKID2 | GMSRVTPGGDDAPVRRLSFFYILRDLYLDAPGVC (SEQ ID NO:81) | 729 ± 36 | 12.6 ± 1.4 |
| PPKID3 | GASPHTSSGDDAPVRRLSFFDILLDLYLDAPGVC (SEQ ID NO:82) | 1200 ± 100 | 6.7 ± 0.2 |
| Selections 2 & 4 | | $K_d$ PPKID$^P$ (nM) | $K_d$ PPKID$^U$ (μM) |
| PPKID4 | GPSQPTYPGDDAPVRRLSFFYILLDLYLDAPGVC (SEQ ID NO:83) | 515 ± 44 | 12.1 ± 2.4 |
| PPKID5 | GLSWPTYHGDDAPVRRLSFFYILLDLYLDAPGVC (SEQ ID NO:84) | 534 ± 31 | 6.6 ± 2.0 |
| Selections 3 & 4 | | $K_d$ PPKID$^P$ (nM) | $K_d$ PPKID$^U$ (μM) |
| PPKID6 | GISWPTFEGDDAPVRRLSFFYILLDLYLDAPGVC (SEQ ID NO:85) | 624 ± 49 | 1.5 ± 0.1 |
| PPKID6 S18E | GISWPTFEGDDAPVRRLEFFYILLDLYLDAPGVC (SEQ ID NO:86) | | 10.9 ± 2.0 |
| PPKID7 | GLSPYTEWGDDAPVRRLSFFYILLDLYLDAPGVC (SEQ ID NO:87) | | 2.3 ± 0.2 |
| PPKID8 | GLSWKTDPGDDAPVRRLSFFYILLDLYLDAPGVC (SEQ ID NO:88) | | 3.1 ± 0.5 |
| Control peptides | | P:$K_d$ | U:$K_d$ (μM) |
| KID-AB | TDSQKRREILSRRPSYRKILNDLSSDAPGVC (SEQ ID NO:89) | 562 ± 41 nM | >116 |

TABLE 1-continued

HisKIX-binding affinity of PPKID and control peptides[a]

| KID-B | RRPSYRKILNDLSSDAPGVC | 51.6 ± 4.0 μM | >297 |
| (SEQ ID NO:90) | | | |
| Peptide C | RRLSFFYILLDLYLDAPGVC | 2.4 ± 0.2 μM | 21.5 ± 2.6 |
| (SEQ ID NO:91) | | | |

[a]Each peptide was labeled on the C-terminal Cys residue with acetamidofluorescein for use in fluorescence polarization experiments. $K_d$ values were determined by converting polarization data from three independent samples to fraction of fluorescently-labeled peptide bound values, which were fit to equilibrium binding equation (2). Residues selected at randomized positions are in red. Selected point mutations in PPKID2 and PPKID3 are underlined. P indicates a phosphopeptide. U indicates an unphosphorylated peptide. The phosphoserine residue in phosphopeptides is in bold.

C. CBP KIX-Binding Affinity.

The PPKID peptides were synthesized as phosphopeptides (PPKID$^P$) and each was labeled with acetamidofluorescein on a C-terminal Cys residue. The affinity of each labeled peptide for a His-tagged CBP KIX domain (HisKIX) was measured by equilibrium fluorescence polarization. The HisKIX-binding affinities of three phosphorylated control peptides (KID-AB$^P$, KID-B$^P$ and peptide C$^P$) were also measured. Peptide KID-AB$^P$ comprises the full-length CREB KID domain (residues 119-148, A and B helices) and peptide KID-B$^P$ corresponds to the region of CBP KID whose residues were incorporated within the α-helix of aPP (residues 130-148, the PKA recognition site and helix B); these peptides allow direct comparison of our miniature proteins with natural CBP KIX-binding molecules. Peptide C$^P$ corresponds to the chimeric α-helical portion of the PPKID peptides (residues 15-33) and allows us to compare the contribution to CBP KIX-binding affinity of residues in the α-helix derived from aPP and residues in the randomized region of the PPKID library, which includes the putative polyproline helix and turn regions.

Figure 8:
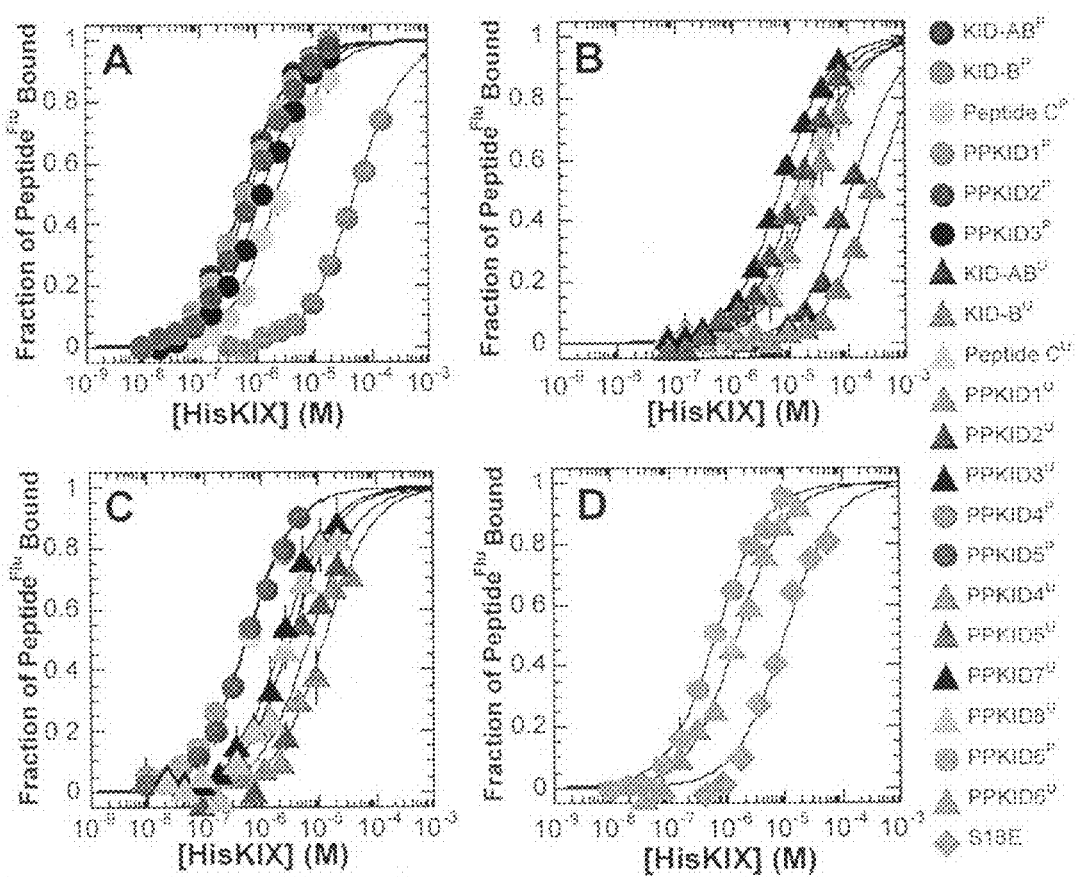
FIG. 8—HisKIX-binding affinity of PPKID and control peptides measured by fluorescence polarization. Serial dilutions of HisKIX were incubated with 25-50 nM of fluorescein-labeled peptide (peptide$^{Flu}$) for 30 min at 25° C. Each point represents an average of three independent samples; the error bars denote standard error. Observed polarization values were converted to fraction of peptide$^{Flu}$ bound using $P_{min}$ and $P_{max}$ values derived from the best fit of the polarization data to equation (1). Curves shown are the best fit of fraction of peptide$^{Flu}$ bound values to the equilibrium binding equation (2). Fraction of phosphorylated peptide$^{Flu}$ bound values are indicated with circular symbols, and fraction of unphosphorylated peptide$^{Flu}$ bound values are indicated with triangular symbols. (A) KID-AB$^P$, KID-B$^P$, peptide $C^P$ and PPKID$^P$ 1-3. (B) KID-AB$^U$, KID-B$^U$, peptide $C^U$ and PPKID$^U$ 1-3. (C) PPKID$^P$ 4-5, PPKID$^U$ 4-5 and PPKID$^U$ 7-8. (D) PPKID6$^U$, PPKID6$^P$ and PPKID6 S18E.

The results of the equilibrium fluorescence polarization experiments are shown in FIG. 8A and Table 1. KID-AB$^P$ binds HisKIX with high affinity ($K_d$=562±41 nM) at 25° C. under the assay conditions used. This value is lower than previously reported $K_d$s for similar KID$^P$•KIX complexes (3.1 μM to 9.7 μM) measured by a number of techniques (though not fluorescence polarization) and may result from slight differences in the buffers and the CREB KID$^P$ and CBP KIX constructs used in each case. Peptides PPKID$^P$ 1-3 bind HisKIX with affinities ranging from 591 nM to 1.2 μM, values that are comparable to the HisKIX-binding affinity of KID-AB$^P$.

Remarkably, peptides PPKID$^P$ 1-3 bind HisKIX with 43- to 87-fold higher affinity than does KID-B$^P$ ($K_d$=51.6±4.0 μM; this value is comparable to the $K_d$ of 80 μM reported for the KID(129-149)$^P$•KIX complex measured by isothermal titration calorimetry). Most of this increase in affinity can be attributed to the aPP-derived residues in the α-helical region of the miniature proteins; peptide C$^P$ (which comprises the α-helical region of PPKID$^P$ 1-3) binds HisKIX with a $K_d$ of 2.4±0.2 μM, which represents a greater than 20-fold increase in affinity (ΔΔG=−1.8 kcal·mol$^{-1}$) compared to the CBP KIX-binding affinity of KID-B$^P$. The turn and polyproline helix regions (including selected residues) of the PPKID$^P$ 1-3 peptides contribute a more modest −0.4 to −0.8 kcal·mol$^{-1}$ to the free energy of complex formation with CBP KIX.

The HisKIX-binding affinities of unphosphorylated versions (denoted by a superscript U) of PPKID 1-3, KID-AB, KID-B and peptide C were also determined (FIG. 8B and Table 1). As expected, the KID-AB$^U$ and KID-B$^U$ peptides possess very low affinities for HisKIX. Only a small change in polarization of the KID-AB$^U$-Flu (61 mP) or KID-B$^U$-Flu (76 mP) molecules was observed even at the highest HisKIX concentrations tested (150 μM and 325 μM, respectively). This experiment allows us to place a lower limit on the $K_d$ of the complex formed between each of these peptides and HisKIX. If we estimate the change in polarization of KID-AB$^U$-Flu to be 110 mP and the change in polarization of KID-B$^U$-Flu to be 150 mP when fully bound by HisKIX (based on observed changes in polarization of 116 mP for fully HisKIX-bound KID-AB$^P$ and 161 mP for KID-B$^P$), we can estimate that the $K_d$ of the KID-AB$^U$•HisKIX complex must be greater than 116 μM and the $K_d$ of the KID-B$^U$-HisKIX complex must be greater than 297 μM. Remarkably, the seven amino acid changes (including the conservative Tyr to Phe mutation) that convert KID-B$^U$ to peptide C$^U$ dramatically enhance CBP KIX-binding affinity (ΔΔG≧−1.5 kcal·mol$^{-1}$). Peptide C$^U$ binds HisKIX with a $K_d$ of 21.5±2.6 μM. Addition of the turn and selected polyproline helix regions to yield peptides PPKID$^U$ 1-3 slightly increases or even slightly decreases CBP KIX-binding affinity 1- to 3-fold ($K_d$=6.7 to 24.1 μM; ΔΔG=−0.7 to +0.1 kcal·mol$^{-1}$). As is true in the context of phosphorylated peptides, then, most of the free energy of complex formation with HisKIX is due to aPP-derived residues in the putative α-helical region of the PPKID$^U$ peptides.

D. Minimizing Fusion Protein Binding.

Preliminary fluorescence polarization experiments using GST-KIX as a target indicated that two of the selected peptides (PPKID1 and PPKID3) possessed significantly higher (16- to 19-fold) affinity for GST-KIX than for HisKIX (data not shown). Therefore, we subjected the members of PPKID Library 1 to a second selection (selection 2) in which GST-KIX and HisKIX were alternated as the immobilized target protein to minimize selection of library members based on increased affinity for the GST-KIX or HisKIX fusion proteins relative to the isolated CBP KIX domain. Binding and washing conditions were similar to those used in selection 1, and each round included a PKA-catalyzed phosphorylation step. DTT (5 mM) was included in the binding buffer in all rounds where GST-KIX was used as a target (except for round 1) to minimize selection based on disulfide bond formation. After nine rounds of selection, the library phage were retained 44-fold over phage displaying aPP, although no consensus in miniature protein sequence was achieved. However, two sequences were identified in multiple independent clones from rounds 7-9 (PPKID 4-5). Interestingly, PPKID4 contains aPP-derived residues in all randomized positions.

PPKID4 and PPKID5 contain identical residues at two of the randomized positions, 5 (Pro) and 7 (Tyr), but otherwise the selected residues are not conserved. Furthermore, none of the selected residues in either PPKID4 or PPKID5 are similar to the selected residues in PPKID 1-3. PPKID4 and PPKID5 exhibit high affinity for HisKIX (FIG. 8C and Table 1), with $K_d$s in both phosphorylated (515±44 nM and 534±31 nM, respectively) and unphosphorylated forms (12.1±2.4 μM and 6.6±2.0 μM, respectively) similar to those observed for PPKID 1-3.

E. Unphosphorylated Selections.

The significant CBP KIX-binding affinity displayed by peptide $C^U$ (as well as by short, unphosphorylated CBP KIX-binding peptides identified by Montminy and coworkers) encouraged us to perform selections with unphosphorylated PPKID Library 1. Unphosphorylated selections (selections 3 & 4) were performed in parallel with selections 1 & 2, with similar binding and washing conditions. After nine rounds of selection, the library phage in selection 3 were retained 32-fold over phage displaying aPP, and the library phage in selection 4 were retained 11-fold over phage displaying aPP. Although no consensus was reached in either selection, a number of sequences were identified in multiple independent clones. In selection 3, one sequence, PPKID6, was identified in rounds 6-9. Two of the sequences identified in selection 4, PPKID4 and PPKID5, were also identified in selection 2 (which included the phosphorylation step in each round) under the same conditions. Two additional sequences, PPKID7 and PPKID8, were identified in rounds 6-9 in selection 4.

Interestingly, four of five randomized positions (2, 4, 5, and 7) in peptides PPKID 4-9 approach consensus; Leu or Ile was selected at position 2, Trp at position 4, Pro at position 5, and aromatic or negatively charged residues at position 7. $PPKID6^U$, $PPKID7^U$ and $PPKID8^U$ exhibit exceptionally high affinity for HisKIX, as measured by fluorescence polarization, with $K_d$s ranging from 1.5 μM to 3.1 μM (FIG. 8C-D and Table 1). These values correspond to at least 37- to 77-fold enhancements in HisKIX-binding affinity compared to $KID-AB^U$ and at least 96- to 198-fold enhancements relative to $KID-B^U$. Furthermore, peptides $PPKID^U$ 6-8 bind HisKIX with 7- to 14-fold enhancements in binding affinity compared to peptide $C^U$. Thus, the selected polyproline helix and turn regions of the $PPKID^U$ 6-8 peptides contribute −1.2 to −1.6 kcal·mol$^{-1}$ to the free energy of complex formation with CBP KIX.

We investigated the HisKIX-binding affinities of two variants of PPKID6, each containing a simple modification of residue Ser18, phosphorylation and substitution of Ser by Glu. Phosphorylation of PPKID6 leads to only a two-fold enhancement in HisKIX-binding affinity (ΔΔG=−0.5 kcal·mol$^{-1}$) (FIG. 8D), a significantly smaller enhancement than is observed upon phosphorylation for the other PPKID peptides (6- to 41-fold; ΔΔG=−1.0 to −2.2 kcal·mol$^{-1}$) and KID-AB (ΔΔG>3.2 kcal·mol$^{-1}$). Surprisingly, the Ser to Glu mutation actually decreases HisKIX-binding affinity 7-fold ($K_d$=10.9±2.0 μM; ΔΔG=+1.2 kcal·mol$^{-1}$). A similar mutation in the context of the full length CREB KID domain leads to CBP KIX-binding affinity intermediate between that of unphosphorylated and phosphorylated CREB KID (Shaywitz, et al., Mol Cell Biol 2000, 20, 9409-9422) presumably because the negative charge of Glu mimics the negatively charged phosphate moiety.

F. Binding Modes of $PPKID4^P$ and $PPKID6^U$.

Figure 9:
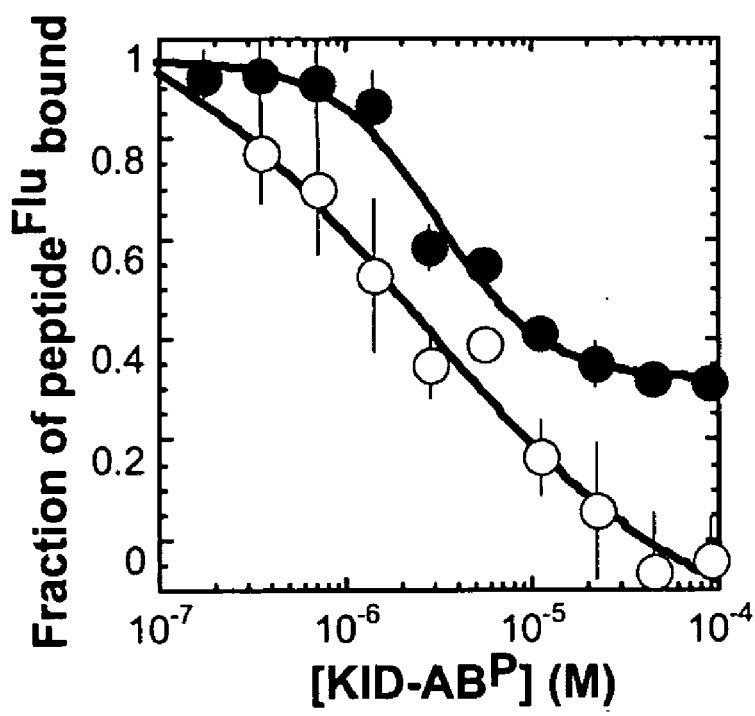
FIG. 9—Competition between KID-AB$^P$ and PPKID4$^P$ (solid circle) or PPKID6$^U$ (open circle) for binding to HisKIX measured by fluorescence polarization. Serial dilutions of KID-AB$^P$ were incubated with 1.5 μM or 3.0 μM HisKIX and 25 nM fluorescein-labeled PPKID4$^P$ or PPKID6$^U$ (peptide-$^{Flu}$) for 60 min at 25° C., respectively. Each point represents an average of three independent samples; the error bars denote standard error. Observed polarization values were converted to fraction of peptide$^{Flu}$ bound using experimentally determined $P_{min}$ and $P_{max}$ values corresponding to the polarization of samples containing 25 nM peptide$^{Flu}$ alone and peptide$^{Flu}$ with 1.5 μM or 3.0 μM HisKIX, respectively. Curves shown represent the best fit of fraction of peptide$^{Flu}$ bound values to equation (3). The close agreement between the $K_d$ of the KID-AB$^P$•HisKIX complex and the $IC_{50}$ values determined here provides evidence that the fluorescein tag appended to KID-AB$^P$ contributes neither positively nor negatively to the stability of the KID-AB$^P$•HisKIX complex.

Two sets of experiments were performed to investigate the binding modes of $PPKID4^P$ and $PPKID6^U$. First, competition fluorescence polarization experiments assessed the ability of $PPKID4^P$ and $PPKID6^U$ to compete with CREB $KID^P$ for binding CBP KIX. In particular, the fraction of fluorescently tagged $PPKID4^P$ or $PPKID6^U$ bound to HisKIX at equilibrium was monitored as a function of the concentration of unlabeled $KID-AB^P$. These experiments reveal that $KID-AB^P$ competes with both $PPKID4^P$ and $PPKID6^U$ for binding to CBP KIX (FIG. 9). The concentration of $KID-AB^P$ needed to displace 50% of fluorescently tagged $PPKID4^P$ or $PPKID6^U$ from HisKIX (the IC$_{50}$ value) is 3.2 μM or 2.4 μM, respectively. These values are, as expected given the conditions of the assay (Munson, et al., J Recept Res 1988, 8, 533-546), slightly larger than the $K_d$ of the $KID-AB^P$•HisKIX complex determined by direct fluorescence polarization analysis (562±41 nM). These results indicate that HisKIX cannot interact simultaneously with $KID-AB^P$ and either $PPKID4^P$ or $PPKID6^U$, and are consistent with an interaction of both $PPKID4^P$ and $PPKID6^U$ within the CREB $KID^P$-binding cleft of CBP KIX.

Figure 10:
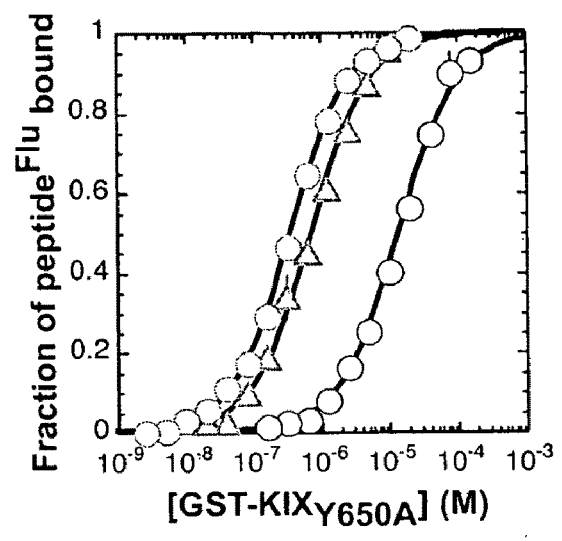
FIG. 10—Affinity of PPKID4$^P$ (blue circle), PPKID6$^U$ (blue triangle) and KID-AB$^P$ (red circle) for GST-KIX$_{Y650A}$ measured by fluorescence polarization. Serial dilutions of GST-KIX$_{Y650A}$ were incubated with 25 nM of fluorescein-labeled peptide (peptide$^{Flu}$) for 30 min at 25° C. Each point represents an average of three independent samples; the error bars denote standard error. Observed polarization values were converted to fraction of peptide$^{Flu}$ bound using $P_{min}$ and $P_{max}$ values derived from the best fit of the polarization data to equation (1). Curves shown are the best fit of fraction of peptide$^{Flu}$ bound values to the equilibrium binding equation (2).

Although $KID-AB^P$ competes with both $PPKID4^P$ and $PPKID6^U$ for binding to HisKIX, small changes in $KID-AB^P$ concentration around the corresponding IC$_{50}$ values have a larger effect on the change in the fraction of $PPKID4^P$ bound than on the change in the fraction of $PPKID6^U$ bound. This result suggests that there may exist differences in the orientation or geometry of $PPKID4^P$ and $PPKID6^U$ when bound to CBP KIX. To explore these differences in greater detail, we measured the affinities of $KID-AB^P$, $PPKID4^P$ and $PPKID6^U$ for the Y650A variant of CBP KIX (GST-KIX$_{Y650A}$) using direct fluorescence polarization analysis (FIG. 10). Tyr650 forms one side of the hydrophobic cleft within the CREB $KID^P$-binding groove of CBP KIX that accommodates Leu141 of helix B. As a result, CREB $KID^P$ exhibits significantly lower affinity for the Y650A variant relative to wild type CBP KIX. These two factors make GST-KIX$_{Y650A}$ an excellent surveyor of the CREB $KID^P$•CBP KIX interface.

The GST-KIX$_{Y650A}$•$KID-AB^P$ complex is 15-fold less stable than the wild type GST-KIX•$KID-AB^P$ complex as measured by fluorescence polarization, a difference in stability similar to that observed previously in ITC experiments performed with the same GST-KIX constructs. Likewise, the $PPKID4^P$•GST-KIX$_{Y650A}$ complex is 24-fold less stable than the wild type GST-KIX•$PPKID4^P$ complex. The observation that mutation of Tyr650 to Ala has a similar effect on the binding of $KID-AB^P$ and $PPKID4^P$, together with the equilibrium competition analysis, provides evidence that the two ligands interact with CBP KIX in a similar manner. Interestingly, despite the fact that $PPKID6^U$ and CREB $KID-AB^P$ compete for binding to CBP KIX, $PPKID6^U$ binds GST-KIX$_{Y650A}$ with the same affinity ($K_d$=712±68 nM) as it binds wild type GST-KIX ($K_d$=714±128 nM). This observation suggests that $PPKID6^U$ interacts with CBP KIX in a manner that is somewhat different from the CBP KIX-binding mode of $KID-AB^P$. Further work with an established panel of CBP KIX variants (Parker, et al., Mol Cell Biol 1999, 19, 5601-5607) currently in progress, will be necessary to characterize the binding mode of $PPKID6^U$ in detail.

G. PPKID Specificity.

Given the myriad protein surfaces present in the cell, the utility of molecules that recognize protein surfaces will depend on their ability to interact selectively with the desired protein. We investigated the specificity of our highest affinity phosphorylated ($PPKID4^P$) and unphosphorylated (PPKID6$^U$) CBP KIX ligands by measuring their affinity for two globular proteins, carbonic anhydrase II and calmodulin, known to recognize hydrophobic or helical molecules. To determine the effect of the region comprising the selected polyproline helix and turn on the specificity of PPKID4$^P$ and PPKID6$^U$, we also examined the specificity of peptide C, in both its phosphorylated and unphosphorylated forms.

Figure 11:
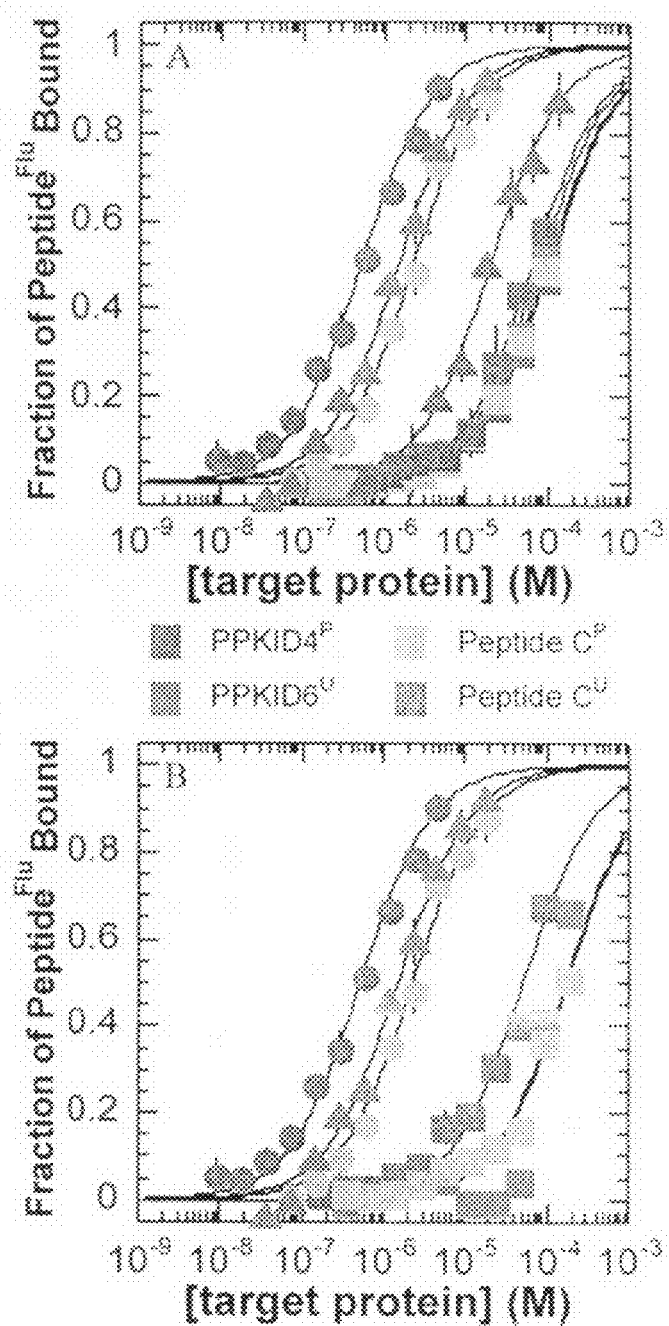
FIG. 11—Specificity of protein surface recognition by PPKID and control peptides measured by fluorescence polarization. Binding reactions containing serially diluted target protein and 25-50 nM of fluorescein-labeled peptides (peptide$^{Flu}$) were incubated for 30 min at 25° C. Each point represents the average polarization of two to three independent samples; error bars denote standard error. Observed polarization values were converted to fraction of peptide$^{Flu}$ bound using $P_{min}$ and $P_{max}$ values derived from the best fit of the polarization data to equation (1). Curves shown are the best fit of fraction of peptide$^{Flu}$ bound values to the equilibrium binding equation (2). (A) Plot illustrating the polarization of fluorescently-labeled PPKID4$^P$, PPKID6$^U$, peptide $C^P$ and peptide $C^U$ molecules as a function of target protein (carbonic anhydrase II or HisKIX) concentration. Circular and triangular symbols indicate that HisKIX was used as the target protein; the symbols are colored as in FIG. 9 with the exception of the points for peptide $C^U$, which are in orange for clarity. Square symbols indicate that carbonic anhydrase was used as the target protein. (B) Plot illustrating the polarization of fluorescently-labeled PPKID4$^P$, PPKID6$^U$ and peptide $C^P$ molecules as a function of target protein (calmodulin or HisKIX) concentration. Circular and triangular symbols indicate that HisKIX was used as the target protein, and the symbols are colored as in FIG. 9. Square symbols indicate that calmodulin was used as the target protein.

The PPKID peptides bind carbonic anhydrase with low affinity, with K$_d$s of 106±12 μM and 79±13 μM for PPKID4$^P$ and PPKID6$^U$, respectively (FIG. 11A and Table 2). These values define specificity ratios (K$_{rel}$=K$_d$ (carbonic anhydrase)/K$_d$ (HisKIX)) of 205 for PPKID4$^P$ and 53 for PPKID6$^U$. The preference of PPKID4$^P$ for HisKIX over carbonic anhydrase (K$_{rel}$=205) is considerably higher than the preference of control peptide C$^P$ for HisKIX over carbonic anhydrase (K$_{rel}$=40), despite their approximately equal affinity for carbonic anhydrase (106 μM and 97 μM, respectively). Thus, the increased specificity of PPKID4$^P$ relative to peptide C$^P$ is due to enhanced affinity for HisKIX, and not a result of decreased affinity for carbonic anhydrase. Similar conclusions are drawn when comparing PPKID6$^U$ and peptide C$^U$; although these two molecules display similar affinities for carbonic anhydrase, with K$_d$ values of 79 μM and 66 μM, respectively, the specificity ratio for PPKID6$^U$ (K$_{rel}$=53) is significantly higher than the specificity ratio for peptide C$^U$ (K$_{rel}$=3).

PPKID4$^P$, exhibits a significant preference for CBP KIX over calmodulin, with a specificity ratio of at least 112.

In sum, the work described here extends the utility of the protein grafting and molecular evolution procedure to the significant problem of high affinity and specific recognition of shallow protein surfaces. Taken together with previous applications, the protein grafting strategy has now proven to be extremely general in scope, enabling the discovery of highly functional miniature proteins capable of molecular recognition of diverse nucleic acid and protein targets. In addition, a posttranslational modification step, phosphorylation, was introduced here for the first time into the molecular evolution protocol used in protein grafting. Phosphorylated peptide ligands based on the functional epitope of the CREB KID domain were discovered which possess high nanomolar to low micromolar affinity and high specificity for the shallow surface groove of the CBP KIX domain. Furthermore, presentation of the CREB KID domain functional epitope on the aPP scaffold protein yielded peptide ligands for CBP KIX which bypass the need for phosphorylation to achieve high affinity CBP KIX recognition and have potential for use as extremely potent transcriptional activation domains.

H. Experimental Section.

1) HisKIX expression vector cloning—The CBP KIX-coding region (residues 586 to 672) of pGEX-KT KIX 10-672 (a

TABLE 2

Specificity of PPKID and control peptides[a]

| Peptides | | K$_d$ HisKIX (μM) | K$_d$ CA (μM) (K$_{rel}$) | K$_d$ CalM (μM) (K$_{rel}$) |
|---|---|---|---|---|
| PPKID4$^P$ | GPSQPTYPGDDAPVRRLSFFYILLDLYLDAPGVC (SEQ ID NO:83) | 0.515 ± 0.044 | 106 ± 12 (205) | 52 ± 12 (100) |
| PPKID6$^U$ | GISWPTFEGDDAPVRRLSFFYILLDLYLDAPGVC (SEQ ID NO:85) | 1.5 ± 0.1 | 79 ± 13 (53) | >168 (>112) |
| C$^P$ | RRLSFFYILLDLYLDAPGVC (SEQ ID NO:91) | 2.4 ± 0.2 | 97 ± 6 (40) | 178 ± 42 (74) |
| C$^U$ | RRLSFFYILLDLYLDAPGVC (SEQ ID NO:91) | 21.5 ± 2.6 | 66 ± 11 (3) | N.D. |

[a]Each peptide was labeled on the C-terminal Cys residue with acetamidofluorescein for use in fluorescence polarization experiments. K$_d$ values were determined by converting polarization data from two to three independent samples to fraction of fluorescently-labeled peptide bound values, which were fit to equilibrium binding equation (2). Residues selected at randomized positions are in red. P indicates a phosphopeptide. U indicates an unphosphorylated peptide. The phosphoserine residue in phosphopeptides is in bold. CA indicates that carbonic anhydrase II was used as the target protein; CalM indicates calmodulin was used as the target protein. The specificity ratio K$_{rel}$ is defined as K$_{rel}$ = K$_d$ (CA or CalM)/K$_d$ (HisKIX). N.D. indicates that the value was not determined.

The selected PPKID molecules also display a dramatic preference for binding CBP KIX over calmodulin (FIG. 11B and Table 2). PPKID4$^P$ binds calmodulin with a K$_d$ of 51±12 μM, which corresponds to a K$_{rel}$ value of 100. Peptide C$^P$ displays slightly lower specificity (K$_{rel}$=74) than PPKID4$^P$ for CBP KIX over calmodulin, a result of 5-fold lower affinity for HisKIX and 4-fold lower affinity for calmodulin (K$_d$=178±42 μM). The K$_d$ for the PPKID6$^U$•calmodulin complex could not be determined definitively, but we could place a lower limit of 168 μM on the K$_d$ value by defining the minimum change in polarization between the fully calmodulin-bound and fully unbound states of fluorescently labeled PPKID6$^U$ as 100 mP (the observed change in the presence of 185 μM calmodulin was 66 mP). Thus, PPKID6$^u$, like gift from Marc Montminy) (Parker, et al., Mol Cell Biol 1999, 19, 5601-5607) was amplified by PCR using 5' and 3' primers containing NdeI and BamHI restriction sites, respectively. Primers KIX5P and KIX3P had the following sequences: KIX5P: 5'-GCCGCGCGGCA GCCATATGGG TGTTC GAAAAGCCTGGC-3' (SEQ ID NO: 92); KIX3P: 5'-CCAGGCCGCTGCG GATCCTCATCATAA ACGT-GACCTCCGC-3' (SEQ ID NO: 93). The CBP KIX-coding duplex DNA insert was digested with NdeI and BamHI and ligated into NdeI- and BamHI-digested pET15b (Novagen) using T4 DNA ligase (New England Biolabs). The resulting plasmid, pHisKIX, codes for the CBP KIX domain in-frame with an amino-terminal hexahistidine tag under control of a T7 promoter. Plasmid identity was confirmed by DNA sequencing of the CBP KIX-coding region of pHisKIX.

2) Overexpression and purification of GST-KIX and HisKIX-pGST-ΔKIX(588-683) (a gift from Jennifer Nyborg) (Yan, et al., J Mol Biol 1998, 281, 395-400) or pHisKIX was transformed into BL21(DE3) pArg E. coli cells by electroporation. A single colony was used to inoculate a 1 L culture of LB media containing 0.2 mg/mL ampicillin and 0.05 mg/mL kanamycin. The culture was incubated at 37° C. with shaking at 250 rpm until the solution reached an optical density of 0.6 absorbance units at 600 nm. Isopropyl β-D-thiogalactoside (IPTG) was added to a final concentration of 1 mM and incubation continued for 3 h at 37° C. Cells were harvested by centrifugation for 20 min at 10,800 g and resuspended in 15-20 mL of buffer (GST-KIX: 50 mM potassium phosphate (pH 7.2), 150 mM NaCl, 1 mM DTT; HisKIX: 50 mM sodium phosphate (pH 8.0), 300 mM NaCl, 10 mM imidazole). Cells were lysed by sonication, insoluble material was pelleted by centrifugation for 30 min at 37,000 g, and the supernatant was retained. GST-KIX and HisKIX proteins were purified by glutathione and nickel-nitrolotriacetic acid (Ni-NTA) affinity chromatography, respectively. Fractions containing the desired protein were combined, desalted on a NAP 10 (GST-KIX) or NAP 25 (HisKIX) column (Amersham) and stored in buffer containing 50 mM Tris (pH 8.0), 100 mM KCl, 12.5 mM $MgCl_2$, 1 mM ethylenediaminetetraacetic acid (EDTA) and 0.05% Tween-20 (GST-KIX storage buffer also contained 1 mM DTT) at −70° C. Protein identity and concentration were confirmed by amino acid analysis.

3) Phage library construction—PPKID Library 1 was created by cassette mutagenesis of the phagemid vector pJC20 (Chin, et al., Bioorg Med Chem Lett 2001, 11, 1501-1505) using the synthetic oligonucleotides Align1 and PPLib. These oligonucleotides possessed the following sequences (N indicates an equimolar mixture of G, C, A and T, and S indicates an equimolar mixture of G and C): Align1: 5'-TGTTCCTT TCTATGCACCGGTTCGTCTC TGTCC TT CTTCTA-CATCCTGCTGGACCTGTACC TGGACGCACCG-GCGGC CGCAGGTGCGCCGGGCC-3' (SEQ ID NO: 94); PPLib: 5'-TGTTCCTTTCTAT GCGGCCCAGCCG GCCGTNNS TCCNNSNNSACCNNSNNSGG TGAC-GACGCACCG GTAGGTGCGCC GGTGCC-3' (SEQ ID NO: 95). Double stranded Align1 and PPLib inserts were generated by primer extension of appropriate primers using Sequenase version 2.0 T7 DNA polymerase (US Biochemicals). The duplex Align1 insert was digested with AgeI and NotI, and purified from a preparative agarose gel using the QIAquick gel extraction kit (Qiagen) and ethanol precipitation. Purified Align1 insert was ligated into AgeI- and NotI-digested pJC20 using the Ligation Express Kit (Clontech) to yield the phagemid vector pAlign1. Double stranded PPLib insert was digested with AgeI and SfiI and purified as per Align1. PPLib insert was ligated into AgeI- and SfiI-digested pAlign1 using the Ligation Express Kit (Clontech) to generate PPKID Library 1. The ligated PPKID Library 1 phagemid vector was transformed into XL1 Blue E. coli cells by electroporation and amplified by overnight growth at 37° C. in 2×YT-AG media (2×YT media containing 2% (w/v) glucose and 0.1 mg/mL ampicillin). Glycerol stocks of this culture were used as the initial pool for selection experiments. PPKID Library 1 contained $5 \times 10^7$ independent transformants, which covered the theoretical diversity of the library ($32^5 = 3.36 \times 10^7$) with 77% confidence. Sequencing of twenty individual clones from the initial pool verified the quality of the library; none of the sequenced clones contained mutations, deletions or insertions in the PPKID-coding region.

4) Phage display procedure—A glycerol stock of the initial pool (round 1) or output from the previous round (rounds 2-9) was used to inoculate 10 mL 2×YT-AG media. The culture was incubated at 37° C. until it reached an optical density of 0.6 absorbance units at 600 nm. The culture was then infected with $4 \times 10^{11}$ pfu M13K07 helper phage and incubated at 37° C. for 1 h. Cells were pelleted by centrifugation, resuspended in 10 mL 2×YT-AK (2×YT media containing 0.1 mg/mL ampicillin and 0.05 mg/mL kanamycin) and incubated for 12-13 h at 37° C. Cells were then pelleted by centrifugation and the retained supernatant was filtered through a 0.45 μm syringe filter. Phage were precipitated with 1/5 volume PEG/NaCl (20% (w/v) PEG-8000, 2.5 M NaCl) on ice for 45 min, and then pelleted by centrifugation for 35 min at 24,000 g. For phosphorylated selections, the precipitated phage were resuspended in water and approximately $10^{10}$ phage were phosphorylated in vitro with 2500 U PKA (Promega) in 100 μM ATP, 40 mM Tris (pH 8), 20 mM magnesium acetate for 2 h at 30° C. Phosphorylated phage were precipitated on ice for 45 min with PEG/NaCl and then pelleted by centrifugation at maximum speed in a microcentrifuge for 30 min. Mock phosphorylation reactions were performed in parallel without PKA, and purified in the same manner. Precipitated phage (+/−PKA treatment) were resuspended in binding buffer for use in selections. HisKIX binding buffer contained 50 mM potassium phosphate (pH 7.2), 150 mM NaCl, 0.05% Tween-20 and GST-KIX binding buffer contained 20 mM Tris (pH 8.0), 150 mM NaCl, 0.1% Tween-20.

Selections against HisKIX were performed in Ni-NTA His Sorb microtiter 8-well strips (Qiagen) and selections against GST-KIX were performed in glutathione-coated 96-well microtiter plates (Pierce). 200 μL target protein was added to each well (final concentration of 30 nM for GST-KIX and 100 nM for HisKIX) and incubated overnight with shaking at 4° C. Wells were washed three times with HisKIX or GST-KIX binding buffer to remove unbound protein. For blocking, binding buffer containing 6% milk was added to each well and incubated at 4° C. for 3 h. After blocking, wells were washed three times with binding buffer. Phage purified as described were added to each well and incubated for 3 h at 4° C. or 25° C. Nonbinding or weakly binding phage were removed by repeated washing (10 to 20 times, 1 min to 5 min in length, according to round) with binding buffer. Bound phage were eluted by incubation with 0.1 M glycine (pH 2.2) for 20 min. After neutralization of the eluted phage solution with 2 M Tris (pH 9.2), XL1 Blue E. coli cells in log phase were infected with input and output phage and incubated at 37° C. for 1 h. Serial dilutions of infected cells were plated on SOB agar plates containing 2% (w/v) glucose and 0.1 mg/mL ampicillin. Cells infected with output phage were used to make glycerol stocks and stored at −70° C.

5) Peptide synthesis and modification—Peptides were synthesized on a 25 μmol scale at the HHMI Biopolymer/Keck Foundation Biotechnology Resource Laboratory at the Yale University School of Medicine, New Haven, Conn. All peptides contained free N-terminal amines and amidated C-termini. Phosphoserine residues were introduced using an Fmoc-protected O-benzyl-phosphoserine derivative with standard coupling conditions. Crude peptides were purified by reverse-phase HPLC on a Vydac semi-preparative C18 column (300 Å, 5 μm, 10 mm×150 mm). Matrix-assisted laser desorption-ionization time-of-flight (MALDI-TOF) mass spectrometry was used to confirm peptide identity before further modification. Fluorescein-conjugated derivatives were generated by reaction of purified peptides containing single C-terminal cysteine residues with a 10-fold molar excess of 5-iodoacetamidofluorescein (Molecular Probes) in a 3:2 mixture of dimethylformamide: phosphate-buffered saline (DMF:PBS). Labeling reactions were incubated with rotation for 3-16 h at room temperature. Fluorescein-labeled peptides were purified by reverse-phase HPLC as described above, and characterized by MALDI-TOF mass spectrometry and amino acid analysis.

6) Fluorescence polarization—Fluorescence polarization experiments were performed with a Photon Technology International QuantaMaster C-60 spectrofluorimeter at 25° C. in a 1 cm pathlength Hellma cuvette. Serial dilutions of HisKIX were made in buffer containing 50 mM Tris (pH 8.0), 100 mM KCl, 12.5 mM MgCl$_2$, 1 mM EDTA, 0.1% Tween-20. Briefly, an aliquot of fluorescently labeled peptide was added to a final concentration of 25-50 nM and the binding reaction was incubated for 30 min at 25° C. Thirty minutes was a sufficient length of time for the binding reaction to reach equilibrium, as judged by an absence of change in the observed polarization value of the sample with the highest HisKIX concentration over 1 h. For competition experiments, serial dilutions of KID-AB$^P$ were incubated with 1.5 μM or 3 μM HisKIX and 25 nM fluorescein-labeled PPKID4$^P$ or PPKID6$^U$ (peptide$^{Flu}$) for 60 min at 25° C., respectively. For specificity measurements, carbonic anhydrase II (Sigma) or calmodulin (Sigma) was used as the target protein in place of HisKIX, and fluorescently labeled peptide was used at a final concentration of 50 nM. Carbonic anhydrase was serially diluted in binding buffer as described for HisKIX. Calmodulin was serially diluted in calmodulin folding buffer containing 20 mM Hepes (pH 7.5), 130 mM KCl, 1 mM CaCl$_2$, 0.05% Tween-20.

Polarization was measured by excitation with vertically polarized light at a wavelength of 492 nm (10 nm slit width) and subsequent measurement of the fluorescence emission at a wavelength of 515 nm (10 nm slit width) for 10 s in the vertical and horizontal directions. The polarization data were fit using Kaleidagraph v3.51 software to equilibrium binding equation (1), derived from first principles.

$$P_{obs}=P_{min}+((P_{max}-P_{min})/(2[\text{peptide}^{Flu}]))$$
$$([\text{peptide}^{Flu}]+[\text{target protein}]+K_d-(([\text{peptide}^{Flu}]+[\text{target protein}]+K_d)^2-4[\text{peptide}^{Flu}][\text{target protein}])^{0.5}) \quad (1)$$

In this equation, $P_{obs}$ is the observed polarization at any target protein (HisKIX, carbonic anhydrase or calmodulin) concentration, $P_{max}$ is the maximum polarization value, $P_{min}$ is the minimum observed polarization value, and $K_d$ is the equilibrium dissociation constant. Measurements from two to three independent sets of samples were averaged for each dissociation constant determination. For plots of fraction of fluorescently labeled peptide (peptide$^{Flu}$) bound as a function of target protein concentration, polarization values were converted to fraction of peptide$^{Flu}$ bound using the $P_{min}$ and $P_{max}$ values derived from equation (1), and the fraction of peptide$^{Flu}$ bound data were fit to equilibrium binding equation (2) using Kaleidagraph v3.51 software.

$$\theta_{obs}=((1/(2[\text{peptide}^{Flu}]))([\text{peptide}^{Flu}]+[\text{target protein}]+K_d-(([\text{peptide}^{Flu}]+[\text{target protein}]+K_d)^2-4[\text{peptide}^{Flu}][\text{target protein}])^{0.5}) \quad (2)$$

In this equation, $\theta_{obs}$ is the observed fraction of peptide$^{Flu}$ bound at any target protein concentration and $K_d$ is the equilibrium dissociation constant.

For competition experiments, observed polarization values were converted to fraction of peptide$^{Flu}$ bound using experimentally determined $P_{min}$ and $P_{max}$ values corresponding to the polarization of samples containing 25 nM peptide$^{Flu}$ alone and peptide$^{Flu}$ with 1.5 μM or 3.0 μM HisKIX, respectively. The fraction of peptide$^{Flu}$ bound data were fit to equation (3) using Kaleidagraph v3.51 software to determine the IC$_{50}$ value.

$$\theta_{obs}=((\theta_{max}-\theta_{min})/(1+([\text{competitor}]/IC_{50})^{slope}))+\theta_{min} \quad (3)$$

In this equation, $\theta_{obs}$ is the observed fraction of peptide$^{Flu}$ bound at any competitor peptide concentration, slope is defined as the slope at the inflection point and IC$_{50}$ is the concentration of competitor that reduces binding of peptide$^{Flu}$ by 50%.

Example 20

Characterization of Miniature Proteins as High Affinity Ligands for the CBP KIX Domain A. Do PPKID4$^P$ and PPKID6$^U$ Occupy the CREB KID Site on CBP KIX?

Figure 12:
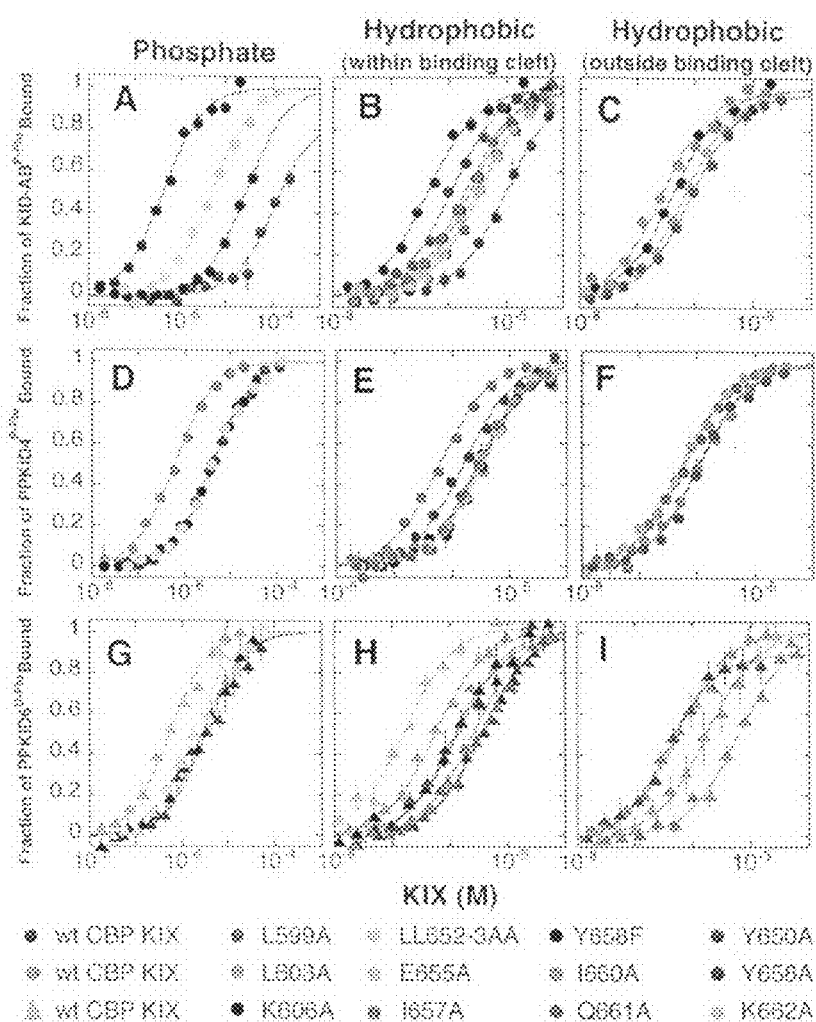
FIGS. 12A-I—Binding isotherms illustrating the equilibrium affinities of PPKID4$^P$, PPKID6$^U$ and KID-AB$^P$ for CBP KIX variants as determined by fluorescence polarization analysis at 25° C. Each plot illustrates the fraction of 25 nM (A-C) KID-AB$^P$, (D-F) PPKID4$^P$, or (G-I) PPKID6$^U$ bound as a function of the concentration of CBP KIX variant (M). Observed polarization values were converted to fraction of ligand$^{Flu}$ bound using $P_{min}$ and $P_{max}$ values derived from the best fit of the polarization data to equation (1). Curves shown represent the best fit of the data to equation (2). Phosphorylated ligands are indicated with circles, whereas unphosphorylated ligands are indicated by triangles. Each point represents an average of three independent trials; error bars denote standard error.

In our previous work, we reported that both PPKID4$^P$ and PPKID6$^U$ bind wild type CBP KIX with high affinity. In the case of PPKID4$^P$, the affinity (515±44 nM) was comparable to that of the full length phosphorylated CREB KID domain (KID-AB$^P$, $K_d$=562±41 nM); PPKID6$^U$ bound CBP KIX approximately three-fold worse ($K_d$=1.5±0.1 μM) that did KID-AB$^P$ (Rutledge, et al., J Am Chem Soc 2003, 125, 14336-14347). Here we made use of a set of twelve well-studied CBP KIX variants (Parker, et al., Mol Cell 1998, 2, 353-359) to compare the binding location and orientation of PPKID4$^P$ and PPKID6$^U$ to that of KID-AB$^P$, whose interactions with CBP KIX have been characterized in detail by NMR (Radhakrishnan, et al., Cell 1997, 91, 741-752). These twelve CBP KIX variants each contain a single alanine substitution within or around the CREB-binding groove, and their affinities for KID-AB$^P$ span a 3.7 kcal·mol$^{-1}$ range (Table 3). We reasoned that if PPKID4$^P$ and PPKID6$^U$ interact with CBP in a manner that mimics that of KID-AB$^P$, their affinities for these twelve variants should parallel those of KID-AB$^P$. The relative affinities of KID-AB$^P$, PPKID4$^P$ and PPKID6$^U$ for the panel of CBP KIX variants were measured by equilibrium fluorescence polarization. The results of these experiments are shown in FIG. 12 and Table 3.

B. Comparison of the Binding Modes of PPKID4$^P$ and KID-AB$^P$.

Figure 13:
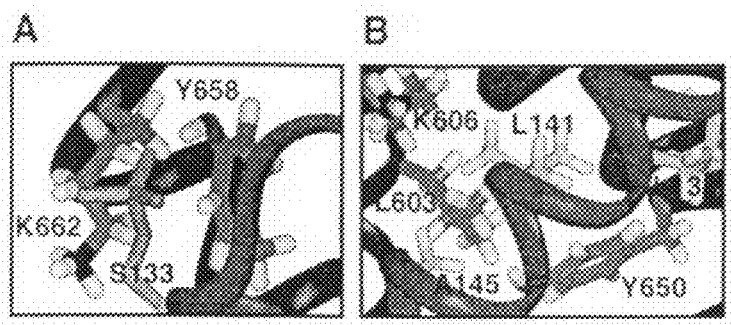
FIGS. 13A-B—Close-up view of: (A) phosphoserine and (B) hydrophobic contacts in the KID-AB$^P$•CBP KIX complex. The backbones of KID-AB$^P$ and CBP KIX are depicted as red and blue ribbons, respectively; the side chains of Y658, K662, L603, K606 and Y650 (from CBP KIX) and S133, L138, L141 and A145 (from KID-AB$^P$) are shown explicitly.

Recognition of phosphoserine. Recognition of the phosphoserine residue in KID-AB$^P$ by CBP KIX contributes heavily to the stability of the complex; loss of the phosphate results in a 3.5 kcal·mol$^{-1}$ loss in binding free energy. Therefore we first examined whether the PPKID4$^P$ phosphoserine contributes significantly to the binding energy of the PPKID4$^P$•CBP KIX complex. The CBP KIX variants Y658F and K662A each contain a mutation of a residue that directly contacts the KID-AB$^P$ phosphoserine (FIG. 13A). The Y658 side chain donates a phenolic hydrogen bond to one terminal phosphoserine oxygen whereas the K662 ammonium group forms a salt bridge with a second terminal phosphoserine oxygen. The Y658F and K662A CBP KIX variants both exhibit significantly decreased affinity for KID-AB$^P$, consistent with previous results, with equilibrium dissociation constants of 26±5 and 4.8±0.4 μM, respectively. These values correspond to binding free energies that are 2.5 and 1.5 kcal·mol$^{-1}$ less favorable, respectively, than the wild type KID-AB$^P$•CBP KIX complex. The free energy changes we measure with these two variants, as well as the Y658A variant (discussed below), are consistent with previous work and available structural information.

The Y658F and K662A variants of CBP KIX also exhibit significantly decreased affinity for PPKID4$^P$. The equilibrium dissociation constant of the PPKID4$^P$•Y658F complex is 4.1±0.2 μM. This value corresponds to a binding free energy that is 1.1 kcal·mol$^{-1}$ less favorable than that of the wild type PPKID4$^P$•CBP KIX complex, approximately one half the magnitude of the change seen with KID-AB$^P$. The equilibrium dissociation constant of the K662A•PPKID4$^P$ complex is 3.9±0.3 μM. This value corresponds to a binding free energy that is 1.1 kcal·mol$^{-1}$ less favorable than that of the wild type PPKID4$^P$•CBP KIX complex, exactly the value measured with KID-AB$^P$. These data suggest that the Y658 hydrogen bond and the K662 salt bridge each contribute significantly to the affinity of PPKID4$^P$ for CBP KIX. Interestingly, the hydrogen bond to Y658 is more important overall for KID-AB$^P$ than for PPKID4$^P$, whereas the salt bridge with K662 contributes almost equally for both peptides.

We also examined the affinities of KID-AB$^P$ and PPKID4$^P$ for the Y658A variant of CBP KIX in which the entire tyrosine side chain has been replaced by alanine. The NMR structure of the KID-AB$^P$•CBP KIX complex shows this aromatic ring packed against residue L128 on helix A of KID-AB$^P$. This variant binds KID-AB$^P$ with exceptionally low affinity, (K$_d$=142±12 μM) a loss in binding free energy of 3.5 kcal·mol$^{-1}$, presumably because the complex suffers from loss of both the phenolic hydrogen bond and an important hydrophobic packing interaction. Since PPKID4$^P$ lacks a residue corresponding to L128 on helix A, one would expect the stability of the PPKID4$^P$•Y658A complex to be comparable to that of the PPKID4$^P$•Y658F complex. Indeed, the equilibrium dissociation constant of the PPKID4$^P$•Y658A complex is 4.1±0.2 μM, corresponding to a free energy loss of 1.1 kcal·mol$^{-1}$, a value identical to that measured for the Y658F•PPKID4$^P$ complex.

Hydrophobic contacts. Next we considered those residues that line the shallow KID-AB$^P$ binding cleft on CBP KIX. Six of the twelve variants (L599A, L603A, K606A, Y650A, LL652-3AA and I657A) contain alanine in place of a residue within this cleft. For example, Y650 of CBP KIX comprises one face of the binding cleft and interacts with three hydrophobic side chains of KID-AB$^P$, including L138, L141 and A145 on KID-AB$^P$ (FIG. 13B). The Y650A variant binds KID-AB$^P$ with significantly reduced affinity (K$_d$=9.4±0.7 μM), corresponding to a 1.8 kcal·mol$^{-1}$ loss in binding energy. Together, residues L603 and K606 form one side of the binding cleft of CBP KIX, interacting with CREB residues L141 and A145. The L603A and K606A variants bind KID-AB$^P$ with equilibrium dissociation constants of 3.4±0.3 and 2.3±0.2 μM, corresponding to losses in binding free energy of 1.2 and 1.0 kcal·mol$^{-1}$ compared to wild type. Other CBP KIX residues that comprise part of the hydrophobic cleft are L653 and I657; both interact with CREB residue L141 in addition to other residues. As expected, variants LL652-3AA and I657A also bind KID-AB$^P$ with lower affinity (K$_d$=2.9±0.2 and 1.9±0.1 μM), corresponding to losses in binding free energy of 1.2 and 0.9 kcal·mol$^{-1}$, respectively. Located at the bottom of the binding cleft, residue L599 interacts with only one residue, P146, of CREB. The L599A variant binds KID-AB$^P$ with lower affinity, but to a lesser extent than other variants that make up the hydrophobic cleft; the KID-AB$^P$•L599A complex has an equilibrium dissociation constant of 1.1±0.1 μM, corresponding to a loss in binding free energy of 0.58 kcal·mol$^{-1}$. Thus, as expected, all CBP KIX variants of residues known to make hydrophobic contacts with CREB bind KID-AB$^P$ worse than wild type CBP KIX.

All six CBP KIX variants within the hydrophobic binding cleft also show diminished affinity for PPKID4$^P$, with equilibrium dissociation constants between 1.6±0.1 and 3.4±0.5 μM. These K$_d$ values correspond to the free energy changes between 0.58 and 1.0 kcal·mol$^{-1}$. Amazingly, the magnitude and rank order of the affinities of these six CBP KIX variants for PPKID4$^P$ mirror, with only one exception, the affinities measured for KID-AB$^P$. The sole exception to this trend is CBP KIX variant Y650A; this variant forms a complex with KID-AB$^P$ that is 1.8 kcal·mol$^{-1}$ less stable than the wild type complex whereas the complex with PPKID4$^P$ is only 0.95 kcal·mol$^{-1}$ less stable.

Residues surrounding the binding pocket. In addition to the variants described above which contain mutations within the KID-AB$^P$ binding pocket, we also examined three variants—E655A, I660A and Q661A—with an alanine substituted at a position surrounding the binding pocket. These variants may provide additional information about the binding site of ligands that do not bind to CBP KIX in the exact same orientation as KID-AB$^P$. The equilibrium dissociation constants of the complexes of these variants with KID-AB$^P$ fall between 0.27±0.03 and 0.93±0.07 μM, values very close to that of the wild type complex (ΔΔG=−0.26 and +0.48 kcal·mol$^{-1}$, respectively). These three CBP KIX variants bind PPKID4$^P$ with equilibrium dissociation constants between 0.54±0.05 and 1.1±0.1 μM, corresponding to free energy changes between −0.07 and 0.35 kcal·mol$^{-1}$; similar to KID-AB$^P$, these values are also close to those of the wild type complex.

TABLE 3

Equilibrium dissociation constants of complexes between PPKID4$^P$, PPKID6$^U$ and KID-AB$^P$ and selected CBP KIX variants.

| CBP KIX | K$_d$ (μM) KID-AB$^P$ | ΔΔG (kcal·mol$^{-1}$) | K$_d$ (μM) PPKID4$^P$ | ΔΔG (kcal·mol$^{-1}$) | K$_d$ (μM) PPKID6$^U$ | ΔΔG (kcal·mol$^{-1}$) |
|---|---|---|---|---|---|---|
| wild type | 0.41 ± 0.04 | | 0.61 ± 0.04 | | 0.54 ± 0.06 | |
| Phosphoserine contacts | | | | | | |
| Y658A | 142 ± 12 | 3.5 | 3.9 ± 0.3 | 1.1 | 1.7 ± 0.4 | 0.68 |
| Y658F | 26 ± 5 | 2.5 | 4.1 ± 0.2 | 1.1 | 2.8 ± 0.4 | 0.97 |
| K662A | 4.8 ± 0.4 | 1.5 | 3.9 ± 0.3 | 1.1 | 1.8 ± 0.3 | 0.71 |
| Hydrophobic contacts within cleft | | | | | | |
| Y650A | 9.4 ± 0.7 | 1.8 | 3.0 ± 0.3 | 0.95 | 1.3 ± 0.2 | 0.52 |
| L603A | 3.4 ± 0.3 | 1.2 | 3.4 ± 0.5 | 1.0 | 2.5 ± 0.3 | 0.91 |
| LL652-3AA | 2.9 ± 0.2 | 1.2 | 2.9 ± 0.2 | 0.93 | 0.14 ± 0.02 | −0.80 |

TABLE 3-continued

Equilibrium dissociation constants of complexes between PPKID4$^P$, PPKID6$^U$ and KID-AB$^P$ and selected CBP KIX variants.

| CBP KIX | K$_d$ (μM) KID-AB$^P$ | ΔΔG (kcal · mol$^{-1}$) | K$_d$ (μM) PPKID4$^P$ | ΔΔG (kcal · mol$^{-1}$) | K$_d$ (μM) PPKID6$^U$ | ΔΔG (kcal · mol$^{-1}$) |
|---|---|---|---|---|---|---|
| K606A | 2.3 ± 0.2 | 1.0 | 3.1 ± 0.2 | 0.97 | 1.2 ± 0.1 | 0.47 |
| I657A | 1.9 ± 0.1 | 0.90 | 2.7 ± 0.1 | 0.89 | 3.6 ± 0.4 | 1.1 |
| L599A | 1.1 ± 0.1 | 0.58 | 1.6 ± 0.1 | 0.58 | 3.3 ± 0.3 | 1.1 |
| Hydrophobic contacts outside cleft | | | | | | |
| Q661A | 0.93 ± 0.07 | 0.48 | 1.1 ± 0.1 | 0.35 | 0.41 ± 0.06 | −0.16 |
| E655A | 0.71 ± 0.05 | 0.32 | 0.54 ± 0.05 | −0.07 | 1.7 ± 0.2 | 0.68 |
| I660A | 0.27 ± 0.03 | −0.26 | 1.1 ± 0.1 | 0.35 | 6.1 ± 0.7 | 1.4 |

C. Comparison of the Binding Modes of PPKID6$^U$ and KID-AB$^P$.

Recognition of phosphoserine. PPKID6$^U$ lacks the phosphoserine that dominates the energetics of the PPKID4$^P$•CBP KIX and KID-AB$^P$•CBP KIX complexes. Therefore, if this ligand is bound in a manner that mirrors that of PPKID4$^P$ and KID-AB$^P$, it should be less sensitive to changes at positions Y658 and K662 of CBP KIX. Surprisingly, PPKID6$^U$ binds both variants with significantly decreased affinity relative to wild type CBP KIX. The equilibrium dissociation constants of the Y658F•PPKID6$^U$ and K662A•PPKID6$^U$ complexes are 2.8±0.4 and 1.8±0.3 μM, corresponding to free energy losses of 0.97 and 0.71 kcal·mol$^{-1}$, respectively, relative to the wild type complex. Interestingly, the Y658A variant binds PPKID6$^U$ better (K$_d$=1.7±0.4 μM) than the Y658F variant (K$_d$=2.8±0.4 μM), whereas Y658A and Y658F bind PPKID4$^P$ equally well. These results are not consistent with a model in which the α-helix in PPKID6$^U$ is positioned within the CBP KIX cleft in a manner that closely mimics that of KID-AB$^P$. In contrast, they support a model characterized by an overlapping, but alternate, binding mode for PPKID6$^U$ compared to PPKID4$^P$ and KID-AB$^P$.

Hydrophobic contacts. Mutation of the KIX side chains that line the KID-AB$^P$ binding pocket in CBP KIX (variants L599A, L603A, K606A, Y650A and I657A) results in complexes with PPKID6$^U$ that are 0.47 to 1.1 kcal·mol$^{-1}$ less stable than the wild type complex. In contrast, the complex with LL652-3AA is 0.8 kcal·mol$^{-1}$ more stable. Variants L599A, L603A, and I657A exhibit moderately diminished binding affinity to PPKID6$^U$ (K$_d$=3.3±0.3, 2.5±0.3, and 3.6±0.4 μM; ΔΔG=1.1, 0.91, and 1.1 kcal·mol$^{-1}$, respectively), whereas K606A and Y650A show smaller decreases in PPKID6$^U$ binding affinity (K$_d$=1.2 ±0.1 and 1.3±0.2 μM; ΔΔG=0.47 and 0.52 kcal·mol$^{-1}$, respectively). Ranking of the hydrophobic contact residues in order of energetic contribution to complex formation with each ligand reveals a pattern for PPKID6$^U$ binding unlike that for KID-AB$^P$ or PPKID4$^P$. For example, Y650 and L599 make the largest and smallest energetic contributions, respectively, to binding of KID-AB$^P$, whereas Y650 contributes least and L599 contributes most to complex formation with PPKID6$^U$.

Residues surrounding the binding pocket. Although CBP KIX variants E655A, I660A and Q661A display affinities for KID-AB$^P$ and PPKID4$^P$ comparable to wild type CBP KIX, two of these variants show significantly diminished affinity for PPKID6$^U$. Variant I660A exhibits the largest decrease in PPKID6$^U$ binding affinity of all CBP KIX variants in the panel, with an equilibrium dissociation constant of 6.1± 0.7 μM, corresponding to a free energy loss of 1.4 kcal·mol$^{-1}$. E655A also exhibits decreased affinity for PPKID6$^U$, albeit to a lesser extent (K$_d$=1.7±0.2 μM; ΔΔG=0.68 kcal·mol$^{-1}$), whereas Q661A binds PPKID6$^U$ with affinity comparable to wild type CBP KIX. Again, differences in the relative and absolute contributions of CBP KIX residues to the energy of complex formation with PPKID6$^U$ compared to PPKID4$^P$ and KID-AB$^P$ suggest an alternate, but overlapping binding site for PPKID6$^U$.

D. Is PPKID4$^P$ Folded when Bound to CBP KIX?

Figure 14:
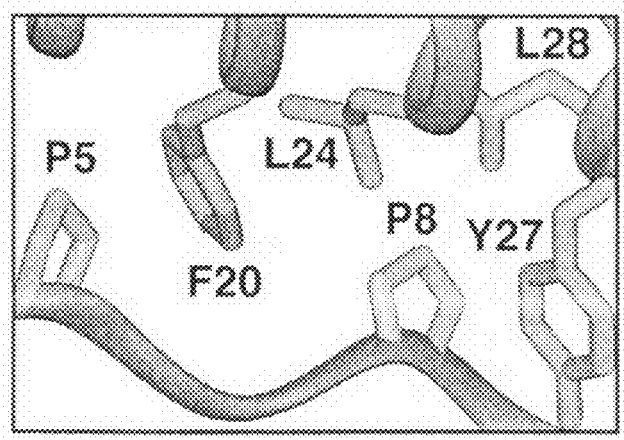
FIG. 14—Close-up view of packing between residues on the α-helix and PPII helix in the aPP hydrophobic core.

The results described above suggest that the α-helix in PPKID4$^P$ is positioned within the CBP KIX cleft in a manner that closely mimics that of KID-AB$^P$, but shed no light on whether PPKID4$^P$ is folded into an aPP-like hairpin conformation when bound. We previously reported that PPKID4$^P$ displays only nascent α-helicity in water in the absence of CBP KIX, as determined by circular dichroism. To explore whether PPKID4$^P$ folds into an aPP-like hairpin conformation upon binding to CBP KIX, we prepared a set of eleven PPKID4$^P$ variants in which alanine or sarcosine is substituted for a PPKID4$^P$ residue that comprises the hydrophobic core in the putative folded state (Blundell, et al., Proc Natl Acad Sci USA 1981, 78, 4175-4179). These variants include alanine substitutions along the face of the PPKID4$^P$ α-helix opposite the face used to contact CBP KIX (L17A, F20A, L24A, L28A and Y27A) and six variants with alanine or sarcosine substitutions along the PPII helix (P2A, P2Z, P5A, P5Z, P8A and P8Z). A close-up view of packing in the hydrophobic core is shown in FIG. 14.

We hypothesized that if PPKID4$^P$ folds upon binding within the CBP KIX binding cleft into an aPP-like conformation, then the stability of its complex with CBP KIX would depend on the presence of residues that comprise the intact hydrophobic core in a manner commensurate with their contribution to core stability, and the corresponding variants would display diminished affinity for CBP KIX. However, if the N-terminal region of PPKID4$^P$ interacts with the CBP KIX surface elsewhere, then the stability of the PPKID4$^P$•CBP KIX complex would not depend on the identities of putative folding residues from the PPKID4$^P$ α-helix. In this case, the variants would display affinity for CBP KIX comparable to wild type PPKID4$^P$.

TABLE 4

Binding affinities of PPKID4$^P$ variants for CBP KIX as determined by fluorescence polarization.

| PPKID4$^P$ | $K_d$ (μM) | ΔΔG (kcal · mol$^{-1}$) |
|---|---|---|
| Wild type | 0.61 ± 0.04 | |
| Polyproline helix variants | | |
| P2A | 0.87 ± 0.04 | 0.21 |
| P2Z | 0.83 ± 0.08 | 0.18 |
| P5A | 1.02 ± 0.09 | 0.30 |
| P5Z | 0.80 ± 0.03 | 0.16 |
| P8A | 1.07 ± 0.08 | 0.33 |
| P8Z | 0.78 ± 0.05 | 0.15 |
| α-helix variants | | |
| L17A | 0.68 ± 0.05 | 0.07 |
| F20A | 2.55 ± 0.25 | 0.85 |
| L24A | 1.16 ± 0.07 | 0.38 |
| Y27A | 3.09 ± 0.18 | 0.96 |
| L28A | 0.83 ± 0.11 | 0.18 |

E. Effects of PPKID4$^P$ Variants on CBP KIX Binding.

Figure 15:
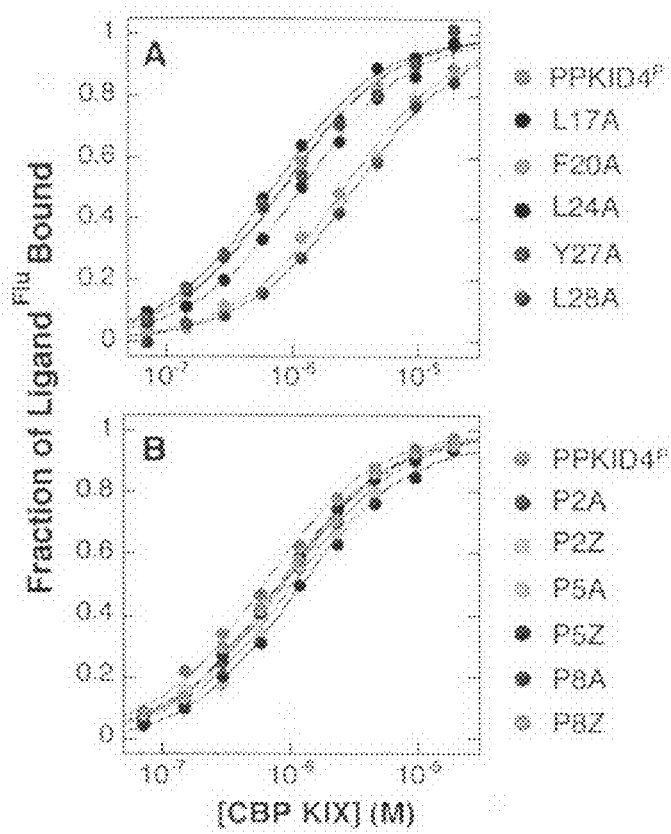
FIGS. 15A-B—Affinities of PPKID4$^P$ variants for CBP KIX as determined by equilibrium fluorescence polarization analysis. Each point represents an average of three independent trials. Observed polarization values were converted to fraction of ligand$^{Flu}$ bound using $P_{min}$ and $P_{max}$ values derived from the best fit of the polarization data to equation (1). Curves shown are the best fit of fraction of ligand$^{Flu}$ bound values to the equilibrium binding equation (2). A) Binding isotherms for PPKID4P variants L17A, F20A, L24A, Y27A and L28A. B) Binding isotherms for PPKID4P variants P2A, P2Z, P5A, P5Z, P8A and P8Z. Z indicates the substitution of sarcosine in place of alanine.

We used fluorescence polarization analysis to determine the CBP KIX binding affinities of eight PPKID4$^P$ variants in which one residue within the aPP hydrophobic core had been substituted with alanine. Five of these residues lie on the internal face of the aPP ☐helix, whereas three lie on the internal face of the PPII helix. We also studied three variants in which a proline residue on the internal face of the PPII helix was substituted by sarcosine (FIG. 15 and Table 4). The equilibrium dissociation constants of the PPKID4$^P$ variant•CBP KIX complexes range from 0.68±0.05 to 3.09±0.18 μM, corresponding to binding energies between 0.07 and 0.96 kcal·mol$^{-1}$ less favorable than the wild type complex. The stabilities of the variant complexes fall naturally into three categories. The least stable complexes containing variants F20A and Y27A were 0.85 and 0.96 kcal·mol$^{-1}$ less stable than the wild type complex; moderately stable complexes containing variants P5A, P8A and L24A were 0.3 to 0.38 kcal·mol$^{-1}$ less stable than the wild type complex. Six of the variants, P2A, P2Z, P5Z, P8Z, L17A and L28A, formed CBP KIX complexes with stabilities that were similar (0.07 to 0.21 kcal·mol$^{-1}$) to the wild type complex. It is striking that that those side chains that contribute significantly or moderately to the stability of the PPKID4$^P$•CBP KIX complex—F20, L24, Y27, P5 and P8—all lie at the center of the aPP hydrophobic core (FIG. 14). The aromatic side chain of F20 inserts between the side chains of residues P3 and P5, the branched side chain of L24 packs against P8 and F20, and the side chain of Y27 packs against P8. By contrast, those side chains that contribute minimally to stability—P2, L17 and L28—lie at the edge of the hydrophobic core of aPP and participate in fewer van der Waals interactions. Thus, these results support a model in which PPKID4$^P$ folds (although to a lesser extent than aPP) upon binding to CBP KIX into an aPP-like hairpin conformation.

F. Can PPKID Peptides Function as Transcriptional Activation Domains in Cultured Cells?

Eukaryotic transcriptional activators, such as CREB, stimulate gene expression primarily by recruitment of the general transcription machinery to the promoters of the genes they regulate (Ptashne, et al., Genes & Signals; Cold Spring Harbor Laboratory: New York, 2002). These transcription factors are modular in nature, containing a DNA binding domain that targets the activators specifically to the gene of interest, and an activation domain that binds, and thereby recruits, the transcriptional machinery. The functions of these two domains are separable; domains can be swapped among different activator proteins, or indeed replaced altogether with non-natural counterparts, to obtain molecules with novel activation activities (Ansari, et al., Curr Opin Chem Biol 2002, 6, 765-772). The development of fully artificial activators is an important goal in chemical biology, but although there has been considerable success in the development of novel DNA binding molecules, the development of artificial activation domains lags behind (Mapp, Organic and Biomolecular Chemistry 2003, 1, 2217-2220). By virtue of their ability to bind CBP, a coactivator protein that bridges transcription factors and the basal transcription machinery, we hypothesized that PPKID4$^P$ and PPKID6$^U$ might function as artificial activation domains when fused to a heterologous DNA-binding domain.

To investigate the activation potential of these ligands, we prepared a series of mammalian expression plasmids containing the CBP KIX ligands KID-AB, PPKID4 or PPKID6 fused to the C-terminus of the Gal4 DNA-binding domain (DBD) (residues 1-147). As a control, we used pAL1, which contained the Gal4 DBD alone. These constructs were transfected into HEK293 cells along with a previously described reporter plasmid containing five Gal4 binding sites upstream of the firefly luciferase gene (FIG. 16A) and a plasmid encoding *Renilla* luciferase to control for variable transfection efficiency. The cells were incubated at 37° C. for 36 h, lysed, and the ratio ® of activity of firefly and Rinella luciferase measured using the Dual-Luciferase® Reporter Assay System (Promega). The potency of each activation domain (fold activation) was determined by dividing the ® values measured in cells transfected with a Ga4 DBD fusion by the ® value measured in cells transfected with the pAL1 control. Based on a previous study that found a correlation between the CBP KIX-binding affinity and activation potency of short peptides (Frangioni, et al., Nat Biotechnol 2000, 18, 1080-1085), we expected PPKID4$^P$ and PPKID6$^U$ to activate transcription at level comparable to KID-AB$^P$ due to their similar affinities for CBP KIX.

G. Activation Potential of PPKID4, PPKID6 and KID-AB.

Figure 16:
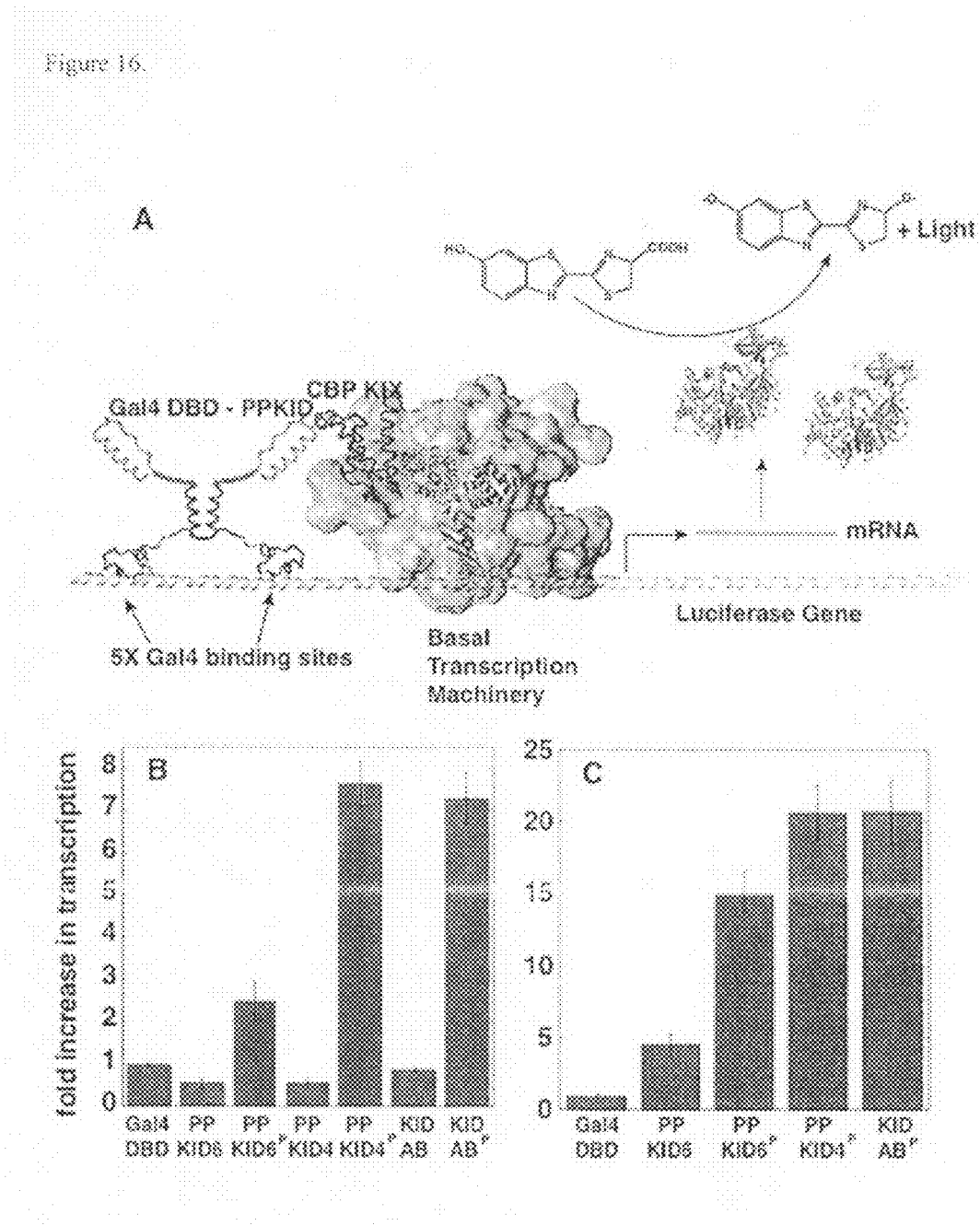
FIGS. 16A-C—(a) Transcriptional activation mediated by Gal4 DBD fusions of PPKID4, PPKID6 and KID-AB in HEK293 cells in the absence (b) or presence (c) of excess p300. The potency of each activation domain (fold activation) was determined by dividing the R values measured in cells transfected with a Ga4 DBD fusion by the R value measured in cells transfected with the pAL1 control. The R value refers to the ratio of the activity of firefly and Rinella luciferase measured using the Dual-Luciferase® Reporter Assay System (Promega). Bars and standard error represent the results from at least 3 independent trials. Where indicated, 5 μM forskolin was added to the culture media 6 h prior to harvesting cells. When indicated, cells were also transfected with an expression vector encoding full-length p300 under control of the CMV promoter (25 ng).
Figure 17:
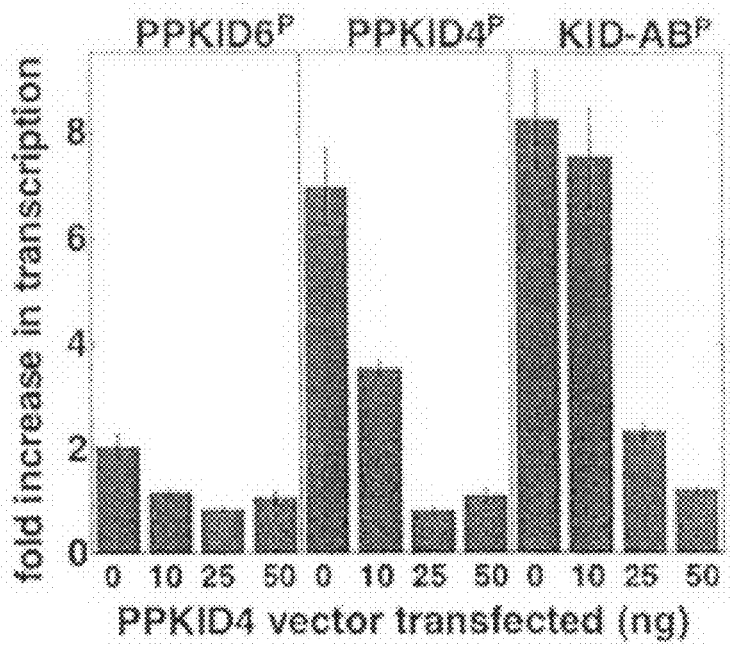
FIG. 17—Transcriptional inhibition by PPKID4$^P$ peptide in mammalian cells. For each peptide, 5 ng of the Gal4 DNA-binding domain fusion construct. For each peptide, HEK293 cells were transfected with 5 ng of the Gal4 DBD fusion construct and indicated amount of PPKID4 vector (PPKID4 expressed without Gal4 DBD) and assayed for activation.

First, we investigated the ability of KID-AB, PPKID4, and PPKID6 to activate transcription in the absence of forskolin, where phosphorylation of cellular proteins is not stimulated (FIG. 16B). We previously reported that PPKID4 and KID-AB possess low affinity for CBP KIX under these conditions (Rutledge, et al., J Am Chem Soc 2003, 125, 14336-14347) and would not be expected to effectively recruit CBP to the Gal4 promoter. Indeed, Gal4 DBD fusion proteins containing PPKID4 or KID-AB did not stimulate transcription over basal levels under these conditions. The fold increase in transcription measured in cells transfected with plasmids encoding these two fusion proteins was no higher than in cells transfected with PPKID6 also failed to activate transcription under these conditions, despite possessing significant affinity ($K_d$=1.5 μM) for CBP KIX.

Next, we investigated the ability of KID-AB, PPKID4 and PPKID6 to activate transcription under conditions where phosphorylation is stimulated. Addition of forskolin to the cell culture media induces the cAMP pathway, which activates protein kinase A (PKA) and leads to the phosphorylation of PKA substrates, including KID-AB and the PPKID peptides (Gonzalez, et al., Cell 1989, 59, 675-680; Johannessen, et al., Cell Signal 2004, 16, 1187-1199). As phosphorylation of KID-AB and PPKID4 dramatically increases their CBP KIX-binding affinity, we expected that phosphorylation of these ligands will also increase their ability to recruit CBP and hence, their transcriptional potency. Indeed, in the presence of forskolin, KID-AB and PPKID4 activate transcription 7.5-fold over basal levels. Phosphorylation of PPKID6 also increases its CBP KIX-binding affinity; however, with only 2-fold higher affinity for CBP KIX, it was not clear whether PPKID6$^P$ would be capable of activating transcription when PPKID6$^U$ could not. In fact, in the presence of forskolin, PPKID6 activated transcription 2.5-fold over basal levels.

H. Does Transcriptional Activation by the PPKID Peptides Occur Via the CBP/p300 Pathway?

Transcriptional activation by CREB KID occurs via recruitment of CBP to promoters where CREB is bound. However, transcription can be activated by a variety of different pathways. Therefore, it was of great interest to investigate whether, as we hypothesize, the observed transcription activation potential of PPKID4$^P$ and PPKID6$^P$ is dependent on recruitment of CBP. Towards this end, we compared the transcription potential of PPKID4$^P$ and PPKID6$^P$ in the presence and absence of exogenous p300, a paralog of CBP. An increase in the effective concentration of p300 in the cells should lead to an increase in transcriptional activation that occurs via the p300/CBP pathway. Thus, we expected that the levels of transcription activation elicited by PPKID4$^P$ and PPKID6$^P$ in the presence of exogenous p300 would be significantly higher than the levels of transcription observed with only endogenous CBP/p300.

As expected, in the presence of additional p300, KID-AB$^P$ activated transcription 20-fold over basal levels, confirming that the concentration of endogenous CBP/p300 in HEK293 cells is limiting (FIG. 16C). Similarly, PPKID4$^P$ activated transcription 20-fold over basal levels in the presence of exogenous p300, a 2.7-fold increase relative to PPKID4$^P$-dependent transcription mediated by endogenous CBP/p300 alone. Likewise, PPKID6$^P$ activated transcription 15-fold over basal levels in the presence of additional p300, a 6-fold increase relative to PPKID6$^P$-dependent transcription mediated by endogenous CBP/p300. Somewhat surprisingly, addition of p300 also increased transcription activation by PPKID6 in the absence of phosphorylation to levels 4.5-fold over basal transcription levels, whereas PPKID6 failed to activate transcription in the presence of only endogeous CBP/p300. Thus, although unphosphorylated PPKID6 is perhaps best described as a weak activation domain, it nevertheless activates transcription via the CBP/p300 pathway. These results are consistent with a model in which PPKID4 and PPKID6, like CREB KID, activate transcription by recruitment of CBP/p300 via the KIX domain to the promoters where they are bound.

I. Transcription Inhibition by PPKID4$^P$.

We have shown that transcriptional activation by PPKID4$^P$ and PPKID6$^P$ occur via the same pathway as CREB KID, the CBP/p300 pathway. Therefore it would be of interest to show that these activation domains indeed compete with each other to activate transcription in living cells. We compared the transcription potential of PPKID6$^P$, PPKID4$^P$ and KID-AB$^P$ in the presence of increasing amounts of the PPKID4$^P$ activation domain (without a DNA-binding domain). It is expected that increasing amounts of the PPKID4$^P$ activation domain will bind the limited supply of CBP in the cells, thus preventing transcription via the CBP/p300 pathway. Based on the above results, we hypothesize that the PPKID4$^P$ activation domain will inhibit transcription of the phosphorylated PPKID and CREB ligands.

As expected, transcriptional activation by PPKID4$^P$ was significantly reduced when a 2:1 ratio of PPKID4$^P$ activation domain:Gal4 DBD-PPKID4$^P$ was transfected in HEK293 cells. Cotransfection of a 5-fold excess of PPKID4$^P$ activation domain brought activation down to basal levels. Activation by KID-AB$^P$ was inhibited when a 5:1 ratio of PPKID4$^P$ activation domain:Gal4 DBD-KID-AB$^P$ was transfected. With a 10-fold excess of the PPKID4$^P$ activation domain, KID-AB$^P$ activation was completely inhibited. Due to its low level of activation, PPKID6$^P$ activation is brought down to basal levels in the presence of only a 2-fold excess of the PPKID4$^P$ activation domain.

In sum, the binding mode and orientation of two ligands for CBP KIX (PPKID4$^P$ and PPKID6$^U$) designed to mimic the natural ligand KID-AB$^P$ have been investigated. Binding affinity data with CBP KIX variants show that (despite conformational differences) PPKID4$^P$ binds in the same hydrophobic pocket of CBP KIX as KID-AB$^P$, possibly directed to this site by the phosphate group. Our results support a model in which PPKID4$^P$ folds into an aPP-like conformation upon binding to CBP KIX. PPKID6$^U$ binds an overlapping yet distinct region of CBP KIX. The distance separating the CBP KIX residues critical for binding this ligand suggests that PPKID6$^U$ binds in an open conformation. These ligands do not only bind their target with high affinity in vitro, but they also function in mammalian cells. PPKID4$^P$ and PPKID6$^P$ function as transcriptional activators much like the transcription factor CREB after which they were modeled. These ligands can act as artificial activation domains, and have the potential to serve as tools in understanding the mechanism of transcription activation.

J. Experimental Section.

1) Expression and purification of CBP KIX and KIX mutants—See above in Example 19.

2) Peptide Synthesis and Modification—PPKID4$^P$, PPKID6$^U$ and KID-AB$^P$ peptides were synthesized as described above in Example 19.

3) Fluorescence Polarization—See above in Example 19.

4) Gal4 DBD-peptide constructs—Peptides were cloned into a BamHI and SalI digested pAl$_1$ vector (a gift from John Frangioni) (Voss, et al., Anal Biochem 2002, 308, 364-372), which encodes the Gal4 DNA-binding domain and results in fusion of the peptide to the C-terminus to the Gal4 DBD. For PPKID4 inhibition experiments, PPKID4 was cloned into a BglII and BamHI digested pAl$_1$ vector, which removes the Gal4 DBD.

5) Cell Culture, Transfection and Luciferase Assays—HEK293 cells (CRL-1573 ATCC) were grown in DMEM containing 10% fetal bovine serum. Cells were plated in 24-well plates 24 hours prior to transfection. Cells were transfected using SuperFect transfection reagent (Qiagen) with 800 ng of total DNA. Included were 5 ng of peptide-Gal4 DNA-binding domain construct, 400 ng of 5× Gal4 firefly luciferase reporter plasmid (a gift from John Frangioni), 20 ng of a promoterless *Renilla* luciferase plasmid (Promega) for normalization and pBluescript SK+ carrier DNA. Where indicated forskolin was added to cell media 6 hours before harvested. Cells were harvested and assayed 36 hours after transfection and Turner Designs Model TD-20/20 luminometer.

Example 21

Preparation of a Universal Miniature Protein Phage Display Library

A combinatorial library designed to be used generally in the discovery and engineering of miniature proteins can also be constructed using the methods of the invention. This universal library is designed to display a combinatorial set of epitopes to enable the recognition of nucleic acids, proteins or small molecules by a miniature protein without prior knowledge of the natural epitope used for recognition. The universal library optimally is formed by varying (at least about) six residues on the solvent-exposed face of aPP which do not contribute to the formation of the hydrophobic aPP core. These residues of aPP include Tyr21, Asn22, Asp22, Gln23 and Asn26. All members of this universal library will retain the remarkable stability and compact structure of avian pancreatic polypeptide while introducing a diverse, functional, solvent-exposed surface available for recognition. The number of independent transformants ($2.5 \times 10^9$ clones) required to cover sequence space of a six-membered library is experimentally feasible.

Incorporation By Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed:

1. A modified avian pancreatic polypeptide (aPP) having a sequence selected from the group consisting of SEQ ID NO: 83, SEQ ID NO: 84, SEQ ID NO: 85, SEQ ID NO: 87, and SEQ ID NO: 88.

2. The modified avian pancreatic polypeptide of claim 1, wherein the modified avian pancreatic polypeptide is SEQ ID NO: 83.

3. The modified avian pancreatic polypeptide of claim 1, wherein the modified avian pancreatic polypeptide is SEQ ID NO: 84.

4. The modified avian pancreatic polypeptide of claim 1, wherein the modified avian pancreatic polypeptide is SEQ ID NO: 85.

5. The modified avian pancreatic polypeptide of claim 1, wherein the modified avian pancreatic polypeptide is SEQ ID NO: 87.

6. The modified avian pancreatic polypeptide of claim 1, wherein the modified avian pancreatic polypeptide is SEQ ID NO: 88.

7. An isolated avian pancreatic polypeptide modified by substitution of at least one amino acid residue, wherein the modified polypeptide comprises a sequence selected from the group consisting of: (a) an amino acid sequence selected from the group consisting of SEQ ID NO: 83, SEQ ID NO: 84, SEQ ID NO: 85, SEQ ID NO: 87, and SEQ ID NO: 88; and (b) an amino acid sequence at least 95% identical to any amino acid sequence selected from the group consisting of SEQ ID NO: 83, SEQ ID NO: 84, SEQ ID NO: 85, SEQ ID NO: 87, and SEQ ID NO: 88.

* * * * *

UNITED STATES PATENT AND TRADEMARK OFFICE
CERTIFICATE OF CORRECTION

PATENT NO. : 7,495,070 B2
APPLICATION NO. : 10/982727
DATED : February 24, 2009
INVENTOR(S) : Alanna S. Schepartz et al.

It is certified that error appears in the above-identified patent and that said Letters Patent is hereby corrected as shown below:

In the Specification:

Please change Item (73) to: "Yale University, New Haven, CT (US)"

Signed and Sealed this

Fifteenth Day of December, 2009

David J. Kappos
*Director of the United States Patent and Trademark Office*